US011236373B2

(12) United States Patent
Shaw et al.

(10) Patent No.: US 11,236,373 B2
(45) Date of Patent: Feb. 1, 2022

(54) HETEROLOGOUS PRODUCTION OF 10-METHYLSTEARIC ACID BY CELLS EXPRESSING RECOMBINANT METHYLTRANSFERASE

(71) Applicant: Ginkgo Bioworks, Inc., Boston, MA (US)

(72) Inventors: Arthur J. Shaw, Belmont, MA (US); Hannah Blitzblau, Arlington, MA (US); Donald V. Crabtree, Boston, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 16/648,117

(22) PCT Filed: Sep. 20, 2018

(86) PCT No.: PCT/US2018/051919
§ 371 (c)(1),
(2) Date: Mar. 17, 2020

(87) PCT Pub. No.: WO2019/060527
PCT Pub. Date: Mar. 28, 2019

(65) Prior Publication Data
US 2020/0231998 A1 Jul. 23, 2020

Related U.S. Application Data

(60) Provisional application No. 62/561,136, filed on Sep. 20, 2017.

(51) Int. Cl.
*C12N 9/00* (2006.01)
*C12P 7/64* (2006.01)
*C12N 9/02* (2006.01)
*C12N 9/10* (2006.01)

(52) U.S. Cl.
CPC .......... *C12P 7/6463* (2013.01); *C12N 9/0004* (2013.01); *C12N 9/1007* (2013.01)

(58) Field of Classification Search
CPC .... C12N 9/001; C12N 9/0071; C12N 8/0069; C12Y 201/07079; C12Y 103/00
See application file for complete search history.

(56) References Cited

U.S. PATENT DOCUMENTS 10,457,963 B2 * 10/2019 Shaw, IV .............. C12N 9/001
2002/0120958 A1 8/2002 Duhot et al.

FOREIGN PATENT DOCUMENTS

WO WO 2018/057607 3/2018

OTHER PUBLICATIONS

Poehlein et al. 2013; Draft genome sequence of Desulfotignum phosphitoxidans DSM 13687 strain FiPS-3. Genome Announcements 1(3): pp. 1-2, with SEQ ID No. 2 and No. 20 sequence alignments attached.*
Ling et al. Nov. 2016; Draft genome sequence of Marinobacter hydocarbonoclasticus strain STW2, a polyaromatic aromatic hydrocarbon degrading and denictrifying bacterium from rhizosphere of Seagrass Enhalus acodoides. EMBL/GenBank/DDBJ databases, pp. 1-4, comprising SEQ ID No. 4 and No. 22 alignments.*
Shamseldin et al. 2015; Untitled. EMBL/GenBank/DDBJ databases, pp. 1-3, comprising SEQ ID No. 4 and No. 22 alignments.*
Ploux Mar. 2016; Untitled. EMBL/GenBank/DDBJ databases, pp. 1-3, comprising SEQ ID No. 4 and No. 22 alignments.*
De Groot. Oct. 2017; Untitled. EMBL/GenBank/DDBJ databases, pp. 1-3, comprising SEQ ID No. 6 and No. 24 alignments.*
BRENDA:EC1.13.11.90, downloaded 2021; on the web at brenda-enzymes.org/enzyme.php?ecno=1.13.11.90, pp. 1-2.*
BRENDA:EC2.1.1.79, downloaded 2021; on the web at brenda-enzymes.org/enzyme.php?ecno=2.1.1.79, pp. 1-3.*
BRENDA:EC1.14.11.72, downloaded 2021; on the web at brenda-enzymes.org/enzyme.php?ecno=1.14.11.72, pp. 1-2.*
BRENDA:EC1.3.1.83, downloaded 2021, on the web at brenda-enzymes.org/enzyme.php?ecno=1.3.1.83, pp. 1-3.*
Bentley et al., "Engineering *Escherichia coli* to produce branched-chain fatty acids in high percentages" *Metabolic Engineering* 2016, 38, 148-158.
International Preliminary Report on Patentability issued in corresponding PCT Application No. PCT/US2018/051919, dated Mar. 24, 2020.
International Search Report and Written Opinion issued in corresponding application No. PCT/US2018/051919, dated Aug. 3, 2019.
Jiang et al., "Enhanced production of branched-chain fatty acids by replacing β-ketoacyl-(acyl-carrier-protein) synthase III (FabH)" *Biotechnology and Bioengineering* 2015, 112(8), 1613-1622.
Kuever et al., "Reclassification of Desulfobacterium phenolicum as Desulfobacula phenolica comb. nov. and description of strain SaxT as *Desulfotignum balticum* gen. nov., sp. nov" *International Journal of Systematic and Evolutionary Microbiology* 2001, 51, 171-177.
Machida et al., "Expression of Genes for a Flavin Adenine Dinucleotide-Binding Oxidoreductase and a Methyltransferase from Mycobacterium chlorophenolicum Is Necessary for Biosynthesis of 10-Methyl Stearic Acid from Oleic Acid in *Escherichia coli*" *Frontiers in Microbiology* 2017, 8, 12 pages.
Marquez et al., "Marinobacter hydrocarbonoclasticus Gauthier et al. 1992 and Marinobacter aquaeolei Nguyen et al. 1999 are heterotypic synonyms" *International Journal of Systematic and Evolutionary Microbiology* 2005, 55(3), 1349-1351.

(Continued)

*Primary Examiner* — Karen Cochrane Carlson
(74) *Attorney, Agent, or Firm* — Norton Rose Fulbright US LLP

(57) ABSTRACT

Disclosed herein are cells, nucleic acids, and proteins that can be used to produce branched (methyl)lipids, such as 10-methylstearic acids, and compositions that include such lipids. Cells disclosed herein comprise methyltransferase and/or reductase genes from bacteria of the class Gammaproteobacteria, which encode enzymes capable of catalyzing the production of branched (methyl)lipids from unbranched, unsaturated lipids. Saturated branched (methyl) lipids produced using embodiments of the present invention have favorable low-temperature fluidity and favorable oxidative stability, which are desirable properties for lubricants and specialty fluids.

32 Claims, 15 Drawing Sheets
Specification includes a Sequence Listing.

(56) References Cited

OTHER PUBLICATIONS

Sorokin et al., "*Thiohalorhabdus denitrificans* gen. nov., sp. nov., an extremely halophilic, sulfur-oxidizing, deep-lineage gammaproteobacterium from hypersaline habitats" *International Journal of Systematic and Evolutionary Microbiology* 2008, 58(12), 2890-2897.

\* cited by examiner

| Microorganism | 10Me16 observed | cfa homologs | tmp operon present | tmpB genome locus tag | tmpA genome locus tag | Reference |
|---|---|---|---|---|---|---|
| Desulfobacter curvatus DSM 3379 | yes | 2 | yes | B147_RS0124955 | B147_RS0124950 | Kohring, FEMS Microbiol. Lett. 119:303-08 (1994) |
| Desulfobacter postgatei 2ac9 | yes | 2 | yes | DESPODRAFT_RS04665 | DESPODRAFT_RS04670 | Dowling, Microbiol. 132:1815-25 (1986) |
| Desulfobacula toluolica Tol2 | yes | 3 | yes | TOL2_C28310 | TOL2_C28300 | Kuever, Int. J. Syst. Evol. Microbiol. 51:171-77 (2001) |
| Desulfotomaculum acetoxidans DSM 771 | no | 0 | no | - | - | Dowling, Microbiol. 132:1815-25 (1986) |
| Desulfuromonas acetoxidans DSM 684 | no | 0 | no | - | - | Dowling, Microbiol. 132:1815-25 (1986) |
| Escherichia coli MG1655 | no | 1 | no | - | - | Taylor, Biochem. 18:3292-3300 (1979) |
| Marinobacter hydrocarbonoclasticus ATCC 49840 | yes | 2 | yes | MARHY3375 | MARHY3376 | Márquez, J. Syst. Evol. Microbiol. 55:1349-51 (2005) |
| Pseudomonas putida KT2440 | no | 2 | no | - | - | Pini, FEMS Microbiol. Lett. 321:107-14 (2011) |
| Thiohalospira halophila DSM 15071 | yes | 2 | yes | SAMN05660831_00818 | SAMN05660831_00819 | Sorokin, Int. J. Syst. Evol. Microbiol. 48:1685-92 (2008) |

FIG. 2

| | 14:0 | SD | 16:0 | SD | 16:1 Δ9 | SD | 16:0cyc | SD | 10-methylene 16:0 | SD | 18:1 Δ11 | SD | 18:0 | SD | unknown | SD |
|---|---|---|---|---|---|---|---|---|---|---|---|---|---|---|---|---|
| pNC1071 | 4.9% | 0.2% | 48.2% | 0.1% | 5.9% | 0.0% | 16.5% | 0.1% | 10.3% | 0.1% | 9.8% | 0.2% | 0.7% | 0.1% | 3.7% | 0.1% |
| pNC1072 | 4.4% | 0.0% | 48.7% | 0.1% | 11.6% | 0.1% | 22.9% | 0.1% | 0.0% | 0.0% | 7.8% | 0.1% | 0.6% | 0.0% | 4.0% | 0.1% |
| pNC1073 | 4.6% | 0.1% | 44.1% | 0.2% | 11.6% | 0.1% | 19.8% | 0.2% | 4.2% | 0.1% | 9.6% | 0.1% | 0.6% | 0.1% | 5.5% | 0.1% |
| pNC1074 | 5.8% | 0.1% | 46.2% | 0.2% | 5.1% | 0.1% | 14.2% | 0.1% | 16.0% | 0.2% | 6.8% | 0.1% | 0.7% | 0.0% | 5.1% | 0.1% |
| pNC1076 | 8.5% | 0.1% | 47.1% | 0.1% | 2.1% | 0.2% | 7.8% | 0.2% | 23.5% | 0.1% | 5.8% | 0.0% | 0.6% | 0.1% | 4.6% | 0.0% |
| pNC53 | 4.3% | 0.1% | 48.3% | 0.2% | 10.5% | 0.0% | 23.1% | 0.1% | 0.0% | 0.0% | 9.2% | 0.1% | 0.7% | 0.1% | 3.9% | 0.0% |

FIG. 6

```
D_curvatus_tmpB(SEQ ID NO:8)        ------------------------------------------------------------
D_phenolica_tmpB(SEQ ID NO:10)      ------------------------------------------------------------
D_toluolica_tmpB(SEQ ID NO:12)      ------------------------------------------------------------
D_balticum_tmpB(SEQ ID NO:2)        ------------------------------------------------------------
D_postgatei_tmpB(SEQ ID NO:14)      ------------------------------------------------------------
M_hydrocarbonclasticus_tmpB(SEQ ID  MAQGTAPKTDYSD-SNTKAHVLSLPLENSQADREPHSYERWLIAKLMRAGSPAIRFQLM
                              NO:4)
T_halophila_tmpB(SEQ ID NO:6)       ------------------------------MQGNTPHGRAKGADLALAERILACMGNPALAVILM
H_ochraceum_tmpB(SEQ ID NO:16)      MDINTSIQQESASEPAQRANPLSLETGHRRSMSGPRAPERWVAVQLLNLAGSPVAIELM
M_aquaeolei_tmpB(SEQ ID NO:18)      MAQSTAHKPELPIKEZHRAHVLSLPIERGQSDREPHSYERWLIHKLMRNAGSPIRFRLM
E._coli_cfa(SEQ ID NO:45)           ------------------------------MSSS---CIEEVSVPDDNWYRIANELLSRAGI- D_curvatus_tmpB(SEQ ID NO:8)        ----------------------------TVNGSNNPYDIQIKNDRLLYQRVIHEPALGLGEAYMDQWWECRA--LDQFMAKVLR
D_phenolica_tmpB(SEQ ID NO:10)      ----------------------------KVNGRPFYDIQVKNDMLYQRVLSKAALGLGESYMDQWWECKA--LDRFIDKILR
D_toluolica_tmpB(SEQ ID NO:12)      ----------------------------KVNGERFYDIQVKNDNLIQRVLSKAALGLGESYMDQWWECKA--LDRFIDKILR
D_balticum_tmpB(SEQ ID NO:2)        ----------------------------RVNGDRPFDIRIKNDQFFQRVTSSPALGLGESYMDGWWDCFA--EDQFIEKVLR
D_postgatei_tmpB(SEQ ID NO:14)      ----------------------------TVNGSNPFYDIQVKNDRFYQRIIHEPALGLGEAYMDNWWECRA--LDQFIAKVLC
M_hydrocarbonclasticus_tmpB(SEQ ID  NGEVIEPEQ-GLARFTLRLKDHKALYSLVANPNLAFGDLISAGRLEIDGDLPDLMESLIR
                              NO:4)
T_halophila_tmpB(SEQ ID NO:6)       DGSRVGPSD---TVADVAYADRRALWAIALNADLHFGDLYAAGRVRIDGDLQTFLETGIR
H_ochraceum_tmpB(SEQ ID NO:16)      NGERVHPAAGGTERFTLRIGDRKALYGMLSNPNLAFGDLYSAGRIDVDGDLAEFLTEVTA
M_aquaeolei_tmpB(SEQ ID NO:18)      NGDVIEPEV-QDARFTNLTDHKALYSLVANPNLAFGDLYAAGRLEIDGDLPDLMESLYR
E._coli_cfa(SEQ ID NO:45)           ------------AINGSAPADIRVKNPDFFKRVLQBGSLGLGESYMDGWWECDR-LDMFFSKVLR

* = Conserved in TmpB sequences, but not in E. coli cfa sequence
*** = Single, fully conserved residue in all sequences
:   = Amino acids with strongly similar properties
.   = Amino acids with weakly similar properties
```

FIG. 7A

```
D_curvatus_tmpB (SEQ ID NO:8)           ANLGEVLKKEWQITWNILKARLEN-----QQSSRRAEMVGQSHYDVGNELYQGMLDK--QMQ
D_phenolica_tmpB (SEQ ID NO:10)         ADLVNKIRQDWNTTWEILKARIIN-----LQKPDRAPMVGQKHYDVGNDLYQAMLEK--RMQ
D_toluolica_tmpB (SEQ ID NO:12)         ADLVNKIRQDWNTTWEILKARIIN-----LQKPDRAPMVGQKHYDVGNDLYQAMLDK--RMQ
D_balticum_tmpB (SEQ ID NO:2)           ANLLRQIKQDRITAMNAIMAKIPN-----LQTIKRAFTVGKQHYDIGNDLYQMMLGK-RMQ
D_postgatei_tmpB (SEQ ID NO:14)         ANLGQVLKKEWRITWNLITAKLEN-----QQSKRRAFMVGQRHYDIGNDLYQGMLDK--QMQ
M_hydrocarbonclasticus_tmpB (SEQ ID     SVHAAAROK----RWLDALMKNHMNPRATGISEAKENIHHYDLGNEFYQLWLDNAEMQ
                      NO:4)
T_halophila_tmpB (SEQ ID NO:6)          AMDGQPTP--WPLR--FLH--BWQ-NRPRRNSLNGSRENIHHHYDLGNDFYRLWLDQEVMQ
H_ochraceum_tmpB (SEQ ID NO:16)         HVERQQAR--MPASARWLGR---GRATPKAASERAAKGNIQHYDLGNDFYRLWLDRAAMQ
M_aquaeolei_tmpB (SEQ ID NO:18)         AVHAAAROK----WP----RWLDALMKNHMNPRATGISEAKENIHHHYDLGNAFYQLWLDEAEMQ
E._coli_cfa (SEQ ID NO:45)              AGLENQLFHHFKDTLRIAGARLEN-----LQSKKRAWIVGREHYDLGNDLFSRMLDP-FMQ
                                         *    *          ;    *  :**:**  ;     *:

D_curvatus_tmpB (SEQ ID NO:8)           YTCGYWKDA-TTLDQPQEAKLALVCRKLKLAPGMKVLELGCGFGGFAHYAATKYGVEVTG
D_phenolica_tmpB (SEQ ID NO:10)         YTCGYWRAA-DTIESAQRAKLEIVCRKIGIKPGMKVTLELGCGFGGFARYBAQKYDAHVTG
D_toluolica_tmpB (SEQ ID NO:12)         YTCGYWETA-DTIESAQRAILEIVCRKIGLKPGMKVTLELGCGFGGFARYAAQKYDAHVTG
D_balticum_tmpB (SEQ ID NO:2)           YTCGYWKDA-RNLDEAQPEAKLAIVCRKLKLAIAPGMWNVTLELGCGFGGFARYAAKYQVSVTG
D_postgatei_tmpB (SEQ ID NO:14)         YTCGYWKDA-TTLDQPQEAKLAIVCRKLKIEPGMKVTLELGCGFGGFARYAATRYGVEVTG
M_hydrocarbonclasticus_tmpB (SEQ ID     YTCAYYEHPGNTLEQAQLAKLEHVCRKLRLRPGMTVVEAGCGWGGLARFMARNYGVKVRS
                      NO:4)
T_halophila_tmpB (SEQ ID NO:6)          YTCAYTPSESASLEPAQTAKLIHHYCRKILRLKPGDTVVEAGCGWGGLARFMAKHYGVKYRA
H_ochraceum_tmpB (SEQ ID NO:16)         YTCAYYEEPELITLEQAQQAHLEHVCRKLALQPGQRVVELGCGWGGLARYMARETGVSVRA
M_aquaeolei_tmpB (SEQ ID NO:18)         YTCAYYEQADNTLEQAQLAKLEHVCRKLRLKPGMTVVEAGCGWGGLARYMARHYGYKVHS
E._coli_cfa (SEQ ID NO:45)              YSCAYYEQA-DNLESAQQAKLKMICEKLQLKPGMRVLDIGCGWGGLAHYMASNYDVSVTG
                                        *::*.*;    ****   *     :****;**:**;  *;**;**

♦ = Conserved in TmpB sequences, but not in E. coli Cfa sequence
* = Single, fully conserved residue in all sequences
: = Amino acids with strongly similar properties
. = Amino acids with weakly similar properties
```

FIG. 7B

```
D_curvatus_tmpB (SEQ ID NO:8)          YTVSKEQARFGKELCRGLP----VDIRLLADYRTATGEYDRVVSIGLMEHVSYKNYGTIMK
D_phenolica_tmpB (SEQ ID NO:10)        FTVSREQAAF3KKQCRGLP----FVDIRLLIDYRNASGLYDRVVSIGMMEHVGYKNYRAYME
D_toluolica_tmpB (SEQ ID NO:12)        FTVSREQAAFAKKQCRGLP----VDIRLLIDYRNASGLYDRVVSIGMKEHVGYKNYPAIME
D_balticum_tmpB (SEQ ID NO:2)          FTVSEKQAEFGREYCKDLE----VDIRLLIDYRNARGTYDRILSIGLMEHVGFKNYRTYME
D_postgatei_tmpB (SEQ ID NO:14)        YTVSKEQVKFAEHLCKGLP----VDIRLLADYRTATGEYDRVLSIGLMEHVGYKNYGTIMK
M_hydrocarbonclasticus_tmpB (SEQ ID    YNISREQLAYAQAESERQGLDGLITYVEDDYRNITGQIDAFVSVGMLEHVGKENYRALSE
    NO:4)
Z_halophila_tmpB (SEQ ID NO:6)         FNVSQEQLRFAEEAERQGLSDRVEYVEIDYRNIEGTYDVFVSVGMLEHVGTEQKFELGA
H_ochraceum_tmpB (SEQ ID NO:16)        TNISREQVEYAREQAAFEGLDDRIEYVILDYRNISGEYDAFVSVGMLEHVGTDNYATVAR
M_aquaeolei_tmpB (SEQ ID NO:18)        YNISLEQLAYARAEAERQGLDNLVTYVEDDYRNIEGQYDAFVSIGMLEHVGRDNYFALSE
E_coli_cfa (SEQ ID NO:45)              YTIISAEGQKMAQERCEGLD----VTILLQDYRDLNDQFDRIVSVGMFEHVGPKHYDTYFA
                                          .  :* * :*          :.*  *  **  :    *..*:. .      :

D_curvatus_tmpB (SEQ ID NO:8)          LTNRLLRDDGTALLHTIGSNASCSACNFWTAKYIFPNGMLPSIAQLGRAME-NQFVMEDW
D_phenolica_tmpB (SEQ ID NO:10)        LTNRLLKDEGIAFVHTIGSNVSRKICNFWTVKYIFPNSSLPSLPSIAFIGRAME-GLFVVEDN
D_toluolica_tmpB (SEQ ID NO:12)        LTNRLLKDEGIAFVHTIGSNVSRKICNFWTVKYIFPNSSLPSIAFLGRAME-GLFVVEDN
D_balticum_tmpB (SEQ ID NO:2)          LTNRLLKDGIAFVHTIGGNITTRICNFWTAKYIFPNSVLPSSELGRAME-GLFVLEDC
D_postgatei_tmpB (SEQ ID NO:14)        LTNRLLRDDGIALVHTIGRNDSRCACHSWTAKYIFPNGMLPSIAQLGRAME-NQFVMEDW
M_hydrocarbonclasticus_tmpB (SEQ ID    IKRSLKPNGIALLHSIGRNRPM-LMNAWIERKIFPGAYPSIGEFMEICHSGDFSVLDV
    NO:4)
Z_halophila_tmpB (SEQ ID NO:6)         VIDRVLAPHGRGLIHTIGRNRPQ-LKMFWIERKIFPGAYFFTLREMAAIFPYAPSIQDV
H_ochraceum_tmpB (SEQ ID NO:16)        LIRNHLRPDGIALIHTIGRNRPA-GTMAWIERKIFPGAYPSITQLTGLAEAGPLSVLDI
M_aquaeolei_tmpB (SEQ ID NO:18)        LIRKSLKPNGIALLHSIGPNRPM-LMNAWIERKIFPGAYPSIGEFMEICHSDFSVLDV
E_coli_cfa (SEQ ID NO:45)              VVDRNLKFEGIFLLHTIGSKKTDLNVDFWINKYIFPNGCLPSVEQIAQSSE-PHFVMEDW
                                       : .  :  *:* *  .      :. *: *:**..  * :         
```

FIG. 7C

< = Conserved in TmpB sequences, but not in E. coli Cfa sequence
* = Single, fully conserved residue in all sequences
: = Amino acids with strongly similar properties
. = Amino acids with weakly similar properties

```
D_curvatus_tmpB (SEQ ID NO:8)          HNFGEDYDKTLMAWYENFKQVWPNLEDRYSDRFYRMWEYILLSCAGGFRSRSMQLWQIVM
D_phenolica_tmpB (SEQ ID NO:10)        HNFGEDYDKTLMAWHENFKKAWPGLKEKYDERFYRMWTYLLSCAGGFRSRSMQLWQIVM
D_toluolica_tmpB (SEQ ID NO:12)        HNFGEDYDKTLMAWHENFKKAWPGLKEKYDERFYRMMTYLLSCAGGFRSRSMQLWQIVM
D_balticum_tmpB (SEQ ID NO:2)          HNFGEDYDKTLMAWYDNFKAAWPKLKNRYDDRFYRMWEYLLSSAGGFTRARSMQLWQMVL
D_postgatei_tmpB (SEQ ID NO:14)        HNFGEDYDKTLMAWYENFRQVWPKLKIDRYNDRFYRMWEYLLSCAGGFRSRSMQLWQIVM
M_hydrocarbonclasticus_tmpB (SEQ ID NO:4)  ENLRLHYAQTLSHWTERFEANAERVTEMYDEHFTRAWRLYLAGSIAAFRAGSLQLFQVVF
T_halophila_tmpB (SEQ ID NO:6)         ENIRLHYARTLQRNLERFEANVETVRQMFDEHFVRTWRLYLAGSIASTTGELQLFQTVF
H_ochraceum_tmpB (SEQ ID NO:16)        ENLRLHYAETLTDWLARYEDNIDQYRAMYDEHFARAWRLYLSGSIAAFRAGTLQLFQMYL
M_aquaeolei_tmpB (SEQ ID NO:18)        ENLRLHYAQTLTHWMDNFTANQDQVTEMYDEHFTRAWRLYLAGSIAAFRAGSIQLFQVVF
E_coli_cfa (SEQ ID NO:45)              HNFGADYDTTLMAWYERFLAAWPEIADNYSERFKRMFTYLMACAGAFRARDIQLMQVVF
                                       :*:  **:. * :** :    * ::* *.**:  ** :*:****..: :.*::*::*

D_curvatus_tmpB (SEQ ID NO:8)          TKQGTSAFCCRLV-----
D_phenolica_tmpB (SEQ ID NO:10)        TKQGRTRPDCRIN-----
D_toluolica_tmpB (SEQ ID NO:12)        TKPGRTRPDRRIN-----
D_balticum_tmpB (SEQ ID NO:2)          TRPGRFKPDCRIS-----
D_postgatei_tmpB (SEQ ID NO:14)        TKQGTSAFCCRLV-----
M_hydrocarbonclasticus_tmpB (SEQ ID NO:4)  THGDNNQLPQSRQDLYAFPATEGN------
T_halophila_tmpB (SEQ ID NO:6)         TRPDYNELPWSRAYLYTTAGEEGA------
H_ochraceum_tmpB (SEQ ID NO:16)        AHPDNNGIPRNRKRLHTAPAYFEEPAA
M_aquaeolei_tmpB (SEQ ID NO:18)        THGDNNQLPQSRQBLYFTATEEGV------
E_coli_cfa (SEQ ID NO:45)              SRGVENGLRVAR------
                                       : :

< = Conserved in TmpB sequences, but not in E. coli Cfa sequence
* = single, fully conserved residue in all sequences
: = Amino acids with strongly similar properties
. = Amino acids with weakly similar properties
```

FIG. 7D

```
D_curvatus_tmpA  (SEQ ID NO:26)       -MIEKEIIYVGGGPAGSACAWKLKQRGITPLVLDKY-SFPRRKVCAGWVTPAVFLL-EF
D_phenolica_tmpA (SEQ ID NO:28)       -MIDSKIIYVGGGPAGSACAWKLKQAEEQILILDRM-PFPRSKLCAGWINPKALNAI-DF
D_toluolica_tmpA (SEQ ID NO:30)       -MIDSKIIYVGGGPAGSACAWKLKQAEEQILILDRK-PFPRSKLCAGWINPKALNAI-DF
D_balticum_tmpA  (SEQ ID NO:20)       -MIQTDVIIVGGGPAGSACAARLKNTGMDVRILDKQ-RFPRKKLCAGWISPGVFDDL-GY
D_postgatei_tmpA (SEQ ID NO:32)       -MINKEIIYVGGGPAGSACAWTLKQKGITPLVLDKY-SFPRPKVCAGWTTPAVFKLL-EL
M_hydrocarbonclasticus_tmpA (SEQ ID NO:22) -MDHYDVIIVGAGPAGSTLARSIEDAGKNVLVIDKA-SFPRDKTCAGWVTPAVMESL-DI
T_halophila_tmpA (SEQ ID NO:24)       MSERSDVLIVGSGFGGSTLGRALARQLDVTIVDKQ-TFPRDKVCAGWVTPAVMESL-DL
H_ochraceum_tmpA (SEQ ID NO:34)       MSRTHDVIIVGGGPSQSTLAWALERRGIRPLVMDKA-EFPRDKTCAGWVTPAVMSEL-EV
M_aquaeolei_tmpA (SEQ ID NO:36)       -MEYIDIIIVGAGPAGSTLARALEDSGKRVLIIDKQ-AFPRDKTCAGWVTPAWASL-DI
Archaeoglobus_fulgidus_AF0464 (SEQ ID NO:46) ---MIDVVVGAGPAGSMAAKTAAEQGLRYLLVEKRQEIGTPVRCAEGISRESIEKFEV
                                         :   *:*:* *:*  * . *  . .        *          *  *

D_curvatus_tmpA  (SEQ ID NO:26)       QGDDYPY--TFSQFDRIHFHMFG---IKIPV------FTRQTAVERVEFDAWMISRAHVFY-
D_phenolica_tmpA (SEQ ID NO:28)       KKQEYPF--LLHPVDRIHFYLFG---VHIPV-----QTRQYAIRRVEFDDMKVKRANVPV-
D_toluolica_tmpA (SEQ ID NO:30)       KKQEYPF--LLHPVDRIHFIEFLFG---VHIPV-----QTRQYAIRRVEFDDWMVKRANVPV-
D_balticum_tmpA  (SEQ ID NO:20)       DFDTYPH--ALTRIHGITHFRLFQ---VPLPV-----RTHQTAIRRIEFDHWILLQRAGVPV-
D_postgatei_tmpA (SEQ ID NO:32)       RGDDYPY--TVSQFDRINFHLFG---LKIPV------FTRQYAVRVEFDAWLICAGVPY-
M_hydrocarbonclasticus_tmpA (SEQ ID NO:22) NPANYANGRTLQPIRRFRIGMMG---QPAVENDHHG-IVSYGIRBCEFDAFILERVRSPK-
T_halophila_tmpA (SEQ ID NO:24)       DPNEYARDAVLQPIHAFRTGMLG---QRTVVSRYPE-PASYGIBRYBFDAWLLERAINDGV
H_ochraceum_tmpA (SEQ ID NO:34)       DLEDFAKHCVLQPIHMFRIGMMKG---QRAVNHHGDSPVSYGILRRQPDNYLLQRTGADK-
M_aquaeolei_tmpA (SEQ ID NO:36)       DPGRYSVGRTLQPIRRFRIGMMG---QSAVENDHGD-IVSYGIERCEFDDYILERAECEN-
Archaeoglobus_fulgidus_AF0464 (SEQ ID NO:46) DKKWLAAE------VTGAKIYAFNKTEIVMSEEMAGNEVGVVLERKIEFDRHVARLAAKAGA
                                                                 . :*     * *    :  ::

* = Conserved in TmpB sequences, but not in E. coli Cfa sequence
* = Single, fully conserved residue in all sequences
: = Amino acids with strongly similar properties
. = Amino acids with weakly similar properties
```

FIG. 8A

```
D_curvatus_tmpA   (SEQ ID NO:26)              ---KTHCVKNIIR-------------KNGFYIIDDQYRCRYLIGAGGTHCPVYKTFFTQKRS
D_phenolica_tmpA  (SEQ ID NO:28)              ---HTHTVKKIIK-------------KNGFYIIDNQYRCQYLVGAGGTHCPVFRVFFSKDEK
D_toluolica_tmpA  (SEQ ID NO:30)              ---HTHTVKKIIK-------------KNGFYIIDNQYBCQYLVGAGGTHCPVFRVFFSKDEK
D_balticum_tmpA   (SEQ ID NO:20)              ---HTHAVKKIQR-------------IRSGYVIDDQFECRYLVGAGGTHCPVRRTPMEPVPS
D_postgatei_tmpA  (SEQ ID NO:32)              ---HTYCVRNIIP-------------KNGFYIIDDQYQCKYLIGAGGTHCPVYKTFFTQTRP
M_hydrocarbonclasticus_tmpA (SEQ ID NO:22)    ---QLATPVKSIVR------------MNGHNVNNWQWQAPLLIGAGGHFCPVARQLGT-GPG
T_halophila_tmpA  (SEQ ID NO:24)              RTAQGQPLKELRR-------------EDGEWVLNDHLRTPLLIGAGGHFCPVARHLGAAKPG
H_ochraceum_tmpA  (SEQ ID NO:34)              --ALGVKFESLER-------------DADGLWCVNGEYRAPLVVGAGGHFCPIAARLGE-GPG
M_aquaeolei_tmpA  (SEQ ID NO:36)              ---QLATAVRSINR------------MNGNWVINDQWQAPLIVGAGGHFCPVARLLGD-GPG
Archaeoglobus_fulgidus_AF0464
                  (SEQ ID NO:46)              EVYVKTAMVDFERKDGKVEVELRRLGEIDN-----EVETRLIGADGVESKIGRRAGIIKTL
                                                  :  : :  :               :  :::****  *::

D_curvatus_tmpA   (SEQ ID NO:26)              RPSKSLIVAVEKEV-------PYDIVHKQCHLWFFDHG--LPGYAWLPKGNNWLNIGI
D_phenolica_tmpA  (SEQ ID NO:28)              RPMKSMIAAVEQEY-------VCDYQDSRCHIWFFDKE--LPGYSWTLPKGNGWLNIGI
D_toluolica_tmpA  (SEQ ID NO:30)              RPMKSMIAAVEQEY-------VCDYQDSRCHIWFFDEK--LPGYSWVLFKGNGWLNIGI
D_balticum_tmpA   (SEQ ID NO:20)              RPETARIAAVEREP-------QGFQRVRKCHIWYLEKG--LPGYAWYLPKKGGWINIGI
D_postgatei_tmpA  (SEQ ID NO:32)              RPFKSLIVAVEKEV-------PYDISHHQCHLWFFDHG--LPGYAWVLFKGNNWLNIGI
M_hydrocarbonclasticus_tmpA (SEQ ID NO:22)    KHET-VVAAKEVEFEMTPEQADACEARGDTPELWFC-RD--LKGYAWVFRKG-NFLNIGL
T_halophila_tmpA  (SEQ ID NO:24)              SSET-AVHAQEIEFEMTFEQAAACPVEADVFELYFL-RD--LSGYGWIVRKG-DWLNIGL
H_ochraceum_tmpA  (SEQ ID NO:34)              KMET-AITAKEVEFEMNAEQAAHCKVREDTPELWFC-RD--LKGYAWVERKG-DYLNIGL
M_aquaeolei_tmpA  (SEQ ID NO:36)              KHET-VVAAKEVEFEMTFEQARACEARGDTPELWFC-RD--LKGYAWVFRKG-SYLNIGL
Archaeoglobus_fulgidus_AF0464
                  (SEQ ID NO:46)              KINEV---ESCAQVLMT----GLDIDSVTVFYIGRBLAPGGYAWIFKKGMGSANVGI
                                                 :     :                              :  *  * .   *  ***:

* = Conserved in TmpB sequences, but not in E. coli CtA sequence
*  = Single, fully conserved residue in all sequences
:  = Amino acids with strongly similar properties
.  = Amino acids with weakly similar properties
```

FIG. 8B

```
D_curvatus_tmpA(SEQ ID NO:26)            ------------------------LPK---ILLED------------------------
D_phenolica_tmpA(SEQ ID NO:28)           ------------------------LPG---MIFQNKRSL----NDEF------------
D_toluolica_tmpA(SEQ ID NO:30)           ------------------------LPG---MIFQNKRSH----KEFF------------
D_balticum_tmpA(SEQ ID NO:20)            ------------------------LPG---LVKSGERSA--------------------
D_postgatei_tmpA(SEQ ID NO:32)           ------------------------LPK---ILLEH------------------------
M_hydrocarbonclasticus_tmpA(SEQ ID NO:22) FGNRASEQ-AAGWELPE---WLKQPVASTLMRSHWFTRK----VV------TEKWFLHQ
T_halophila_tmpA(SEQ ID NO:24)           FGKGSAAG----------BPG---PVKDALARPLMASSWFARH----VI------LDRWFLHR
H_ochraceum_tmpA(SEQ ID NO:34)           FGVRASEAKDSGIVLED---WAKLKAAPLMRSHWFTRR----VV------TEKWFLHQ
M_aquaeolei_tmpA(SEQ ID NO:36)           FGTRATDQ-QPGFEVFB---WLKQPIASTLMRSHWFTRK----VV------TEKWFLHQ
Archaeoglobus_fulgidus_AF0464
 (SEQ ID NO:46)                          FGKKLRRNKKLQLKFIMDDALINKLLAGAIAGKNLREMSVAAIVKELLKAHPKLLWDLKD D_curvatus_tmpA(SEQ ID NO:26)            ------------
D_phenolica_tmpA(SEQ ID NO:28)           ------------
D_toluolica_tmpA(SEQ ID NO:30)           ------------
D_balticum_tmpA(SEQ ID NO:20)            ------------
D_postgatei_tmpA(SEQ ID NO:32)           ------------
M_hydrocarbonclasticus_tmpA(SEQ ID NO:22) DVPTLRAVG
T_halophila_tmpA(SEQ ID NO:24)           HQAPLAPAA
H_ochraceum_tmpA(SEQ ID NO:34)           QVPPLRAS-
M_aquaeolei_tmpA(SEQ ID NO:36)           EVPPLEVAV
Archaeoglobus_fulgidus_AF0464
 (SEQ ID NO:46)                          LF-------
```

^ = Conserved in TmpB sequences, but not in E. coli Cfa sequence
* = Single, fully conserved residue in all sequences
: = Amino acids with strongly similar properties
. = Amino acids with weakly similar properties

FIG. 8D

HETEROLOGOUS PRODUCTION OF 10-METHYLSTEARIC ACID BY CELLS EXPRESSING RECOMBINANT METHYLTRANSFERASE

CROSS REFERENCE TO RELATED APPLICATIONS

This application is a National Phase Application under 35 U.S.C. § 371 of International Application No. PCT/US2018/051919, filed Sep. 20, 2018, which claims the benefit of priority to U.S. Provisional Patent Application Ser. No. 62/561,136 filed Sep. 20, 2017, each of which are hereby incorporated by reference in their entirety.

This application is related to U.S. Ser. No. 15/710,734 and PCT/US17/52491 both filed Sep. 20, 2017.

SEQUENCE LISTING

The instant application contains a Sequence Listing which has been filed electronically in ASCII format and is hereby incorporated by reference in its entirety. Said ASCII copy, created on Sep. 20, 2018, is named novgp0006wo_sequencelisting.txt and is 124,309 bytes in size.

BACKGROUND OF THE INVENTION

A. Field of the Invention

The invention generally concerns production of branched (methyl)lipids by cells expressing recombinant methyltransferases and/or reductases derived from Gammaproteobacteria.

B. Description of Related Art

Fatty acids derived from agricultural plant and animal oils find use as industrial lubricants, hydraulic fluids, greases, and other specialty fluids in addition to oleochemical feedstocks for processing. The physical and chemical properties of these fatty acids result in large part from their carbon chain length and number of unsaturated double bonds. Fatty acids are typically 16:0 (sixteen carbons, zero double bonds), 16:1 (sixteen carbons, 1 double bond), 18:0, 18:1, 18:2, or 18:3. Importantly, fatty acids with no double bonds (saturated) have high oxidative stability, but they solidify at low temperature. Double bonds improve low-temperature fluidity, but decrease oxidative stability. This trade-off poses challenges for lubricant and other specialty-fluid formulations because consistent long term performance (high oxidative stability) over a wide range of operating temperatures is desirable. High 18:1 (oleic) fatty acid oils provide low temperature fluidity with relatively good oxidative stability. Accordingly, several commercial products, such as high oleic soybean oil, high oleic sunflower oil, and high oleic algal oil, have been developed with high oleic compositions. Oleic acid is an alkene, however, and subject to oxidative degradation.

A superior alternative is the addition of a fully saturated methyl branch to the fatty acid chain. This creates a similar melting-temperature depression as a double bond, but with no decrease in oxidative stability versus fully saturated linear fatty acids. Methyl branches located near the middle of the fatty acid chain have the largest melting-temperature depression. Several chemical processes have been explored to introduce methyl branches; however, the preferred industrial method results in random placement of the methyl branch and creates a substantial amount of by-product. There remains a need for efficient and economical processes of producing branched (methyl)lipids.

SUMMARY OF THE INVENTION

Disclosed herein are cells, nucleic acids, and proteins that can be used to produce branched (methyl) lipids, such as 10-methylstearic acids, and compositions that include such lipids. Saturated branched (methyl)lipids produced using embodiments of the present invention have favorable low-temperature fluidity and favorable oxidative stability, which are desirable properties for lubricants and specialty fluids.

Various aspects relate to nucleic acids comprising a recombinant tmpB gene encoding a methyltransferase protein and/or a recombinant tmpA gene encoding a reductase protein. The methyltransferase protein and/or reductase protein may be proteins expressed by species of the class Gammaproteobacteria (phylum, Proteobacteria), and the recombinant tmpB gene and/or recombinant tmpA gene may be codon-optimized for expression in a different phylum of bacteria or in eukaryotes (e.g., yeast, such as *Arxula adeninivorans* (also known as *Blastobotrys adeninivorans* or *Trichosporon adeninivorans*), *Saccharomyces cerevisiae*, or *Yarrowia lipolytica*). The recombinant tmpB gene or recombinant tmpA gene may be operably-linked to a promoter capable of driving expression in a phylum of bacteria other than Gammaproteobacteria or in eukaryotes (e.g., yeast). The nucleic acid may be a plasmid or a chromosome.

Some aspects relate to a cell comprising a nucleic acid as described herein. The cell may comprise a branched (methyl)lipid, such as 10-methylstearic acid, and/or an exomethylene-substituted lipid, such as 10-methylenestearic acid. The cell may be a eukaryotic cell, such as an algae cell, yeast cell, or plant cell.

Some aspects relate to a composition produced by cultivating a cell culture comprising cells as described herein. The oil composition may comprise a branched (methyl)lipid, such as 10-methylstearic acid, and/or an exomethylene-substituted lipid, such as 10-methylenestearic acid. In some embodiments, the oil composition is produced by cultivating a cell culture and recovering the oil composition from the cell culture, wherein the oil composition comprises 10-methyl fatty acids, and wherein the 10-methyl fatty acids comprise at least about 1% by weight of the total fatty acids in the oil composition. In some embodiments, the 20-methyl fatty acids comprise at least about 15% by weight of the total fatty acids in the oil composition.

Some aspects relate to a method of producing an oil composition, the method comprising: cultivating a cell culture comprising any of the cells disclosed herein; and recovering the oil composition from the cell culture. In some embodiments, the method further comprises contacting the cell culture with a substrate comprising a fatty acid from 14 to 18 carbons long with a double bond in the Δ9, Δ10, or Δ11 position. In some embodiments, recovering the oil composition from the cell culture comprises recovering lipids that have been secreted by the cell. In some embodiments, producing the oil composition comprises performing chemical reactions or causing chemical reactions to be performed in which oleic acid and methionine substrates are converted to 10-methylenestearic acid, wherein the chemical reactions are catalyzed by a tmpB protein. In some embodiments, producing the oil composition comprises performing chemical reactions or causing chemical reactions to be performed in which 10-methylene stearic acid is reduced to 10-methylstearic acid, wherein the chemical reactions are catalyzed by tmpA protein. In some embodiments, the reduction is performed using NADPH, ferredoxin, flavodoxin, rubredoxin, cytochrome c, or combinations thereof as reducing agents. In any of the methods disclosed herein that involve reduction reactions any one of, or any combination of, NADPH, ferredoxin, flavodoxin, rubredoxin, and cytochrome c may be used.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

BRIEF DESCRIPTION OF THE DRAWINGS

FIG. 2 shows the occurrence of cyclopropane fatty acyl phospholipid synthase (cfa) homologs and 10-methylpalmitic acid (10Me16) in certain Gammaproteobacteria with sequenced genomes and observed lipid profiles.

FIG. 6 shows the fatty acid profile of *E. coli* Top10 cells with plasmids pNC1071, pNC1072, pNC1073, pNC1074, pNC1076, and pNC53 (empty control vector) grown in LB medium. Percentage values show the weight percent of the indicated fatty acid as a percentage of all fatty acids. 14:0=Myristic acid, 16:0=Palmitic acid, 16:1Δ9=palmitoleic acid, 16:0cyc=17Δ,cis-9,10-methylenehexadecanoic acid, 10-methylene 16:0=10-methylene hexadecenoic acid, 18:1Δ11=vaccenic acid, 18:0=stearic acid, SD=standard deviation.

FIGS. 7A-7D show a CLUSTAL OMEGA alignment of tmpB protein sequences encoded by the tmpB genes from *Desulfobacula balticum, Marinobacter hydrocarbonclasticus, Thiohalospira halophila, Desulfobacter curvatus, Desulfobacter phenolica, Desulfobacula toluolica, Desulfobacter postgatei, Halofilum ochraceum*, and *Marinobacter aquaeolei*, along with the cyclopropane fatty acid synthase (Cfa) enzyme from *Escherichia coli*.

FIGS. 8A-8D show a CLUSTAL OMEGA alignment tmpA protein sequences encoded by the tmpA genes from *Desulfobacula balticum, Marinobacter hydrocarbonclasticus, Thiohalospira halophila, Desulfobacter curvatus, Desulfobacter phenolica, Desulfobacula toluolica, Desulfobacter postgatei, Halofilum ochraceum*, and *Marinobacter aquaeolei*, along with the *Archaeoglobus fulgidus* geranylgeranyl reductase protein AF0464.

DETAILED DESCRIPTION OF THE INVENTION

A. Definitions

Figure 1:
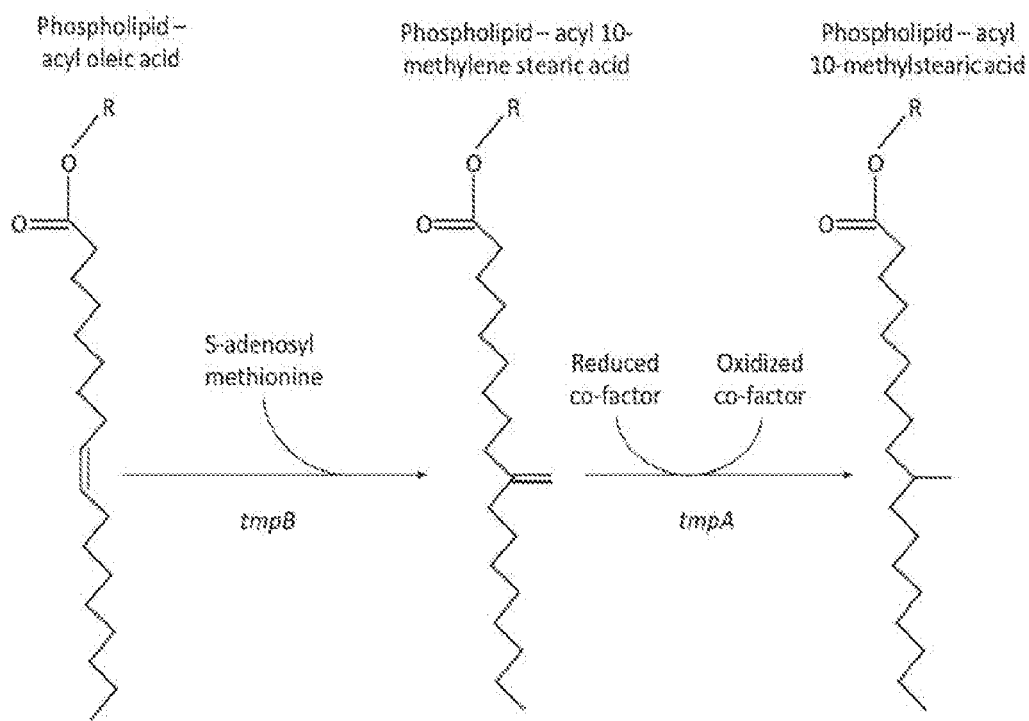
FIG. 1 depicts one possible mechanism for the conversion of oleic acid to 10-methylstearic acid. An oleic acid substrate may be present as an acyl chain of a glycerolipid or phospholipid. A methionine substrate, which donates the methyl group, may be present as S-adenosyl methionine. The oleic acid and methionine substrates may be converted to 10-methylenestearic acid (e.g., present as an acyl chain of a glycerolipid or phospholipid) and homocysteine (e.g., present as S-adenosyl homocysteine). This reaction may be catalyzed by a tmpB protein as described herein, infra. 10-methylenestearic acid (e.g., present as an acyl chain of a glycerolipid or phospholipid) may be reduced to 10-methylstearic acid. The reduction may be catalyzed by a tmpA protein as describe herein, infra, for example, without limitation, using NADPH as a reducing agent. Other examples of the reducing agent may include, without limitation, ferredoxin, flavodoxin, rubredoxin, cytochrome c, or combinations thereof. The language of the specification and claims, however, is not limited to any particular reaction mechanism.

The articles "a" and "an" are used herein to refer to one or to more than one (i.e., to at least one) of the grammatical object of the article. By way of example, "an element" means one element or more than one element.

The term "biologically-active portion" refers to an amino acid sequence that is less than a full-length amino acid sequence, but exhibits at least one activity of the full length sequence. For example, a biologically-active portion of a methyltransferase may refer to one or more domains of tmpB having biological activity for converting oleic acid (e.g., a phospholipid comprising an ester of oleate) and methionine (e.g., S-adenosyl methionine) into 10-methylenestearic acid (e.g., a phospholipid comprising an ester of 10-methylenestearate). A biologically-active portion of a reductase may refer to one or more domains of tmpA having biological activity for converting 10-methylenestearic acid (e.g., a phospholipid comprising an ester of 10-methylenestearate) and a reducing agent (e.g., ferrodoxin, flavodoxin, rubredoxin, cytochrome c, NADH, NADPH, FAD, $FADH_2$, $FMNH_2$) into 10-methylstearic acid (e.g., a phospholipid comprising an ester of 10-methylstearate). Biologically-active portions of a protein include peptides or polypeptides comprising amino acid sequences sufficiently identical to or derived from the amino acid sequence of the protein, e.g., the amino acid sequence set forth in SEQ ID NO:2, 4, 6, 8, 10, 12, 14, 16, 18, 20, 22, 24, 26, 28, 30, 32, 34, or 36, that include fewer amino acids than the full length protein, and exhibit at least one activity of the protein, especially methyltransferase or reductase activity. A biologically-active portion of a protein may comprise, comprise at least, or comprise at most, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or more amino acids, or any range derivable therein. Typically, biologically-active portions comprise a domain or motif having a catalytic activity, such as catalytic activity for producing 10-methylenestearic acid or 10-methylstearic acid. A biologically-active portion of a protein includes portions of the protein that have the same activity as the full-length peptide and every portion that has more activity than background. For example, a biologically-active portion of an enzyme may have, have at least, or have at most 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, 400% or higher activity relative to the full-length enzyme (or any range derivable therein). A biologically-active portion of a protein may include portions of a protein that lack a domain that targets the protein to a cellular compartment.

The terms "codon optimized" and "codon-optimized for the cell" refer to coding nucleotide sequences (e.g., genes) that have been altered to substitute at least one codon that is relatively rare in a desired host cell with a synonymous codon that is relatively prevalent in the host cell. Codon optimization thereby allows for better utilization of the tRNA of a host cell by matching the codons of a recombinant gene with the tRNA of the host cell. For example, the codon usage of the species of Gammaproteobacteria (prokaryotes) varies from the codon usage of yeast (eukaryotes). The translation efficiency in a yeast host cell of an mRNA encoding a Gammaproteobacteria protein may be increased by substituting the codons of the corresponding Gammaproteobacteria gene with codons that are more prevalent in the particular species of yeast. A codon optimized gene thereby has a nucleotide sequence that varies from a naturally-occurring gene.

The term "constitutive promoter" refers to a promoter that mediates the transcription of an operably linked gene independent of a particular stimulus (e.g., independent of the presence of a reagent such as isopropyl β-D-1-thiogalactopyranoside).

The term "DGAT1" refers to a gene that encodes a type 1 diacylglycerol acyltransferase protein, such as a gene that encodes a yeast DGAT2 protein.

The term "DGAT2" refers to a gene that encodes a type 2 diacylglycerol acyltransferase protein, such as a gene that encodes a yeast DGA1 protein.

"Diacylglyceride," "diacylglycerol," and "diglyceride," are esters comprised of glycerol and two fatty acids.

The terms "diacylglycerol acyltransferase" and "DGA" refer to any protein that catalyzes the formation of triacylglycerides from diacylglycerol. Diacylglycerol acyltransferases include type 1 diacylglycerol acyltransferases (DGA2), type 2 diacylglycerol acyltransferases (DGA1), and type 3 diacylglycerol acyltransferases (DGA3) and all homologs that catalyze the above-mentioned reaction.

The terms "diacylglycerol acyltransferase, type 1" and "type 1 diacylglycerol acyltransferases" refer to DGA2 and DGA2 orthologs.

The terms "diacylglycerol acyltransferase, type 2" and "type 2 diacylglycerol acyltransferases" refer to DGA1 and DGA1 orthologs.

The term "domain" refers to a part of the amino acid sequence of a protein that is able to fold into a stable three-dimensional structure independent of the rest of the protein.

The term "drug" refers to any molecule that inhibits cell growth or proliferation, thereby providing a selective advantage to cells that contain a gene that confers resistance to the drug. Drugs include antibiotics, antimicrobials, toxins, and pesticides.

"Dry weight" and "dry cell weight" mean weight determined in the relative absence of water. For example, reference to oleaginous cells as comprising a specified percentage of a particular component by dry cell weight means that the percentage is calculated based on the weight of the cell after substantially all water has been removed. The term "% dry weight," when referring to a specific fatty acid (e.g., oleic acid or 10-methylstearic acid), includes fatty acids that are present as carboxylates, esters, thioesters, and amides. For example, a cell that comprises 10-methylstearic acid as a percentage of total fatty acids by % dry cell weight includes 10-methylstearic acid, 10-methylstearate, the 10-methylstearate portion of a diacylglycerol comprising a 10-methylstearate ester, the 10-methylstearate portion of a triacylglycerol comprising a 10-methylstearate ester, the 10-methylstearate portion of a phospholipid comprising a 10-methylstearate ester, and the 10-methylstearate portion of 10-methylstearate CoA. The term "% dry weight," when referring to a specific type of fatty acid (e.g., C16 fatty acids, C18 fatty acids), includes fatty acids that are present as carboxylates, esters, thioesters, and amides as described above (e.g., for 10 methylstearic acid).

The term "gene," as used herein, may encompass genomic sequences that contain exons, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence. In other embodiments, the genes are synthesized, non-native cDNA wherein the codons have been optimized for expression in *Y. lipolytica* or *A. adeninivorans* based on codon usage. The term can further include nucleic acid molecules comprising upstream, downstream, and/or intron nucleotide sequences.

The term "inducible promoter" refers to a promoter that mediates the transcription of an operably linked gene in response to a particular stimulus.

The term "integrated" refers to a nucleic acid that is maintained in a cell as an insertion into the cell's genome, such as insertion into a chromosome, including insertions into a plastid genome.

"In operable linkage" and "operably linked" refer to a functional linkage between two nucleic acid sequences, such as a control sequence (typically a promoter) and the linked sequence (typically a sequence that encodes a protein, also called a coding sequence). A promoter is in operable linkage with a gene or is operably linked to a gene if it can mediate transcription of the gene.

The term "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "phospholipid" refers to esters comprising glycerol, two fatty acids, and a phosphate. The phosphate may be covalently linked to carbon-3 of the glycerol and comprise no further substitution, i.e., the phospholipid may be a phosphatidic acid. The phosphate may be substituted with ethanolamine (e.g., phosphatidylethanolamine), choline (e.g., phosphatidylcholine), serine (e.g., phosphatidylserine), inositol (e.g., phosphatidylinositol), inositol phosphate (e.g., phosphatidylinositol-3-phosphate, phosphatidylinositol-4-phosphate, phosphatidylinositol-5-phosphate), inositol bisphosphate (e.g., phosphatidylinositol-4,5-bisphosphate), or inositol triphosphate (e.g., phosphatidylinositol-3,4,5-bisphosphate).

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

A "promoter" is a nucleic acid control sequence that directs the transcription of a nucleic acid. As used herein, a promoter includes the necessary nucleic acid sequences near the start site of transcription.

The term "protein" refers to molecules that comprise an amino acid sequence, wherein the amino acids are linked by peptide bonds.

"Transformation" refers to the transfer of a nucleic acid into a host organism or into the genome of a host organism, resulting in genetically stable inheritance. Host organisms containing the transformed nucleic acid are referred to as "recombinant," "transgenic," or "transformed" organisms. Thus, nucleic acids of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The terms "triacylglyceride," "triacylglycerol," "triglyceride," and "TAG" are esters comprised of glycerol and three fatty acids.

The term "recombinant gene" refers to a gene that (1) is operatively linked to a polynucleotide to which it is not linked in nature or (2) has a nucleotide sequence different from the naturally-occurring nucleotide sequence, such as, for example, a non-naturally occurring mutation, a codon-optimized sequence, or a cDNA that lacks naturally-occurring introns that are found at the gene's genomic locus. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism is recombinant, if it is synthesized from an mRNA that is synthesized from a recombinant gene present in the cell. As other examples, a gene may be a recombinant gene if it is operably linked to a promoter different from the promoter to which it is operably linked in nature or if it is connected to another gene or portion thereof and, together with the other gene or portion thereof, encodes a protein that is not found in nature, such as a fusion protein or an epitope-tagged protein.

B. Microbe Engineering

1. Overview

Genes and gene products may be introduced into microbial host cells. Suitable host cells for expression of the genes and nucleic acid molecules are microbial hosts that can be found broadly within the fungal or bacterial families. Examples of suitable host strains include but are not limited to fungal or yeast species, such as *Arxula, Aspegillus, Aurantiochytrium, Candida, Claviceps, Cryptococcus, Cunninghamella, Hansenula, Kluyveromyces, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Yarrowia*, or bacterial species, such as members of proteobacteria and actinomycetes, as well as the genera *Acinetobacter, Arthrobacter, Brevibacterium, Acidovorax, Bacillus, Clostridia, Streptomyces, Escherichia, Salmonella, Pseudomonas*, and

*Cornyebacterium. Yarrowia lipolytica* and *Arxula adeninivorans* are suited for use as a host microorganism because they can accumulate a large percentage of their weight as triacylglycerols.

Microbial expression systems and expression vectors containing regulatory sequences that direct high level expression of foreign proteins are known to those skilled in the art. Any of these could be used to construct chimeric genes to produce any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and an aforementioned starting parent strain as a host can be transformed with the resulting plasmid. This approach can increase the copy number of each of the genes encoding the enzymes and, as a result, the activities of the enzymes can be increased. The plasmid is not particularly limited so long as it renders a desired genetic modification inheritable to the microorganism's progeny.

Vectors or cassettes useful for the transformation of suitable host cells are well known. Typically the vector or cassette contains sequences that direct the transcription and translation of the relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. In certain embodiments both control regions are derived from genes homologous to the transformed host cell, although it is to be understood that such control regions need not be derived from the genes native to the specific species chosen as a production host.

Promoters, cDNAs, and 3' UTRs, as well as other elements of the vectors, can be generated through cloning techniques using fragments isolated from native sources (see, e.g., Green & Sambrook, *Molecular Cloning: A Laboratory Manual*, (4th ed., 2012); U.S. Pat. No. 4,683,202 (incorporated by reference)). Alternatively, elements can be generated synthetically using known methods (see, e.g., Gene 164:49-53 (1995)).

2. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has many practical implications for what can be carried out at the molecular genetic level and is useful in the generation of a microbe that can produce a desired product. By its nature homologous recombination is a precise gene targeting event and, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements, such as promoters/UTRs, to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion, and exchanging gene expression regulatory elements such as promoters, enhancers and 3' UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

3. Vectors and Vector Components

Vectors for transforming microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

a. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in operable linkage with the coding sequence of interest, the coding sequence can be transformed into the cells such that it becomes operably linked to an endogenous promoter at the point of vector integration. The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, e.g., substantially, transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chen & Orozco, Nucleic Acids Research 16:8411 (1988)).

b. Genes and Codon Optimization

Typically, a gene includes a promoter, a coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA. Resources for codon-optimization of gene sequences are described in Puigbo et al., Nucleic Acids Research 35:W126-31 (2007), and principles underlying codon optimization strategies are described in Angov, Biotechnology Journal 6:650-69 (2011). Public databases providing statistics for codon usage by different organisms are available, including at www.kazusa.or.jp/codon/ and other publicly available databases and resources.

4. Transformation

Cells can be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of expression of transgenes in oleaginous yeast (e.g., *Yarrowia lipolytica*) can be found in the literature (Bordes et al., J. Microbiological Methods, 70:493 (2007); Chen et al., Applied Microbiology & Biotechnology 48:232 (1997)). Examples of expression of exogenous genes in bacteria such as *E. coli* are well known (Green & Sambrook, *Molecular Cloning: A Laboratory Manual*, (4th ed., 2012)).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

C. Exemplary Cells, Nucleic Acids, Compositions, and Methods

1. Transformed Cells

In some aspects, embodiments of the invention include cells transformed with one or more nucleic acids encoding a methyltransferase and/or reductase protein. In some embodiments, the transformed cell is a prokaryotic cell, such as a bacterial cell. In some embodiments, the cell is a eukaryotic cell, such as a mammalian cell, a yeast cell, a filamentous fungi cell, a protist cell, an algae cell, an avian cell, a plant cell, or an insect cell. In some embodiments, the cell is a yeast. Those with skill in the art will recognize that many forms of filamentous fungi produce yeast-like growth, and the definition of yeast herein encompasses such cells. The cell may cell may be selected from the group consisting of algae, bacteria, molds, fungi, plants, and yeasts. The cell may be a yeast, fungus, or yeast-like algae. The cell may be selected from thraustochytrids (*Aurantiochytrium*) and achlorophylic unicellular algae (*Prototheca*).

The cell may be selected from the group consisting of *Arxula, Aspegillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces,* and *Yarrowia.* It is specifically contemplated that one or more of these cell types may be excluded from embodiments of this invention.

The cell may be selected from the group of consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii,* and *Yarrowia lipolytica.* It is specifically contemplated that one or more of these cell types may be excluded from embodiments of this invention.

In certain embodiments, the transformed cell comprises about, at least about, or at most about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more lipid as measured by % dry cell weight, or any range derivable therein. In some embodiments, the transformed cell comprises C18 fatty acids at a concentration of about, at least about, or at most about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% as a percentage of total C16 and C18 fatty acids in the cell by weight, or any range derivable therein.

In some embodiments, the transformed cell comprises oleic acid at a concentration of about, at least about, or at most about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90% or higher as a percentage of total C16 and C18 fatty acids in the cell by weight, or any range derivable therein. In some embodiments, the transformed cell comprises 10-methylstearic acid at a concentration of about, at least about, or of at most about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, or higher as a percentage of total fatty acids in the cell by weight, or any range derivable therein.

A cell may be modified to increase its oleate content, which serves as a substrate for 10-methylstearate synthesis. Genetic modifications that increase oleate content are known (see, e.g., PCT Patent Application Publication No. WO16/094520, published Jun. 16, 2016, hereby incorporated by reference in its entirety). For example, a cell may comprise a Δ12 desaturase knockdown or knockout, which favors the accumulation of oleate and disfavors the production of linoleate. A cell may comprise a recombinant Δ9 desaturase gene, which favors the production of oleate and disfavors the accumulation of stearate. The recombinant Δ9 desaturase gene may be, for example, the Δ9 desaturase gene from *Y. lipolytica, Arxula adeninivorans,* or *Puccinia graminis.* A cell may comprise a recombinant elongase 1 gene, which favors the production of oleate and disfavors the accumulation of palmitate and palmitoleate. The recombinant elongase 1 gene may be the elongase 1 gene from *Y. lipolytica.* A cell may comprise a recombinant elongase 2 gene, which favors the production of oleate and disfavors the accumulation of palmitate and palmitoleate. The recombinant elongase 2 gene may be the elongase 2 gene from *R. norvegicus.*

A cell may be modified to increase its triacylglycerol content, thereby increasing its 10-methylstearate content. Genetic modifications that increase triacylglycerol content are known (see, e.g., PCT Patent Application Publication No. WO16/094520, published Jun. 16, 2016, hereby incorporated by reference in its entirety). A cell may comprise a recombinant diacylglycerol acyltransferase gene (e.g., DGAT1, DGAT2, or DGAT3), which favors the production of triacylglycerols and disfavors the accumulation of diacylglycerols. The recombinant diacylglycerol acyltransferase gene may be, for example, DGAT2 (encoding protein DGA1) from *Y. lipolytica,* DGAT1 (encoding protein DGAT2) from *C. purpurea,* or DGAT2 (encoding protein DGA1) from *R. toruloides.* The cell may comprise a glycerol-3-phosphate acyltransferase gene (Sct1) knockdown or knockout, which may favor the accumulation of triacylglycerols, depending on the cell type. The cell may comprise a recombinant glycerol-3-phosphate acyltransferase gene (Sct1) such as the Sct1 gene from *A. adeninivorans,* which may favor the accumulation of triacylglycerols. The cell may comprise a triacylglycerol lipase gene (TGL) knockdown or knockout, which may favor the accumulation of triacylglycerols in the cell.

Various aspects of the invention relate to a transformed cell. The transformed cell may comprise a recombinant methyltransferase gene (e.g., a tmpB gene), a recombinant reductase gene (e.g., a tmpA gene), an exomethylene-substituted lipid, and/or a branched (methyl)lipid. A branched (methyl)lipid may be a carboxylic acid (e.g., 10-methylstearic acid, 10-methylpalmitic acid, 12-methyloleic acid, 13-methyloleic acid, 10-methyl-octadec-12-enoic acid), carboxylate (e.g., 10-methylstearate, 10-methylpalmitate, 12-methyloleate, 13-methyloleate, 10-methyl-octadec-12-enoate), ester (e.g., diacylglycerol, triacylglycerol, phospholipid), thioester (e.g., 10-methylstearyl CoA, 10-methylpalmityl CoA, 12-methyloleoyl CoA, 13-methyloleoyl CoA, 10-methyl-octadec-12-enoyl CoA), or amide. An exomethylene-substituted lipid may be a carboxylic acid (e.g., 10-methylenestearic acid, 10-methylenepalmitic acid, 12-methyleneoleic acid, 13-methyleneoleic acid, 10-methylene-octadec-12-enoic acid), carboxylate (e.g., 10-methylenestearate, 10-methylenepalmitate, 12-methyleneoleate, 13-methyleneoleate, 10-methylene-octadec-12-enoate), ester (e.g., diacylglycerol, triacylglycerol, phospholipid), thioester (e.g., 10-methylenestearyl CoA, 10-methylenepalmityl CoA, 12-methyleneoleoyl CoA, 13-methyleneoleoyl CoA, 10-methylene-octadec-12-enoyl CoA), or amide. It is specifically contemplated that one or more of the above lipids may be excluded from embodiments of this invention. The methyltransferase gene and reductase gene may have the capability of together producing a methylated branch from any fatty acid from 14 to 18 carbons long with an unsaturated double bond in the Δ9, Δ10, or Δ11 position. The fatty acid may be 14, 15, 16, 17, or 18 carbons, or any range derivable therein.

"Fatty acids" generally exist in a cell as a phospholipid or triacylglycerol, although they may also exist as a monoacylglycerol or diacylglycerol, for example, as a metabolic intermediate. Free fatty acids also exist in the cell in equilibrium between a relatively abundant carboxylate anion and a relatively scarce, neutrally-charged acid. A fatty acid may exist in a cell as a thioester, especially as a thioester with coenzyme A (CoA), during biosynthesis or oxidation. A fatty acid may exist in a cell as an amide, for example, when covalently bound to a protein to anchor the protein to a membrane.

A cell may comprise any one of the nucleic acids described herein, infra (see, e.g., Section B, below). A cell may comprise multiple copies of any one of the nucleic acids described herein. This can be accomplished by, for example, including a tmpB and/or tmpB gene on a high-copy-number plasmid that is transformed into a cell.

A branched (methyl)lipid may comprise a saturated branched aliphatic chain (e.g., 10-methylstearic acid, 10-methylpalmitic acid) or an unsaturated branched aliphatic chain (e.g., 12-methyloleic acid, 13-methyloleic acid, 10-methyl-octadec-12-enoic acid). The branched (methyl)lipid may comprise a saturated or unsaturated branched aliphatic chain comprising a branching methyl group.

An exomethylene-substituted lipid may comprise a branched aliphatic chain (e.g., 10-methylenestearic acid, 10-methylenepalmitic acid, 12-methyleneoleic acid, 13-methyleneoleic acid, 10-methylene-octadec-12-enoic acid). The aliphatic chain may be branched because the aliphatic chain is substituted with an exomethylene group.

A branched (methyl)lipid may be 10-methylstearate, or an acid (10-methylstearic acid), ester (e.g., diacylglycerol, triacylglycerol, phospholipid), thioester (e.g., 10-methylstearyl CoA), or amide (e.g., 10-methylstearyl amide) thereof. For example, the branched (methyl)lipid may be a diacylglycerol, triacylglycerol, or phospholipid, and the diacylglycerol, triacylglycerol, or phospholipid may comprise an ester of 10-methylstearate.

An exomethylene-substituted lipid may be 10-methylenestearate, or an acid (10-methylenestearic acid), ester (e.g., diacylglycerol, triacylglycerol, phospholipid), thioester (e.g., 10-methylenestearyl CoA), or amide (e.g., 10-methylenestearyl amide) thereof. For example, the exomethylene-substituted lipid may be a diacylglycerol, triacylglycerol, or phospholipid, and the diacylglycerol, triacylglycerol, or phospholipid may comprise an ester of 10-methylenestearate.

In some embodiments, about, at least about, or at most about 1% of the fatty acids of the cell may be 10-methylstearic acid by weight. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids of the cell may be 10-methylstearic acid, or any range derivable therein.

In some embodiments, about, at least about, or at most about 1% of the fatty acids of the cell may be 10-methylenestearic acid by weight. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids of the cell may be 10-methylenestearic acid, or any range derivable therein.

In some embodiments, about, at least about, or at most about 1% by weight of the fatty acids of the cell may be one or more of the branched (methyl)lipids described herein. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids of the cell may be one or more of the branched (methyl)lipids described herein, or any range derivable therein.

In some embodiments, about, at least about, or at most about 1% by weight of the fatty acids of the cell may be one or more of the branched (methyl)lipids described herein. About, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids of the cell may one or more of the branched (methyl)lipids described herein, or any range derivable therein.

In some embodiments, the cell may comprise about, at least about, or at most about 1% 10-methylstearic acid as measured by % dry cell weight. The cell may comprise about, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% 10-methylstearic acid as measured by % dry cell weight, or any range derivable therein.

In some embodiments, the cell may comprise about, at least about, or at most about 1% 10-methylenestearic acid as measured by % dry cell weight. The cell may comprise about, at least about, or at most about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% 10-methylenestearic acid as measured by % dry cell weight, or any range derivable therein.

An unmodified cell of the same type (e.g., species) as a cell of the invention may not comprise 10-methylstearate, or an acid (10-methylstearic acid), ester (e.g., diacylglycerol, triacylglycerol, phospholipid), thioester (e.g., 10-methylstearyl CoA), or amide (e.g., 10-methylstearyl amide) thereof (e.g., wherein the unmodified cell does not comprise a recombinant methyltransferase gene or a recombinant reductase gene). An unmodified cell of the same type (e.g., species) as a cell of the invention may not comprise 10-methylenestearate, or an acid (10-methylenestearic acid), ester (e.g., diacylglycerol, triacylglycerol, phospholipid), thioester (e.g., 10-methylenestearyl CoA), or amide (e.g., 10-methylenestearyl amide) thereof (e.g., wherein the unmodified cell does not comprise a recombinant methyltransferase gene or a recombinant reductase gene). In some embodiments, an unmodified cell of the same species as the cell does not comprise a branched (methyl)lipid and/or an exomethylene-substituted lipid. In some embodiments, an unmodified cell of the same species as the cell does not comprise one or more of the branched (methyl)lipids or exomethylene-substituted lipids described herein.

In some embodiments, a cell may constitutively express the protein encoded by a recombinant methyltransferase gene and/or reductase gene. A cell may constitutively express a methyltransferase protein and/or reductase protein.

2. Nucleic Acids a. General

Various aspects of the invention relate to a nucleic acid comprising a recombinant methyltransferase gene, a recombinant reductase gene, or both. The nucleic acid may be, for example, a plasmid. In some embodiments, a recombinant methyltransferase gene and/or a recombinant reductase gene is integrated into the genome of a cell, and thus, the nucleic acid may be a chromosome. In some embodiments, the invention relates to a cell comprising a recombinant methyltransferase gene, e.g., wherein the recombinant methyltransferase gene is present in a plasmid or chromosome. In some embodiments, the invention relates to a cell comprising a recombinant reductase gene, e.g., wherein the recombinant reductase gene is present in a plasmid or chromosome. A recombinant methyltransferase gene and a recombinant reductase gene may be present in a cell in the same nucleic acid (e.g., same plasmid or chromosome) or in different nucleic acids (e.g., different plasmids or chromosomes).

A nucleic acid may be inheritable to the progeny of a transformed cell. A gene such as a recombinant methyltransferase gene or recombinant reductase gene may be inheritable because it resides on a plasmid or chromosome. In certain embodiments, a gene may be inheritable because it is integrated into the genome of the transformed cell.

A gene may comprise conservative substitutions, deletions, and/or insertions while still encoding a protein that has activity. For example, codons may be optimized for a particular host cell, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions.

Proteins may comprise conservative substitutions, deletions, and/or insertions while still maintaining activity. Conservative substitution tables are well known in the art (Creighton, *Proteins* (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus, when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

b. Nucleic Acids Comprising a Recombinant Methyltransferase Gene

A methyltransferase gene (e.g., a recombinant methyltransferase gene) encodes a methyltransferase protein, which is an enzyme capable of transferring a carbon atom and one or more protons bound thereto from a substrate such as S-adenosyl methionine to a fatty acid such as oleic acid (e.g., wherein the fatty acid is present as a free fatty acid, carboxylate, phospholipid, diacylglycerol, or triacylglycerol). The methyltransferase gene (e.g., a recombinant methyltransferase gene) may have a coding region that is identical to one from a bacterium of the class Gammaproteobacteria. The methyltransferase gene may comprise any one of the nucleotide sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17. The methyltransferase gene (e.g., a recombinant methyltransferase gene) may be a 10-methylstearic B gene (tmpB) as described herein, or a biologically-active portion thereof (i.e., wherein the biologically-active portion thereof comprises methyltransferase activity).

The methyltransferase gene (e.g., a recombinant methyltransferase gene) may be derived from a species of Gammaproteobacteria, such as bacteria from the genera *Desulfobacter, Desulfobacula, Marinobacter, Thiohalospira*, or *Halofilum*. The methyltransferase gene (e.g., a recombinant methyltransferase gene) may be selected from the group consisting of *Desulfobacula balticum* gene tmpB (SEQ ID NO:1), *Marinobacter hydrocarbonclasticus* gene tmpB (SEQ ID NO:3), *Thiohalospira halophila* gene tmpB (SEQ ID NO:5), *Desulfobacter curvatus* gene tmpB (SEQ ID NO:7), *Desulfobacter phenolica* gene tmpB (SEQ ID NO:9), *Desulfobacula toluolica* gene tmpB (SEQ ID NO:11), *Desulfobacter postgatei* gene tmpB (SEQ ID NO:13), *Halofilum ochraceum* gene tmpB (SEQ ID NO:15), and *Marinobacter aquaeolei* gene tmpB (SEQ ID NO:17). It is specifically contemplated that one or more of the above methyltransferase genes may be excluded from embodiments of this invention.

A recombinant methyltransferase gene may be recombinant because it is operably linked to a promoter other than the naturally-occurring promoter of the methyltransferase gene. Such genes may be useful to drive transcription in a particular species of cell. A recombinant methyltransferase gene may be recombinant because it contains one or more nucleotide substitutions relative to a naturally-occurring methyltransferase gene. Such genes may be useful to increase the translation efficiency of the methyltransferase gene's mRNA transcript in a particular species of cell.

A nucleic acid may comprise a recombinant methyltransferase gene and a promoter, wherein the recombinant methyltransferase gene and promoter are operably linked. The recombinant methyltransferase gene and promoter may be derived from different species. For example, the recombinant methyltransferase gene may encode the methyltransferase protein of a species of Gammaproteobacteria, and the recombinant methyltransferase gene may be operably-linked to a promoter that can drive transcription in another type of bacteria or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant methyltransferase gene, and the recombinant methyltransferase gene may be operably linked to a promoter capable of driving transcription of the recombinant methyltransferase gene in the cell. The cell may be a species of yeast, and the promoter may be a yeast promoter. The cell may be a species of bacteria, and the promoter may be a bacterial promoter (e.g., wherein the bacterial promoter is not a promoter from a Gammaproteobacterium). The cell may be a species of algae, and the promoter may be an algae promoter. The cell may be a species of plant, and the promoter may be a plant promoter.

A recombinant methyltransferase gene may be operably linked to a promoter that cannot drive transcription in the cell from which the recombinant methyltransferase gene originated. For example, the promoter may not be capable of binding an RNA polymerase of the cell from which a recombinant methyltransferase gene originated. In some embodiments, the promoter cannot bind a prokaryotic RNA polymerase and/or initiate transcription mediated by a prokaryotic RNA polymerase. In some embodiments, a recombinant methyltransferase gene is operably-linked to a promoter that cannot drive transcription in the cell from which the protein encoded by the gene originated. For example, the promoter may not be capable of binding an RNA polymerase of a cell that naturally expresses the methyltransferase enzyme encoded by a recombinant methyltransferase gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1α; Glycerol-3-phosphate dehydrogenase; Triosephosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/P$_i$ cotransporter; Pyruvate decarboxylase; Phytase; or Alpha-amylase, e.g., wherein the gene is a yeast gene, such as a gene from *Yarrowia lipolytica* or *Arxula adeninivorans*.

A recombinant methyltransferase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17. A recombinant methyltransferase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs of the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17. A recombinant methyltransferase may or may not have 100% sequence identity with any one of the nucleotide sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17. A recombinant methyltransferase gene may or may not have 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, or 1200 of the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17. A recombinant methyltransferase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17, and the recombinant methyltransferase gene may encode a methyltransferase protein with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18. For example, a gene that is codon-optimized for expression in yeast may have about 70% sequence identity with SEQ ID NO:1, while the protein encoded by such a codon-optimized gene may have 100% sequence identity with the amino acid sequence set forth in SEQ ID NO:2. Thus, even though a codon-optimized gene may have only about 70% sequence identity or less to the original gene, the codon-optimized gene encodes the same amino acid sequence of the original gene.

A recombinant methyltransferase gene may vary from a naturally-occurring methyltransferase gene because the recombinant methyltransferase gene may be codon-optimized for expression in a eukaryotic cell, such as a plant cell, algae cell, or yeast cell. A cell may comprise a recombinant methyltransferase gene, wherein the recombinant methyltransferase gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant methyltransferase gene may vary from a naturally-occurring methyltransferase gene or may be unchanged from a naturally-occurring methyltransferase gene. For example, a recombinant methyltransferase gene may comprise a nucleotide sequence with at least about 65% sequence identity with the naturally-occurring nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17 (e.g., at least about 70%, 75%, 80%, 85%, 90%, 95%, 96%, 97%, 98%, or 99% sequence identity), and at least 5 codons of the nucleotide sequence of the recombinant methyltransferase gene may vary from the naturally-occurring nucleotide sequence (e.g., at least about 10, 15, 20, 25, 30, 35, 40, 45, 50, 60, 70, 80, 90, or 100 codons).

A methyltransferase gene encodes a methyltransferase protein. A methyltransferase protein may be a protein expressed by a species of Gammaproteobacteria, such as bacteria from the genera *Desulfobacter*, *Desulfobacula*, *Marinobacter*, *Thiohalospira*, or *Halofilum*. A recombinant methyltransferase gene may encode a naturally-occurring methyltransferase protein even if the recombinant methyltransferase gene is not a naturally-occurring methyltransferase gene. For example, a recombinant methyltransferase gene may vary from a naturally-occurring methyltransferase gene because the recombinant methyltransferase gene is codon-optimized for expression in a specific cell. The codon-optimized, recombinant methyltransferase gene and the naturally-occurring methyltransferase gene may nevertheless encode the same naturally-occurring methyltransferase protein.

A recombinant methyltransferase gene may encode a methyltransferase protein selected from the group consisting of *Desulfobacula balticum* protein tmpB (SEQ ID NO:2), *Marinobacter hydrocarbonclasticus* protein tmpB (SEQ ID NO:4), *Thiohalospira halophila* protein tmpB (SEQ ID NO:6), *Desulfobacter curvatus* protein tmpB (SEQ ID NO:8), *Desulfobacter phenolica* protein tmpB (SEQ ID NO:10), *Desulfobacula toluolica* protein tmpB (SEQ ID NO:12), *Desulfobacter postgatei* protein tmpB (SEQ ID NO:14), *Halofilum ochraceum* protein tmpB (SEQ ID NO:16), and *Marinobacter aquaeolei* protein tmpB (SEQ ID NO:18). It is specifically contemplated that one or more of the above methyltransferase proteins may be excluded from embodiments of this invention. A recombinant methyltransferase gene may encode a methyltransferase protein, and the methyltransferase protein may be substantially identical to any one of the foregoing enzymes, but the recombinant methyltransferase gene may vary from the naturally-occurring gene that encodes the enzyme. The recombinant methyltransferase gene may vary from the naturally-occurring gene because the recombinant methyltransferase gene may be codon-optimized for expression in a specific phylum, class, order, family, genus, species, or strain of cell.

The sequences of naturally-occurring methyltransferase proteins are set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, and SEQ ID NO:18. A recombinant methyltransferase gene may or may not encode a protein comprising 100% sequence identity with the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18. For example, a recombinant methyltransferase gene may encode a protein having 100% sequence identity with a biologically-active portion of an amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

A recombinant methyltransferase gene may encode a methyltransferase protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% sequence identity with the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18, or a biologically-active portion thereof. A recombinant methyltransferase gene may encode a methyltransferase protein having about, at least about, or at most about 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, or 400% methyltransferase activity relative to a protein comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18. A recombinant methyltransferase gene may encode a protein having at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous amino acids starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

Substrates for the methyltransferase protein may include any fatty acid from 14 to 18 carbons long with an unsaturated double bond in the Δ9, Δ10, or Δ11 position. The substrate may have a chain that is 14, 15, 16, 17, or 18 carbons long, or any range derivable therein. The methyltransferase protein may be capable of catalyzing the formation of a methylene substitution at the Δ9, Δ10, or Δ11 position of such a substrate.

In some embodiments, the recombinant methyltransferase gene encodes a methyltransferase protein that has specific amino acids unchanged from the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18. The unchanged amino acids can include 1, 2, 3, 4, 5, 6, 7, 8, or 9 amino acids selected from Y163, T175, R199, E211, G269, Y271, N313, N319, and W389 of *Marinobacter hydrocarbonclasticus* tmpB or corresponding amino acids in tmpB from *Desulfobacula balticum, Thiohalospira halophila, Desulfobacter curvatus, Desulfobacter phenolica, Desulfobacula toluolica, Desulfobacter postgatei, Halofilum ochraceum,* or *Marinobacter aquaeolei,* according to the alignment set forth in FIGS. 7A-D.

c. Nucleic Acids Comprising a Recombinant Reductase Gene

A reductase gene (e.g., a recombinant reductase gene) encodes a reductase protein, which is an enzyme capable of reducing a double bond of a fatty acid (e.g., wherein the fatty acid is present as a free fatty acid, carboxylate, phospholipid, diacylglycerol, or triacylglycerol). The reductase gene (e.g., a recombinant reductase gene) may have a coding region that is identical to one from a bacterium of the class Gammaproteobacteria. The reductase gene may comprise any one of the nucleotide sequences set forth in SEQ ID NO:19, SEQ ID NO:21, SEQ ID NO:23, SEQ ID NO:25, SEQ ID NO:27, SEQ ID NO:29, SEQ ID NO:31, SEQ ID NO:33, and SEQ ID NO:35. The reductase gene (e.g., a recombinant reductase gene) may be a 10-methylstearic A gene (tmpA) as described herein, or a biologically-active portion thereof (i.e., wherein the biologically-active portion thereof comprises reductase activity).

The reductase gene (e.g., a recombinant reductase gene) may be derived from a species of Gammaproteobacteria, such as bacteria from the genera *Desulfobacter, Desulfobacula, Marinobacter, Thiohalospira,* or *Halofilum.* The reductase gene (e.g., a recombinant reductase gene) may be selected from the group consisting of *Desulfobacula balticum* gene tmpA (SEQ ID NO:19), *Marinobacter hydrocarbonclasticus* gene tmpA (SEQ ID NO:21), *Thiohalospira halophila* gene tmpA (SEQ ID NO:23), *Desulfobacter curvatus* gene tmpA (SEQ ID NO:25), *Desulfobacter phenolica* gene tmpA (SEQ ID NO:27), *Desulfobacula toluolica* gene tmpA (SEQ ID NO:29), *Desulfobacter postgatei* gene tmpA (SEQ ID NO:31), *Halofilum ochraceum* gene tmpA (SEQ ID NO:33), and *Marinobacter aquaeolei* gene tmpA (SEQ ID NO:35). It is specifically contemplated that one or more of the above reductase genes may be excluded from embodiments of this invention.

A recombinant reductase gene may be recombinant because it is operably linked to a promoter other than the naturally-occurring promoter of the reductase gene. Such genes may be useful to drive transcription in a particular species of cell. A recombinant reductase gene may be recombinant because it contains one or more nucleotide substitutions relative to a naturally-occurring reductase gene. Such genes may be useful to increase the translation efficiency of the reductase gene's mRNA transcript in a particular species of cell.

A nucleic acid may comprise a recombinant reductase gene and a promoter, wherein the recombinant reductase gene and promoter are operably linked. The recombinant reductase gene and promoter may be derived from different species. For example, the recombinant reductase gene may encode the reductase protein of a species of Gammaproteobacteria, and the recombinant reductase gene may be operably-linked to a promoter that can drive transcription in another type of bacteria or a eukaryote (e.g., an algae cell, yeast cell, or plant cell). The promoter may be a eukaryotic promoter. A cell may comprise the nucleic acid, and the promoter may be capable of driving transcription in the cell. A cell may comprise a recombinant reductase gene, and the recombinant reductase gene may be operably linked to a promoter capable of driving transcription of the recombinant reductase gene in the cell. The cell may be a species of yeast, and the promoter may be a yeast promoter. The cell may be a species of bacteria, and the promoter may be a bacterial promoter (e.g., wherein the bacterial promoter is not a promoter from a Gammaproteobacterium). The cell may be a species of algae, and the promoter may be an algae promoter. The cell may be a species of plant, and the promoter may be a plant promoter.

A recombinant reductase gene may be operably linked to a promoter that cannot drive transcription in the cell from which the recombinant reductase gene originated. For example, the promoter may not be capable of binding an RNA polymerase of the cell from which a recombinant reductase gene originated. In some embodiments, the promoter cannot bind a prokaryotic RNA polymerase and/or initiate transcription mediated by a prokaryotic RNA polymerase. In some embodiments, a recombinant reductase gene is operably-linked to a promoter that cannot drive transcription in the cell from which the protein encoded by the gene originated. For example, the promoter may not be capable of binding an RNA polymerase of a cell that naturally expresses the reductase enzyme encoded by a recombinant reductase gene.

A promoter may be an inducible promoter or a constitutive promoter. A promoter may be any one of the promoters described in PCT Patent Application Publication No. WO 2016/014900, published Jan. 28, 2016 (hereby incorporated by reference in its entirety). WO 2016/014900 describes various promoters derived from yeast species *Yarrowia lipolytica* and *Arxula adeninivorans*, which may be particularly useful as promoters for driving the transcription of a recombinant gene in a yeast cell. A promoter may be a promoter from a gene encoding a Translation Elongation factor EF-1α; Glycerol-3-phosphate dehydrogenase; Triosephosphate isomerase 1; Fructose-1,6-bisphosphate aldolase; Phosphoglycerate mutase; Pyruvate kinase; Export protein EXP1; Ribosomal protein S7; Alcohol dehydrogenase; Phosphoglycerate kinase; Hexose Transporter; General amino acid permease; Serine protease; Isocitrate lyase; Acyl-CoA oxidase; ATP-sulfurylase; Hexokinase; 3-phosphoglycerate dehydrogenase; Pyruvate Dehydrogenase Alpha subunit; Pyruvate Dehydrogenase Beta subunit; Aconitase; Enolase; Actin; Multidrug resistance protein (ABC-transporter); Ubiquitin; GTPase; Plasma membrane Na+/P$_i$ cotransporter; Pyruvate decarboxylase; Phytase; or Alpha-amylase, e.g., wherein the gene is a yeast gene, such as a gene from *Yarrowia lipolytica* or *Arxula adeninivorans*.

A recombinant reductase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:19, SEQ ID NO:21, SEQ ID NO:23, SEQ ID NO:25, SEQ ID NO:27, SEQ ID NO:29, SEQ ID NO:31, SEQ ID NO:33, or SEQ ID NO:35. A recombinant reductase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200 of the nucleotide sequence set forth in SEQ ID NO:19, SEQ ID NO:21, SEQ ID NO:23, SEQ ID NO:25, SEQ ID NO:27, SEQ ID NO:29, SEQ ID NO:31, SEQ ID NO:33, or SEQ ID NO:35. A recombinant reductase may or may not have 100% sequence identity with any one of the nucleotide sequences set forth in SEQ ID NO:19, SEQ ID NO:21, SEQ ID NO:23, SEQ ID NO:25, SEQ ID NO:27, SEQ ID NO:29, SEQ ID NO:31, SEQ ID NO:33, and SEQ ID NO:35. A recombinant reductase gene may or may not have 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs of the nucleotide sequence set forth in SEQ ID NO:19, SEQ ID NO:21, SEQ ID NO:23, SEQ ID NO:25, SEQ ID NO:27, SEQ ID NO:29, SEQ ID NO:31, SEQ ID NO:33, or SEQ ID NO:35. A recombinant reductase gene may comprise a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:19, SEQ ID NO:21, SEQ ID NO:23, SEQ ID NO:25, SEQ ID NO:27, SEQ ID NO:29, SEQ ID NO:31, SEQ ID NO:33, or SEQ ID NO:35, and the recombinant reductase gene may encode a reductase protein with, with at least, or with at most 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the amino acid sequence set forth in SEQ ID NO:20, SEQ ID NO:22, SEQ ID NO:24, SEQ ID NO:26, SEQ ID NO:28, SEQ ID NO:30, SEQ ID NO:32, SEQ ID NO:34, or SEQ ID NO:36. For example, a gene that is codon-optimized for expression in yeast may have about 70% sequence identity with SEQ ID NO:19, while the protein encoded by such a codon-optimized gene may have 100% sequence identity with the amino acid sequence set forth in SEQ ID NO:20. Thus, even though a codon-optimized gene may have only about 70% sequence identity or less to the original gene, the codon-optimized gene encodes the same amino acid sequence of the original gene.

A recombinant reductase gene may vary from a naturally-occurring reductase gene because the recombinant reductase gene may be codon-optimized for expression in a eukaryotic cell, such as a plant cell, algae cell, or yeast cell. A cell may comprise a recombinant reductase gene, wherein the recombinant reductase gene is codon-optimized for the cell.

Exactly, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 codons of a recombinant reductase gene may vary from a naturally-occurring reductase gene or may be unchanged from a naturally-occurring reductase gene. For example, a recombinant reductase gene may comprise a nucleotide sequence with at least about 65% sequence identity with the naturally-occurring nucleotide sequence set forth in SEQ ID NO:19, SEQ ID NO:21, SEQ ID NO:23, SEQ ID NO:25, SEQ ID NO:27, SEQ ID NO:29, SEQ ID NO:31, SEQ ID NO:33, or SEQ ID NO:35 (e.g., at least about 70%, 75%, 80%, 85%, 90%, 95%, 96%, 97%, 98%, or 99% sequence identity), and at least 5 codons of the nucleotide sequence of the recombinant reductase gene may vary from the naturally-occurring nucleotide sequence (e.g., at least about 10, 15, 20, 25, 30, 35, 40, 45, 50, 60, 70, 80, 90, or 100 codons).

A reductase gene encodes a reductase protein. A reductase protein may be a protein expressed by a species of Gammaproteobacteria, such as bacteria from the genera *Desulfobacter, Desulfobacula, Marinobacter, Thiohalospira,* or *Halofilum*. A recombinant reductase gene may encode a naturally-occurring reductase protein even if the recombinant reductase gene is not a naturally-occurring reductase gene. For example, a recombinant reductase gene may vary from a naturally-occurring reductase gene because the recombinant reductase gene is codon-optimized for expression in a specific cell. The codon-optimized, recombinant reductase gene and the naturally-occurring reductase gene may nevertheless encode the same naturally-occurring reductase protein.

A recombinant reductase gene may encode a reductase protein selected from the group consisting of *Desulfobacula balticum* protein tmpA (SEQ ID NO:20), *Marinobacter hydrocarbonclasticus* protein tmpA (SEQ ID NO:22), *Thiohalospira halophila* protein tmpA (SEQ ID NO:24), *Desulfobacter curvatus* protein tmpA (SEQ ID NO:26), *Desulfobacter phenolica* protein tmpA (SEQ ID NO:28),

*Desulfobacula toluolica* protein tmpA (SEQ ID NO:30), *Desulfobacter postgatei* protein tmpA (SEQ ID NO:32), *Halofilum ochraceum* protein tmpA (SEQ ID NO:34), and *Marinobacter aquaeolei* protein tmpA (SEQ ID NO:36). It is specifically contemplated that one or more of the above reductase proteins may be excluded from embodiments of this invention. A recombinant reductase gene may encode a reductase protein, and the reductase protein may be substantially identical to any one of the foregoing enzymes, but the recombinant reductase gene may vary from the naturally-occurring gene that encodes the enzyme. The recombinant reductase gene may vary from the naturally-occurring gene because the recombinant reductase gene may be codon-optimized for expression in a specific phylum, class, order, family, genus, species, or strain of cell.

The sequences of naturally-occurring reductase proteins are set forth in SEQ ID NO:20, SEQ ID NO:22, SEQ ID NO:24, SEQ ID NO:26, SEQ ID NO:28, SEQ ID NO:30, SEQ ID NO:32, SEQ ID NO:34, and SEQ ID NO:36. A recombinant reductase gene may or may not encode a protein comprising 100% sequence identity with the amino acid sequence SEQ ID NO:30, SEQ ID NO:32, SEQ ID NO:34, or SEQ ID NO:36. For example, a recombinant reductase gene may encode a protein having 100% sequence identity with a biologically-active portion of an amino acid sequence set forth in SEQ ID NO:20, SEQ ID NO:22, SEQ ID NO:24, SEQ ID NO:26, SEQ ID NO:28, SEQ ID NO:30, SEQ ID NO:32, SEQ ID NO:34, or SEQ ID NO:36.

A recombinant reductase gene may encode a reductase protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the amino acid sequence set forth in SEQ ID NO:20, SEQ ID NO:22, SEQ ID NO:24, SEQ ID NO:26, SEQ ID NO:28, SEQ ID NO:30, SEQ ID NO:32, SEQ ID NO:34, or SEQ ID NO:36, or a biologically-active portion thereof. A recombinant reductase gene may encode a reductase protein having about, at least about, or at most about 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, or 400% reductase activity relative to a protein comprising the amino acid sequence set forth in SEQ ID NO:20, SEQ ID NO:22, SEQ ID NO:24, SEQ ID NO:26, SEQ ID NO:28, SEQ ID NO:30, SEQ ID NO:32, SEQ ID NO:34, or SEQ ID NO:36. A recombinant reductase gene may encode a protein having, having at least, or having at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous amino acids starting at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 of the amino acid sequence set forth in SEQ ID NO:20, SEQ ID NO:22, SEQ ID NO:24, SEQ ID NO:26, SEQ ID NO:28, SEQ ID NO:30, SEQ ID NO:32, SEQ ID NO:34, or SEQ ID NO:36.

Substrates for the reductase protein may include any fatty acid from 14 to 18 carbons long with a methylene substitution in the Δ9, Δ10, or Δ11 position. The substrate may be 14, 15, 16, 17, or 18 carbons long, or any range derivable therein. The reductase protein may be capable of catalyzing the reduction of a methylene-substituted fatty acid substrate to a (methyl)lipid. The reductase protein, together with a methyltransferase protein, may be capable of catalyzing the production of a methylated branch from any fatty acid from 14 to 18 carbons long with an unsaturated double bond in the Δ9, Δ10, or Δ11 position, including fatty acids that are 14, 15, 16, 17, or 18 carbons long, or any range derivable therein.

In some embodiments, the recombinant reductase gene encodes a reductase protein that has specific amino acids unchanged from the amino acid sequence set forth in SEQ ID NO:20, SEQ ID NO:22, SEQ ID NO:24, SEQ ID NO:26, SEQ ID NO:28, SEQ ID NO:30, SEQ ID NO:32, SEQ ID NO:34, or SEQ ID NO:36. The unchanged amino acids can include 1, 2, 3, 4, 5, 6, 7, 8, 9, 10, 11, 12, 13, 14, 15, 16, 17, 18, 19, 20, 21, 22, 23, 24, or 25 amino acids selected from 18, L22, F37, P38, R39, K41, G45, W46, P49, G144, C148, P149, E169, E171, L197, I212, C249, H250, Y252, I270, G275, L276, E283, A296, and A299 of *Marinobacter hydrocarbonclasticus* tmpA or corresponding amino acids in tmpA from *Desulfobacula balticum, Thiohalospira halophila, Desulfobacter curvatus, Desulfobacter phenolica, Desulfobacula toluolica, Desulfobacter postgatei, Halofi-*

*lum ochraceum*, or *Marinobacter aquaeolei*, according to the alignment set forth in FIGS. 8A-D.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

Any nucleic acid that is referred to herein as having a certain percent sequence identity to a sequence set forth in a SEQ ID NO, includes nucleic acids that have the certain percent sequence identity to the complement of the sequence set forth in the SEQ ID NO.

d. Nucleic Acids Comprising a Recombinant Methyltransferase Gene and a Recombinant Reductase Gene A nucleic acid may comprise both a recombinant methyltransferase gene and a recombinant reductase gene. The recombinant methyltransferase gene and the recombinant reductase gene may encode proteins from the same species or from different species.

A nucleic acid may comprise the nucleotide sequence of an expression vector comprising a tmp operon that includes both a methyltransferase gene and a reductase gene. Such vectors may include pNC1071 (SEQ ID NO:39), which includes a *Desulfobacter postgatei* tmp operon; pNC1072 (SEQ ID NO:40), which includes a *Desulfobacula balticum* tmp operon, pNC1073 (SEQ ID NO:41), which includes a *Desulfobacula toluolica* tmp operon; pNC1074 (SEQ ID NO:42), which includes a *Marinobacter hydrocarbonclasticus* tmp operon; and pNC1076 (SEQ ID NO:43), which includes a *Thiohalospira halophila* tmp operon.

In some embodiments, the nucleic acid encodes a fusion protein that includes both a methyltransferase and a reductase or fragments thereof. In the context of the present invention, "fusion protein" means a single protein molecule containing two or more distinct proteins or fragments thereof, covalently linked via peptide bond in a single peptide chain. In some embodiments, the fusion protein comprises enzymatically active domains from both a methyltransferase protein and a reductase protein. The nucleic acid may further encode a linker peptide between the methyltransferase and the reductase. In some embodiments, the linker peptide comprises the amino acid sequence AGGAEGGNGGA (SEQ ID NO:44). The linker may comprise about or at least about 2, 3, 4, 5, 6, 7, 8, 9, 10, 15, 20, 25, or 30 amino acids, or any range derivable therein. The nucleic acid may comprise any of the methyltransferase and reductase genes described herein, and the fusion protein encoded by the nucleic acid can comprise any of the methyltransferase and reductase proteins described herein, including biologically active fragments thereof. In some embodiments, the fusion protein is a tmpA-B protein, in which the tmpA protein is closer to the N-terminus than the tmpB protein.

3. Compositions

Various aspects of the invention relate to compositions produced by the cells described herein. The composition may be an oil composition comprised of about, at least about, or at most about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% lipids by weight. The composition may comprise branched (methyl)lipids and/or exomethylene-substituted lipids. The branched (methyl)lipid may be a carboxylic acid (e.g., 10-methylstearic acid, 10-methylpalmitic acid, 12-methyloleic acid, 13-methyloleic acid, 10-methyl-octadec-12-enoic acid), carboxylate (e.g., 10-methylstearate, 10-methylpalmitate, 12-methyloleate, 13-methyloleate, 10-methyl-octadec-12-enoate), ester (e.g., diacylglycerol, triacylglycerol, phospholipid), thioester (e.g., 10-methylstearyl CoA, 10-methylpalmityl CoA, 12-methyloleoyl CoA, 13-methyloleoyl CoA, 10-methyl-octadec-12-enoyl CoA), or amide. The exomethylene-substituted lipid may be a carboxylic acid (e.g., 10-methylenestearic acid, 10-methylenepalmitic acid, 12-methyleneoleic acid, 13-methyleneoleic acid, 10-methylene-octadec-12-enoic acid), carboxylate (e.g., 10-methylenestearate, 10-methylenepalmitate, 12-methyleneoleate, 13-methyleneoleate, 10-methylene-octadec-12-enoate), ester (e.g., diacylglycerol, triacylglycerol, phospholipid), thioester (e.g., 10-methylenestearyl CoA, 10-methylenepalmityl CoA, 12-methyleneoleoyl CoA, 13-methyleneoleoyl CoA, 10-methylene-octadec-12-enoyl CoA), or amide. 10-methyl lipids, 10-methylene lipids, or both. It is specifically contemplated that one or more of the above lipids may be excluded from certain embodiments.

In some aspects, the composition is produced by cultivating a culture comprising any of the cells described herein and recovering the oil composition from the cell culture. The cells in the culture may contain any of the recombinant methyltransferase genes described herein and/or any of the recombinant reductase genes described herein. The culture medium and conditions can be chosen based on the species of the cell to be cultured and can be optimized to provide for maximal production of the desired lipid profile.

Various methods are known for recovering an oil composition from a culture of cells. For example, lipids, lipid derivatives, and hydrocarbons can be extracted with a hydrophobic solvent such as hexane. Lipids and lipid derivatives can also be extracted using liquefaction, oil liquefaction, and supercritical $CO_2$ extraction. The recovery process may include harvesting cultured cells, such as by filtration or centrifugation, lysing cells to create a lysate, and extracting the lipid/hydrocarbon components using a hydrophobic solvent.

In addition to accumulating within cells, the lipids described herein may be secreted by the cells. In that case, a process for recovering the lipid may not require creating a lysate from the cells, but collecting the secreted lipid from the culture medium. Thus, the compositions described herein may be made by culturing a cell that secretes one of the lipids described herein, such as a linear fatty acid with a chain length of 14-18 carbons with a methyl branch at the Δ9, Δ10, or Δ11 position.

In some embodiments, the oil composition comprises about, at least about, or at most about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of a branched (methyl)lipid, such as a 10-methyl fatty acid, or any range derivable therein. In some embodiments, 10-methyl fatty acids comprise about, at least about, or at most about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the fatty acids in the composition, or any range derivable therein.

The amount of 10-methyl fatty acids in a cell can be optimized by various methods. For example, increasing the expression of tmpA and/or tmpB can increase the methyltransferase and/or reductase activity within the cell, which may lead to accumulation of greater amounts of branched (methyl lipids). One way this can be accomplished is by increasing the number of copies of the gene in the cell, such as by including the genes on high-copy-number plasmids. Additionally or alternatively, the tmpA and/or tmpB cells can be operably linked to a promoter that drives high levels of expression.

4. Methods of Producing Branched (Methyl)Lipid

Various aspects of the invention relate to a method of producing a branched (methyl)lipid. The method may comprise incubating a cell or plurality of cells as described herein, supra, with media. The media may optionally be supplemented with an unbranched, unsaturated fatty acid, such as oleic acid, that serves as a substrate for methylation. The substrate may include one or more fatty acids from 14 to 18 carbons long with a double bond in the Δ9, Δ10, or Δ11 position. The substrate may be 14, 15, 16, 17, or 18 carbons long, or any range derivable therein. The media may optionally be supplemented with methionine or s-adenosyl methionine, which may similarly serve as a substrate. Thus, the method may comprise contacting a cell or plurality of cells with oleic acid (or some other substrate to be methylated), methionine, or both. The method may comprise incubating a cell or plurality of cells as described herein, supra, in a bioreactor. The method may comprise recovering lipids from the cells, such as by extraction with an organic solvent.

The method may comprise degumming the cell or plurality of cells, e.g., to remove proteins. The method may comprise transesterification or esterification of the lipids of the cells. An alcohol such as methanol or ethanol may be used for transesterification or esterification, e.g., thereby producing a fatty acid methyl ester or fatty acid ethyl ester.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Identification of tmpB and tmpA Genes in Gammaproteobacteria

Select Gammaproteobacteria are known to produce branched 10-methyl fatty acids. The acetate-oxidizing, sulfate-reducing *Desulfobacter* bacteria were reported to produce 10-methylhexadecanoic acid at 6%-24% of total phospholipid-ester linked fatty acid content (Dowling, Microbiology 132:1815-25 (1986)). Other reports of 10-methyl branched fatty acid production exist for bacteria in the Genus *Marinobacter* (Márquez, J. Syst. Evol. Microbiol. 55:1349-51 (2005); Huu, Int. J. Syst. Evol. Microbiol. 49:367-75 (1999); Gauthier, Int. J. Syst. Evol. Microbiol. 42:568-76 (1992); *Thiohalospira* (Sorokin, Int. J. Syst. Evol. Microbiol., 58:2890-97 (2008)), *Thiohalorhabdus* (Sorokin, Int. J. Syst. Evol. Microbiol. 58:2890-97 (2008)), *Desulfobacula*, and *Desulfotignum* (Kuever, Int. J. Syst. Evol. Microbiol. 51:171-77 (2001)). However, no genes or enzymes involved in Gammaproteobacteria 10-methyl fatty acid production have been described. In this Example, a pair of phylogenetically and sequence-homology distinct genes present in certain Gammaproteobacteria which direct production of 10-methyl fatty acids in heterologous hosts are described.

A list of Gammaproteobacteria that produce 10-methyl fatty acids and have sequenced genomes was compiled from literature reports. Additionally, representative Gammaproteobacteria that are not reported to produce 10-methyl fatty acids were included for comparison. According to a biochemical study on the unrelated bacterium *Mycobacterium phlei* using unpurified enzyme preparations, the first step of 10-methyl fatty acid synthesis occurs via a mechanism similar to cyclopropane fatty acid synthesis and is followed by an enzymatic reduction step (Akamatsu, J. Biol. Chem. 245:701-08 (1970)). To find gene candidates responsible for 10-methyl fatty acid production the Gammaproteobacteria genomes were scanned for homologs of *E. coli* cyclopropane fatty acyl phospholipid synthase (cfa), which is responsible for methylation of unsaturated fatty acids to produce cyclopropane fatty acids (Wang, Biochemistry 31:11020-28 (1992); Taylor, Biochemistry 18:3292-3300 (1979)). This was performed using the NCBI BLAST protein analysis tool and the BioCyc genomic database (Caspi, Nucleic Acids Res. 40:D742-53 (2016)). Next, the cfa homologs were scanned for adjacent genes in an operon structure that had homology to an oxidoreductase or electron transfer function. Interestingly, Gammaproteobacteria able to produce 10-methyl fatty acids all possessed a gene operon (referred to herein as the tmp operon) with a cyclopropane fatty acid synthase gene homolog (referred to herein as tmpB) and a gene with homology to a geranylgeranyl reductase (referred to herein as tmpA). These results are summarized in FIG. 2. It is unlikely tmpA is a true geranylgeranyl reductase since the enzyme is involved in chlorophyll and tocopherol biosynthesis, neither of which chemicals the bacteria produce.

Example 2

E. coli Expression of the tmpB and tmpA Gene Products

Figure 3A:
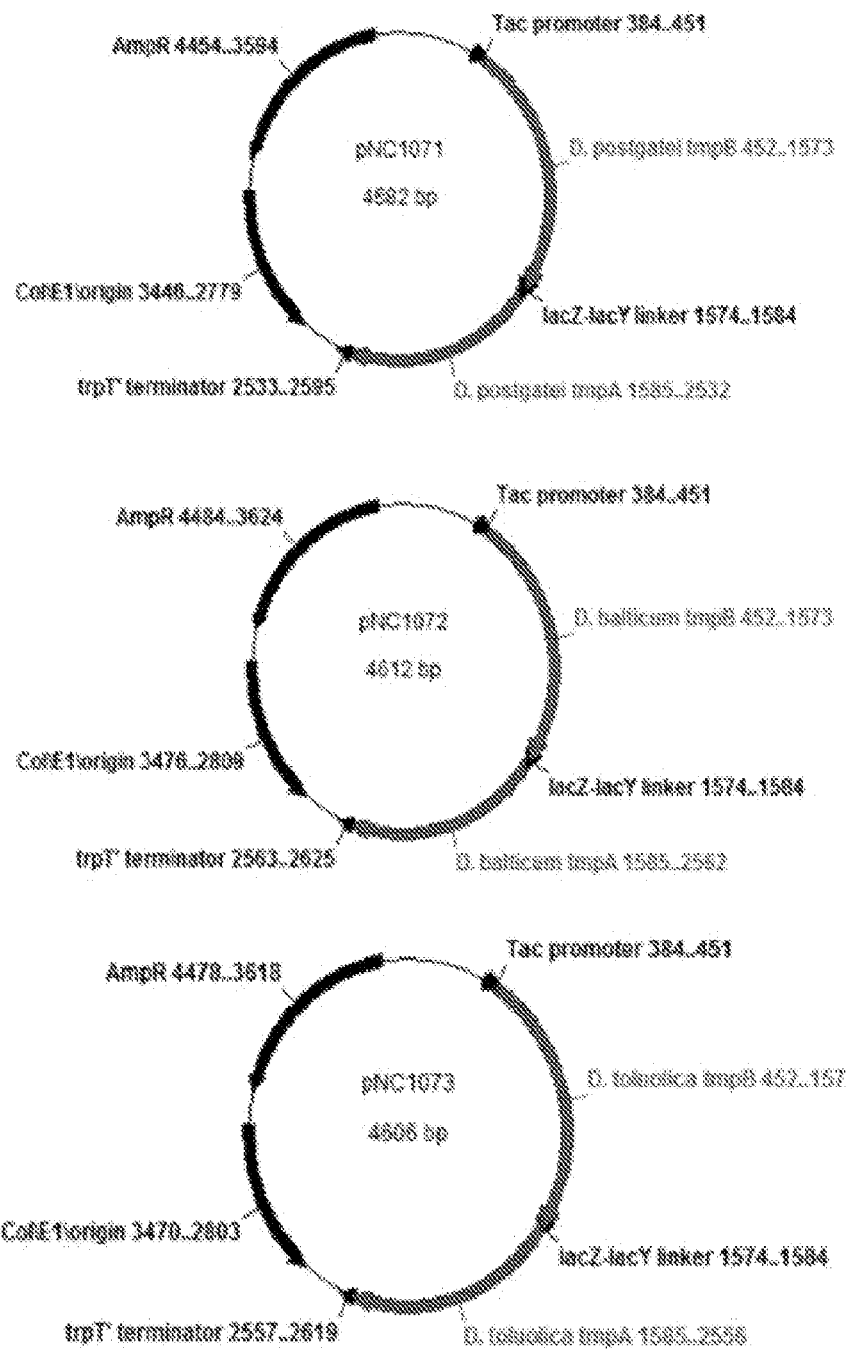
FIGS. 3A-3B depict maps of the following vectors, which encode a tmp operon: pNC1071 (SEQ ID NO:39), which includes a *Desulfobacter postgatei* tmp operon; pNC1072 (SEQ ID NO:40), which includes a *Desulfobacula balticum* tmp operon, pNC1073 (SEQ ID NO:41), which includes a *Desulfobacula toluolica* tmp operon; pNC1074 (SEQ ID NO:42), which includes a *Marinobacter hydrocarbonclasticus* tmp operon; and pNC1076 (SEQ ID NO:43), which includes a *Thiohalospira halophila* tmp operon.
Figure 3B:
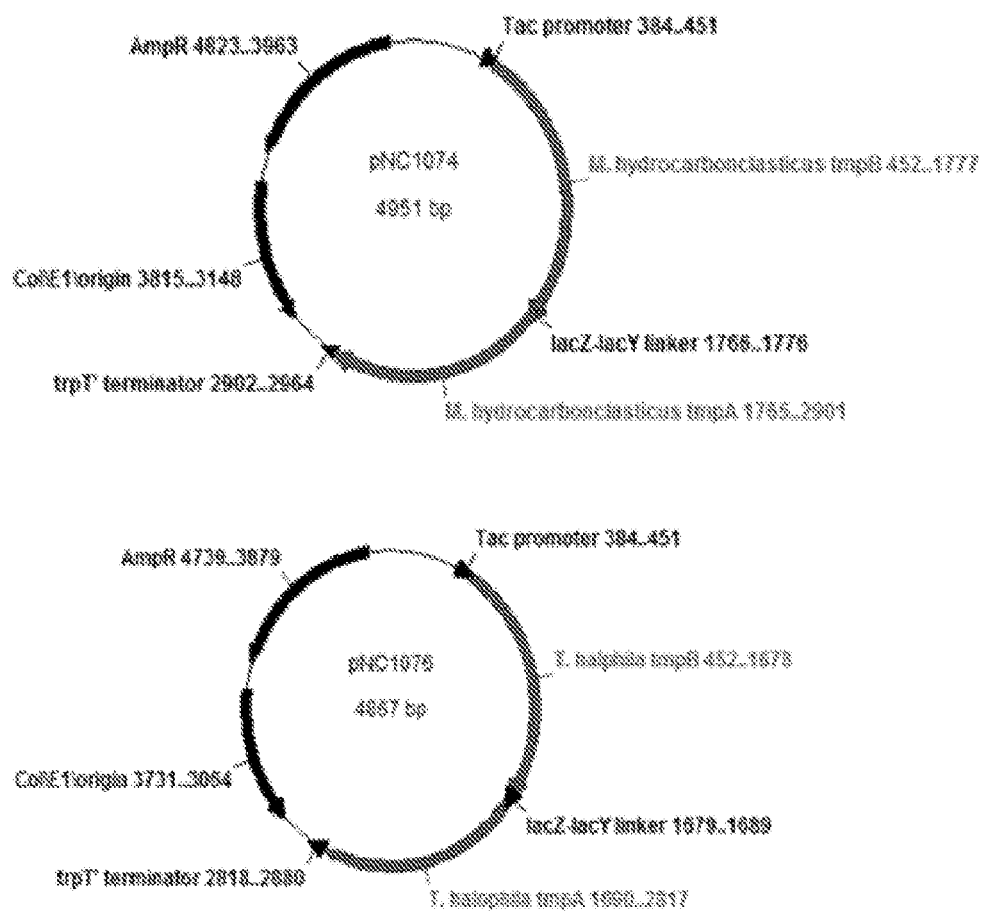

To test if the tmp gene operon was responsible for Gammaproteobacteria 10-methyl fatty acid production, the genes were designed in an *E. coli* expression vector using the DNA manipulation software A Plasmid Editor and synthesized by Thermofisher Scientific-GeneArt. The native codon usage of the tmp genes was not changed. tmpB gene transcription was controlled using the constitutively active tac promoter (de Boer 1983), followed by the *E. coli* lacZ-lacY intergene linker region, the tmpA gene, and the trpT' gene terminator (Wu 1981). These synthetic gene operons were cloned into an *E. coli* expression vector containing the AmpR ampicillin resistance gene and the ColE1 origin of replication (FIG. 3A-3B). The plasmid vectors are named pNC1071 (SEQ ID NO:39), which includes the *Desulfobacter postgatei* tmp operon; pNC1072 (SEQ ID NO:40), which includes the *Desulfobacula balticum* tmp operon; pNC1073 (SEQ ID NO:41), which includes the *Desulfobacula toluolica* tmp operon; pNC1074 (SEQ ID NO:42), which includes the *Marinobacter hydrocarbonclasticus* tmp operon; and pNC1076 (SEQ ID NO:43), which includes the *Thiohalospira halophila* tmp operon.

Plasmids pNC1071, pNC1072, pNC1073, pNC1074, pNC1076, and the control plasmid pNC53 containing the AmpR gene, ColE1 origin, and tac promoter were transformed into *E. coli* Top10 (Invitrogen) using a standard electrotransformation protocol utilizing 50 μL suspended cells, 1 μL of plasmid DNA at a concentration of 200 ng per μL, a 1 mm gap electrotransformation cuvette, and a pulse with 1.8 kV voltage, 200Ω, and 25 μF with exponential decay and a time constant of approximately 4.5 milliseconds. During the protocol cells were kept on ice and the cuvette was pre-chilled before pulsing with a Bio-Rad Gene Pulser Electroporation System. After pulsing, cells were transferred to 1 mL SOC medium and incubated at 37° C. for 1 hour before plating on LB agar containing 100 μg per mL ampicillin antibiotic.

Single colonies from the transformation plates were chosen and grown in 5 mL LB liquid media in 14 mL plastic falcon tubes overnight at 37° C. These were used to prepare freezer vials with 0.75 mL culture broth and 0.75 mL of 50% glycerol/water which were stored at −80° C.

Fermentation studies were performed in 50 mL LB media with 100 μg per mL ampicillin in 250 mL baffled shake flasks. 10 μL of frozen culture stock was added to the media and the flask was incubated at 37° C. and shaken at 200 rpm in a New Brunswick orbital incubator for 24 hours. Cell were harvested by centrifugation at 4000 rpm for 15 minutes in an Eppendorf 5810 R clinical centrifuge, resuspended in 0.5 mL deionized water, and frozen at −80° C.

FIG. 6 shows that *E. coli* transformed with pNC1071, pNC1073, pNC1074, and pNC1076, but not the empty vector control (pNC53) produced 10-methylene hexadecenoic acid.

To test the acyl chain substrate range for the tmpB and tmpA enzymes, *E. coli* transformed with pNC1074 (*M. hydrocarbonclausticus* tmp operon) or pNC1076 (*T. halophila* tmp operon) were grown in LB media supplemented with ampicillin and 100 mg/L of one of the fatty acids indicated in Table 1 below. After culturing, cells were harvested by centrifugation, washed with deionized water, resuspended in deionized water, and frozen. Cells were then lyophilized to dryness and used to perform a HCl-methanol catalyzed transesterification reaction to produce fatty acid methyl esters (FAME). These samples were dissolved in isooctane and injected into a gas chromatography system (Agilent Technologies) equipped with a flame ionization detector. Table 1 shows the percentage of each fatty acid that was converted to methylene- and methyl-branched fatty acids.

TABLE 1

Fatty acid conversion to methylene and methyl branched fatty acids with *E. coli* expressing the tmpB and tmpA genes from *M. hydrocarbonclasticus* and *T. halophila*.

| Fatty acid | *E. coli* + pNC1074 (*M. hydrocarbonclausticus* tmpBA) percent conversion | *E. coli* + pNC1076 (*T. halophila*) tmpBA percent conversion |
|---|---|---|
| 12:1Δ10 | 0% | 0% |
| 13:1Δ12 | 0% | 0% |
| 14:1Δ9 | 89% | 95% |
| 15:1Δ10 | 86% | 69% |
| 16:1Δ9 | 55% | 95% |
| 17:1Δ10 | 36% | 19% |
| 18:1Δ6 | 0% | 0% |
| 18:1Δ9 | 42% | 47% |
| 18:1Δ11 | 9% | 8% |
| 19:1Δ7 | 0% | 0% |
| 19:1Δ10 | 0% | 0% |
| 20:1Δ5 | 0% | 0% |
| 20:1Δ8 | 0% | 0% |
| 20:1Δ11 | 0% | 0% |
| 22:1Δ13 | 0% | 0% |
| 24:1Δ15 | 0% | 0% |

As shown in Table 1, methylation occurred on fatty acids with 14, 15, 16, 17, and 18 carbons, and on Δ9, Δ10, and Δ11 double bond positions.

Example 3 tmpB Gene Expression in Yeast

To test the production of 10-methylene fatty acids by the tmpB genes in the yeast *Saccharomyces cerevisiae* and *Yarrowia lipolytica*, the genes containing native bacterial codons were cloned into a standard *Yarrowia* overexpression vector. The vector contains a selectable NAT marker and a 2μ origin of replication for high copy maintenance in *Saccharomyces cerevisiae*. The resulting plasmids are pNC996 (*Desulfobacter postgatei* tmpB), pNC998 (*Desulfobacula balticum* tmpB), pNC1000 (*Desulfobacula toluolica* tmpB), pNC1002 (*Marinobacter hydrocarbonclasticus* tmpB), pNC1006 (*Thiohalospira halophila* tmpB). For *Saccharomyces*, plasmids were transformed into NS20 by standard heat shock protocol. Single cells of the resulting transformations were selected and further grown in 96-well shaking plates in YPD supplemented with 50 μg/mL Nourseothrycin for 2 days at 30° C. For *Yarrowia*, plasmids were transformed into strain NS1009. Resulting transformed strains were grown in 96-well shaking plates in standard nitrogen limited media for 4 days at 30° C. For all yeast experiments, cell pellets were isolated by centrifugation and freeze dried for fatty acid analysis by gas chromatography as performed for *E. coli* samples. Total fatty acids were measured and the total amount of C16 and C18 fatty acids containing the methylene intermediates were quantified.

Figure 4:
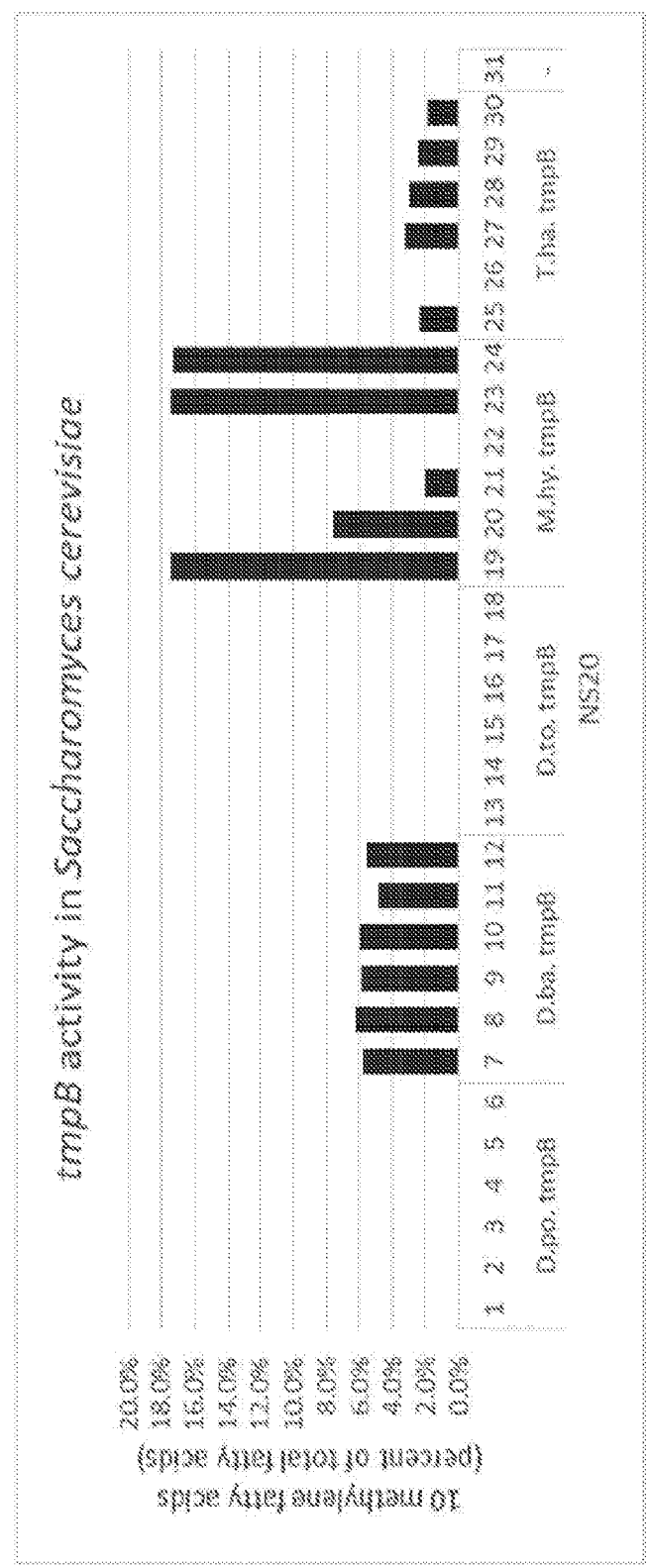
FIG. 4 is a graph showing the percentage of 10-methylene fatty acids in *Saccharomyces cerevisiae* transformed with plasmids expressing tmpB from the indicated species: *D. postgatei* (D.po.), *D. balticum* (D.ba.), *D. toluolica* (D.to.), *M. hydrocarbonclasticus* (M.hy.) and *T. halophila* (T.ha.), or an empty vector control (−).
Figure 5:
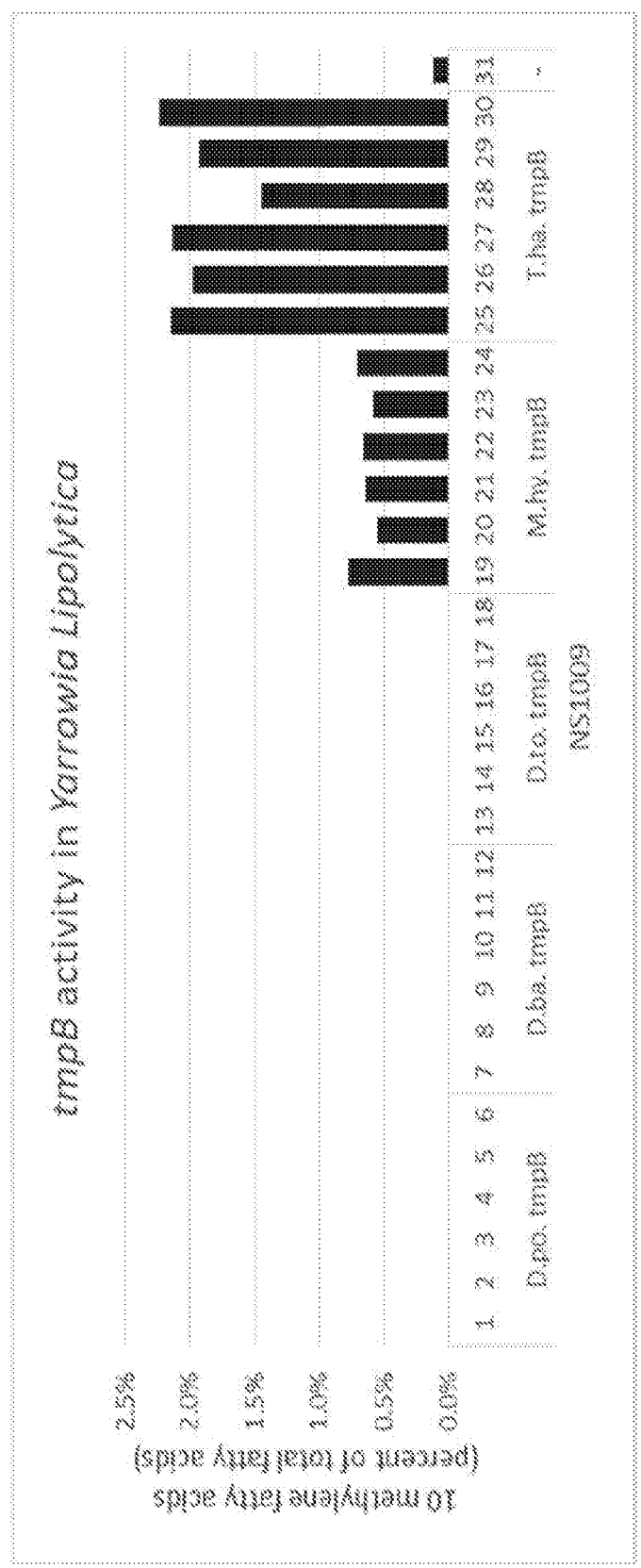
FIG. 5 is a graph showing the percentage of 10-methylene fatty acids in *Yarrowia lipolytica* transformed with plasmids expressing tmpB from the indicated species: *D. postgatei* (D.po.), *D. balticum* (D.ba.), *D. toluolica* (D.to.), *M. hydrocarbonclasticus* (M.hy.) and *T. halophila* (T.ha.), or an empty vector control (−).
Figure 8C:
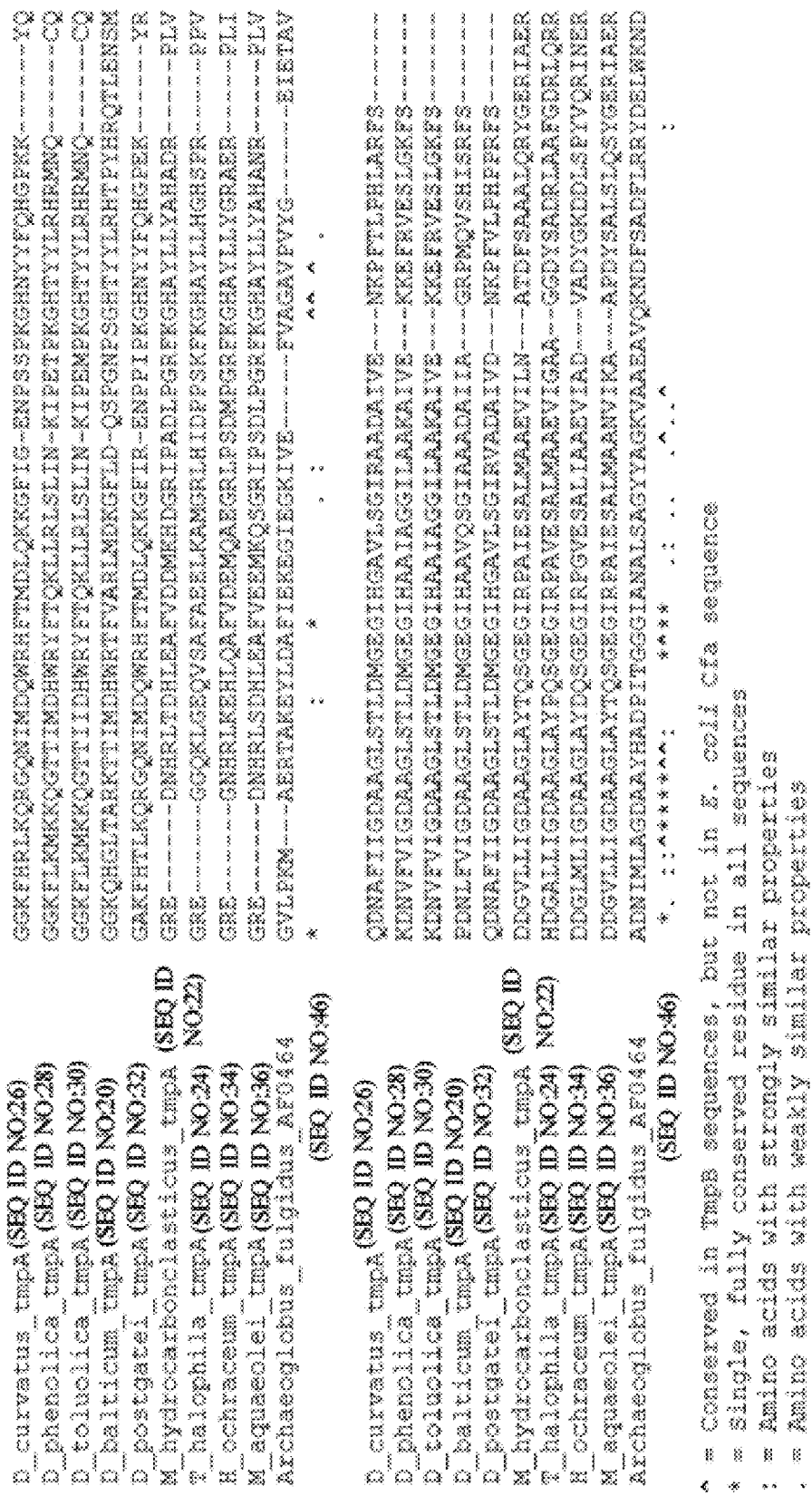

Results: Three tmpB genes produced 10-methylene fatty acids in NS20, *Desulfobacula balticum*, *Marinobacter hydrocarbonclasticus*, and *Thiohalospira halophila* (FIG. 4). The tmpB genes from *Marinobacter hydrocarbonclasticus*, and *Thiohalospira halophila* were able to produce 10-methylene fatty acids in *Yarrowia lipolytica* (FIG. 5).

Example 4 tmpB and tmpA Sequence Analysis

TmpB protein sequences encoded by the tmpB genes from *Desulfobacula balticum*, *Marinobacter hydrocarbon-* clasticus, Thiohalospira halophila, Desulfobacter curvatus, Desulfobacter phenolica, Desulfobacula toluolica, Desulfobacter postgatei, Halofilum ochraceum, and Marinobacter aquaeolei were aligned with the cyclopropane fatty acid synthase (Cfa) enzyme from Escherichia coli with the CLUSTAL OMEGA software program (European Molecular Biology Laboratory, EMBL). FIGS. 7A-D show the alignment of these protein sequences and indicates a number of amino acids that are conserved in the tmsB protein sequences but not in the E. coli Cfa sequence. The following amino acids are conserved in the TmpB aligned proteins, but not present in the E. coli Cfa protein: Y163, T175, R199, E211, G269, Y271, N313, N319, W389 (amino acid number based on the M. hydrocarbonclasticus TmpB protein). The percent sequence identity of each of the aligned proteins as compared to M. hydrocarbonclasticus tmpB is indicated below:

|  | % Identity of amino acid sequence |
|---|---|
| Desulfobacula balticum TmpB | 37% |
| Thiohalospira halophila TmpB | 58% |
| Desulfobacter curvatus TmpB | 43% |
| Desulfobacter phenolica TmpB | 39% |
| Desulfobacula toluolica TmpB | 39% |
| Desulfobacter postgatei TmpB | 43% |
| Halofilum ochraceum TmpB | 59% |
| Marinobacter aquaeolei TmpB | 88% |
| Escherichia coli Cfa | 46% |

TmpA protein sequences encoded by the tmpA genes from Desulfobacula balticum, Marinobacter hydrocarbonclasticus, Thiohalospira halophila, Desulfobacter curvatus, Desulfobacter phenolica, Desulfobacula toluolica, Desulfobacter postgatei, Halofilum ochraceum, and Marinobacter aquaeolei were aligned with the Archaeoglobus fulgidus geranylgeranyl reductase protein AF0464 with the CLUSTAL OMEGA software program (European Molecular Biology Laboratory, EMBL). FIGS. 8A-D show the alignment of these protein sequences and indicates a number of amino acids that are conserved in the tmsA protein sequences but not in the Archaeoglobus fulgidus geranylgeranyl reductase protein AF0464. The following amino acids are conserved in the TmpA aligned proteins, but not present in the Archaeoglobus fulgidus geranylgeranyl reductase protein AF0464: I8, L22, F37, P38, R39, K41, G45, W46, P49, G144, C148, P149, E169, E171, L197, I212, C249, H250, Y252, I270, G275, L276, E283, A296, A299 (amino acid number based on the M. hydrocarbonclasticus TmpA protein).

|  | % Identity of amino acid sequence |
|---|---|
| Desulfobacula balticum TmpA | 33% |
| Thiohalospira halophila TmpA | 57% |
| Desulfobacter curvatus TmpA | 36% |
| Desulfobacter phenolica TmpA | 34% |
| Desulfobacula toluolica TmpA | 34% |
| Desulfobacter postgatei TmpA | 34% |
| Halofilum ochraceum TmpA | 64% |
| Marinobacter aquaeolei TmpA | 83% |
| Archaeoglobus fulgidus AF0464 | 27% |

The invention claimed is:

1. A cell comprising an exogenous tmpB gene encoding a tmpB protein from a bacterium of the genus *Desulfobacter, Desulfobacula, Marinobacter, Thiohalospira, Thiohalorhabdus, Desulfotignum,* or *Halofilum* and either a branched (methyl)lipid or an exomethylene-substituted lipid, wherein
   (1) the branched (methyl)lipid is a carboxylic acid, carboxylate, ester, thioester, or amide, and
   the branched (methyl)lipid comprises a saturated or unsaturated branched aliphatic chain comprising a branching methyl group; or
   (2) the exomethylene-substituted lipid is a carboxylic acid, carboxylate, ester, thioester, or amide,
   the exomethylene-substituted lipid comprises a branched aliphatic chain, and
   the aliphatic chain is substituted with an exomethylene group.

2. The cell of claim 1, wherein the branched (methyl)lipid or the exomethylene-substituted lipid is a fatty acid from 14 to 18 carbons long with a methyl moiety in the Δ9, Δ10, or Δ11 position.

3. The cell of claim 2, wherein the branched (methyl)lipid is 10-methylstearate, or an ester, thioester, or amide thereof or the exomethylene-substituted lipid is 10-methylenestearate, or an ester, thioester, or amide thereof.

4. The cell of claim 1, wherein the tmpB protein is *Desulfobacula balticum* enzyme tmpB, *Marinobacter hydrocarbonclasticus* enzyme tmpB, *Thiohalospira halophila* enzyme tmpB, *Desulfobacter curvatus* enzyme tmpB, *Desulfobacter phenolica* enzyme tmpB, *Desulfobacula toluolica* enzyme tmpB, *Desulfobacter postgatei* enzyme tmpB, *Halojilum ochraceum* enzyme tmpB, or *Marinobacter aquaeolei* enzyme tmpB.

5. The cell of claim 1, wherein the tmpB protein has at least 90% sequence identity to SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

6. The cell of claim 1, further comprising a recombinant tmpA gene encoding a reductase tmpA protein from a bacterium of the genus *Desulfobacter, Desulfobacula, Marinobacter, Thiohalospira, Thiohalorhabdus, Desulfotignum,* or *Halofilum*.

7. The cell of claim 6, wherein the tmpA protein is capable of converting a methylene-substituted lipid to a methyl-substituted lipid.

8. The cell of claim 7, wherein the methylene-substituted lipid is a fatty acid from 14 to 18 carbons long with a methylene substitution in the Δ9, Δ10, or Δ11 position and the methyl-substituted lipid is a fatty acid from 14 to 18 carbons long with a methyl moiety in the Δ9, Δ10, or Δ11 position.

9. The cell of claim 6, wherein the tmpA protein is selected from *Desulfobacula balticum* enzyme tmpA, *Marinobacter hydrocarbonclasticus* enzyme tmpA, *Thiohalospira halophila* enzyme tmpA, *Desulfobacter curvatus* enzyme tmpA, *Desulfobacter phenolica* enzyme tmpA, *Desulfobacula toluolica* enzyme tmpA, *Desulfobacter postgatei* enzyme tmpA, *Halofilum ochraceum* enzyme tmpA, and *Marinobacter aquaeolei* enzyme tmpA.

10. The cell of claim 6, wherein the tmpA protein has at least 90% sequence identity to SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36.

11. The cell of claim 6, wherein the tmpB gene and the tmpA gene are included in a single open reading frame encoding a fusion protein comprising both the tmpB protein and the tmpA protein.

12. The cell of claim 1, wherein to 15% by weight of the fatty acids of the cell are 10-methyl fatty acids or 10-methylene fatty acids.

13. The cell of claim 1, wherein the cell lacks an endogenous methyltransferase gene.

14. The cell of claim 1, wherein the cell lacks the endogenous ability to produce the branched (methyl)lipid or exomethylene-substituted lipid.

15. The cell of claim 1, wherein the cell is a bacterial cell, a fungal cell, an algal cell, a mold cell, a plant cell, or a yeast cell.

16. The cell of claim 1, wherein the cell is a fungal cell, an algal cell, a mold cell, a plant cell, or a yeast cell.

17. The cell of claim 1, wherein the cell is a yeast cell.

18. The cell of claim 1, wherein the cell is selected from the group consisting of *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia*.

19. The cell of claim 1, wherein the cell is selected from the group consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, and *Yarrowia lipolytica*.

20. A method of producing a branched (methyl)lipid or exomethylene-substituted lipid, comprising contacting the cell of claim 1 with a substrate fatty acid, methionine, or both a substrate fatty acid and methionine, wherein the substrate fatty acid comprises a fatty acid from 14 to 18 carbons long with a double bond in the Δ9, Δ10, or Δ11 position.

21. A nucleic acid comprising a recombinant tmpB gene encoding a tmpB protein from a bacterium of the genus *Desulfobacter, Desulfobacula, Marinobacter, Thiohalospira, Thiohalorhabdus, Desulfotignum*, or *Halofilum* and a first promoter operably linked to the recombinant tmpB gene.

22. The nucleic acid of claim 21, wherein the tmpB gene has at least 80% sequence identity to SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17.

23. The nucleic acid of claim 21, wherein the tmpB gene encodes a protein having at least 90% sequence identity to SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18.

24. The nucleic acid of claim 21, wherein the tmpB gene is codon-optimized for expression in yeast, algae, or plants.

25. The nucleic acid of any one of claim 21, further comprising a tmpA gene encoding a tmpA protein from a bacterium of the genus *Desulfobacter, Desulfobacula, Marinobacter, Thiohalospira, Thiohalorhabdus, Desulfotignum*, or *Halofilum*.

26. The nucleic acid of claim 25, wherein the reductase tmpA gene has at least 80% sequence identity to SEQ ID NO:19, SEQ ID NO:21, SEQ ID NO:23, SEQ ID NO:25, SEQ ID NO:27, SEQ ID NO:29, SEQ ID NO:31, SEQ ID NO:33, or SEQ ID NO:35.

27. The nucleic acid of claim 25, wherein the tmpA gene encodes a protein having at least 90% sequence identity to SEQ ID NO:20, SEQ ID NO:22, SEQ ID NO:24, SEQ ID NO:26, SEQ ID NO:28, SEQ ID NO:30, SEQ ID NO:32, SEQ ID NO:34, or SEQ ID NO:36.

28. The nucleic acid of claim 25, wherein the tmpA gene is fused in frame with the tmpB gene.

29. The nucleic acid of claim 28, further comprising a nucleic acid linker sequence between the tmpB gene and the tmpA gene, wherein the nucleic acid linker sequence encodes a linker peptide between the tmpB protein and the tmpA protein.

30. The nucleic acid of claim 25, wherein the tmpA gene is operably linked to a second promoter.

31. The nucleic acid of claim 21, wherein the promoter is a yeast promoter, an algae promoter, or a plant promoter.

32. The nucleic acid of claim 21, wherein the promoter is a yeast promoter.

\* \* \* \* \*

SEQUENCE LISTING

```
<160> NUMBER OF SEQ ID NOS: 46

<210> SEQ ID NO 1
<211> LENGTH: 1122
<212> TYPE: DNA
<213> ORGANISM: Unknown
<220> FEATURE:
<223> OTHER INFORMATION: Disulfobacula balticum

<400> SEQUENCE: 1
atgaagttgg gacaggccag agaattattt tcagagatga tgaatcatgc cggcatccga      60
gtgaatgggg accggccgtt tgatatccgg atcaaaaacg atcaatttt ccagcgggtg      120 acgtcatccc cggctttggg tctgggtgag tcttatatgg atggctggtg ggattgtccg      180
gcaccggatc agttcattga aaaagtgctt cgggccaatc ttctcaaaca gatcaaacag      240
gaccggatca cggcctggaa cgccctgatg gcaaagattt tcaatctcca gaccattaaa      300
cgggcattta ccgtgggcaa acagcattat gatatcggca atgatctgta tcaaatgatg      360
ctgggcaaac ggatgcagta tacctgcggg tactggaaag acgcccggaa cctggacgag      420
gcccaggagg ccaaactgga aatgatctgc cggaaactgg cactggcacc gggaatgaat      480
gttctggaac tcgggtgcgg gttcggcgga tttgcccggt atgcggctga aaaatatcag      540
gtgtccgtga ccggttcac cgtgtcgaaa aaacaggcgg aattcggccg ggaatactgc      600
aaagacctgc ccgtggatat ccggctggat gattaccgca atgccagagg cacttatgac      660
cgcatcctgt ccatcggcct gatggagcat gtgggattta aaaactaccg gacctatatg      720
gaactgaccc gcaacctgct taaaaaagac ggcatcgcgt tcgtgcatac catcggcgga      780
aatatcacca cccggatctg caatccctgg acggccaaat acatttttcc caattccgtg      840
```

```
ctgccgtcca tttccgaact gggaagagcc atggaagggc tgtttgtcct ggaagactgc    900
cacaatttcg gggaagatta tgacaaaacc ctgatggcct ggtatgacaa cttcaaggcg    960
gcctggccca agctcaaaaa ccggtatgac gaccggtttt ttcggatgtg ggaatattac   1020
ctgctcagtt ccgccggcgg gttccgggca cggtccatgc agctgtggca gatggtgctg   1080
acccggcccg ccggccgaa accagactgc cggatctcgt ga                      1122
```

<210> SEQ ID NO 2
<211> LENGTH: 373
<212> TYPE: PRT
<213> ORGANISM: Unknown
<220> FEATURE:
<223> OTHER INFORMATION: Desulfobacula balticum

<400> SEQUENCE: 2

```
Met Lys Leu Gly Gln Ala Arg Glu Leu Phe Ser Glu Met Met Asn His
1               5                   10                  15

Ala Gly Ile Arg Val Asn Gly Asp Arg Pro Phe Asp Ile Arg Ile Lys
            20                  25                  30

Asn Asp Gln Phe Phe Gln Arg Val Thr Ser Ser Pro Ala Leu Gly Leu
        35                  40                  45

Gly Glu Ser Tyr Met Asp Gly Trp Asp Cys Pro Ala Pro Asp Gln
    50                  55                  60

Phe Ile Glu Lys Val Leu Arg Ala Asn Leu Leu Lys Gln Ile Lys Gln
65                  70                  75                  80

Asp Arg Ile Thr Ala Trp Asn Ala Leu Met Ala Lys Ile Phe Asn Leu
                85                  90                  95

Gln Thr Ile Lys Arg Ala Phe Thr Val Gly Lys Gln His Tyr Asp Ile
            100                 105                 110

Gly Asn Asp Leu Tyr Gln Met Met Leu Gly Lys Arg Met Gln Tyr Thr
        115                 120                 125

Cys Gly Tyr Trp Lys Asp Ala Arg Asn Leu Asp Glu Ala Gln Glu Ala
    130                 135                 140

Lys Leu Glu Met Ile Cys Arg Lys Leu Ala Leu Ala Pro Gly Met Asn
145                 150                 155                 160

Val Leu Glu Leu Gly Cys Gly Phe Gly Gly Phe Ala Arg Tyr Ala Ala
                165                 170                 175

Glu Lys Tyr Gln Val Ser Val Thr Gly Phe Thr Val Ser Lys Lys Gln
            180                 185                 190

Ala Glu Phe Gly Arg Glu Tyr Cys Lys Asp Leu Pro Val Asp Ile Arg
        195                 200                 205

Leu Asp Asp Tyr Arg Asn Ala Arg Gly Thr Tyr Asp Arg Ile Leu Ser
    210                 215                 220

Ile Gly Leu Met Glu His Val Gly Phe Lys Asn Tyr Arg Thr Tyr Met
225                 230                 235                 240

Glu Leu Thr Arg Asn Leu Leu Lys Lys Asp Gly Ile Ala Phe Val His
                245                 250                 255

Thr Ile Gly Gly Asn Ile Thr Thr Arg Ile Cys Asn Pro Trp Thr Ala
            260                 265                 270

Lys Tyr Ile Phe Pro Asn Ser Val Leu Pro Ser Ile Ser Glu Leu Gly
        275                 280                 285

Arg Ala Met Glu Gly Leu Phe Val Leu Glu Asp Cys His Asn Phe Gly
    290                 295                 300
```

Glu Asp Tyr Asp Lys Thr Leu Met Ala Trp Tyr Asp Asn Phe Lys Ala
305                 310                 315                 320

Ala Trp Pro Lys Leu Lys Asn Arg Tyr Asp Arg Phe Phe Arg Met
            325                 330                 335

Trp Glu Tyr Tyr Leu Leu Ser Ser Ala Gly Gly Phe Arg Ala Arg Ser
            340                 345                 350

Met Gln Leu Trp Gln Met Val Leu Thr Arg Pro Gly Arg Pro Lys Pro
        355                 360                 365

Asp Cys Arg Ile Ser
        370

<210> SEQ ID NO 3
<211> LENGTH: 1314
<212> TYPE: DNA
<213> ORGANISM: Marinobacter hydrocarbonoclasticus

<400> SEQUENCE: 3

```
atggcacagg gcacagctcc aaagacggac tattctgaca gcaacaccaa agcacatgtt      60
cttagcctgc cactggaaaa cagtcaggct gatcgcgaac cacacagcta tgaacgctgg     120
ctgatcgcca agttgatgcg aatggccggt tcacccgcca tacgcttcca gctgtggaat     180
ggcgaggtca tcgagccaga gcaagggcta gcccgcttca ccctgcacct gaaggatcac     240
aaggcactct actccctcgt tgccaacccc aacctcgcct cggcgatct gtacagcgct      300 ggccgcctgg agatcgatgg cgacctgcct gatctgatgg aaagcccttta ccgatcagtc    360 cacgccgccc ggcagaaatg ccaaaatgg ctggatgcgc tttggaagaa tcacaacccc      420
agagcaaccg gcatttccga ggccaaggaa acattcacc accactacga cctgggcaac      480
gagttttacc aactctggct ggacaacgca gaaatgcagt acacctgtgc ctattacgag     540
caccccggta acacactgga gcaggcacaa ctggccaaac tggagcatgt gtgccggaag    600
ctgcgcctga ggccaggcat gacggtggtg aagccggct gtggctgggg cggcctggcc      660
cgttatatgg cccgcaacta cggcgtgaaa gttcactcct acaacatatc ccgtgaacaa    720
ctggcatacg cccaggccga gtctgaacgc aagggctcg atggtcttat tacctatgtc      780
gaggacgact accgcaatat caccggccag tacgacgcat tcgtctctgt tggcatgctg    840
gagcatgttg gcaaggaaaa ctaccgagcc tgtcggagc tgatcaagcg cagcctgaaa    900
cccaacggca tagctctgct ccacagtatc gggcgcaacc gccccatgct aatgaatgcc    960
tggatagaga gcggatcttt ccccggcgcc taccctccca gtatcggcga gtttatggaa   1020
atctgtgagc acggcgactt ctcggtactg gatgtggaga acctgcggct gcactatgcc   1080
cagaccctga gccactggac ggagcgcttc gaagccaatg ccgagcgcgt taccgagatg   1140
tacgacgaac acttcaccccg cgcctggcgg ctttatctgg cgggctcaat tgcagcattc    1200
cgggccggtt ctctgcagct gttccaggtg gtgtttaccc atggcgataa caaccagctg   1260
ccccagagcc ggcaggactt gtatgcgttt ccggcaacac cggagggcaa ctga         1314
```

<210> SEQ ID NO 4
<211> LENGTH: 437
<212> TYPE: PRT
<213> ORGANISM: Marinobacter hydrocarbonoclasticus

<400> SEQUENCE: 4

Met Ala Gln Gly Thr Ala Pro Lys Thr Asp Tyr Ser Asp Ser Asn Thr
1               5                   10                  15

Lys Ala His Val Leu Ser Leu Pro Leu Glu Asn Ser Gln Ala Asp Arg
            20                  25                  30

Glu Pro His Ser Tyr Glu Arg Trp Leu Ile Ala Lys Leu Met Arg Met
        35                  40                  45

Ala Gly Ser Pro Ala Ile Arg Phe Gln Leu Trp Asn Gly Glu Val Ile
    50                  55                  60

Glu Pro Glu Gln Gly Leu Ala Arg Phe Thr Leu His Leu Lys Asp His
65                  70                  75                  80

Lys Ala Leu Tyr Ser Leu Val Ala Asn Pro Asn Leu Ala Phe Gly Asp
                85                  90                  95

Leu Tyr Ser Ala Gly Arg Leu Glu Ile Asp Gly Asp Leu Pro Asp Leu
            100                 105                 110

Met Glu Ser Leu Tyr Arg Ser Val His Ala Ala Arg Gln Lys Trp Pro
        115                 120                 125

Lys Trp Leu Asp Ala Leu Trp Lys Asn His Asn Pro Arg Ala Thr Gly
    130                 135                 140

Ile Ser Glu Ala Lys Glu Asn Ile His His Tyr Asp Leu Gly Asn
145                 150                 155                 160

Glu Phe Tyr Gln Leu Trp Leu Asp Asn Ala Glu Met Gln Tyr Thr Cys
                165                 170                 175

Ala Tyr Tyr Glu His Pro Gly Asn Thr Leu Glu Gln Ala Gln Leu Ala
            180                 185                 190

Lys Leu Glu His Val Cys Arg Lys Leu Arg Leu Arg Pro Gly Met Thr
        195                 200                 205

Val Val Glu Ala Gly Cys Gly Trp Gly Gly Leu Ala Arg Tyr Met Ala
    210                 215                 220

Arg Asn Tyr Gly Val Lys Val His Ser Tyr Asn Ile Ser Arg Glu Gln
225                 230                 235                 240

Leu Ala Tyr Ala Gln Ala Glu Ser Glu Arg Gln Gly Leu Asp Gly Leu
                245                 250                 255

Ile Thr Tyr Val Glu Asp Asp Tyr Arg Asn Ile Thr Gly Gln Tyr Asp
            260                 265                 270

Ala Phe Val Ser Val Gly Met Leu Glu His Val Gly Lys Glu Asn Tyr
        275                 280                 285

Arg Ala Leu Ser Glu Leu Ile Lys Arg Ser Leu Lys Pro Asn Gly Ile
    290                 295                 300

Ala Leu Leu His Ser Ile Gly Arg Asn Arg Pro Met Leu Met Asn Ala
305                 310                 315                 320

Trp Ile Glu Lys Arg Ile Phe Pro Gly Ala Tyr Pro Pro Ser Ile Gly
                325                 330                 335

Glu Phe Met Glu Ile Cys Glu His Gly Asp Phe Ser Val Leu Asp Val
            340                 345                 350

Glu Asn Leu Arg Leu His Tyr Ala Gln Thr Leu Ser His Trp Thr Glu
        355                 360                 365

Arg Phe Glu Ala Asn Ala Glu Arg Val Thr Glu Met Tyr Asp Glu His
    370                 375                 380

Phe Thr Arg Ala Trp Arg Leu Tyr Leu Ala Gly Ser Ile Ala Ala Phe
385                 390                 395                 400

Arg Ala Gly Ser Leu Gln Leu Phe Gln Val Val Phe Thr His Gly Asp
                405                 410                 415

Asn Asn Gln Leu Pro Gln Ser Arg Gln Asp Leu Tyr Ala Phe Pro Ala
            420                 425                 430

```
Thr Pro Glu Gly Asn
        435
```

<210> SEQ ID NO 5
<211> LENGTH: 1227
<212> TYPE: DNA
<213> ORGANISM: Unknown
<220> FEATURE:
<223> OTHER INFORMATION: Thiohalospira halophila

<400> SEQUENCE: 5

| | | | | | |
|---|---|---|---|---|---|
| atgcaaggga | acacgcccca | cggtcgcgcc | aagggcgcag | acctggccct | ggctgagcgg | 60 |
| atcctcgccg | gcatggggaa | tcctgcgctg | gccgtgatcc | tctgggacgg | tagccgtgtc | 120 |
| gggccgtcgg | atacggtggc | cgatgtcgcg | gtcgccgatc | ggcgggcgtt | gtgggccatt | 180 |
| gccctgaatg | cggatcttca | cttcggcgac | ctctatgcgg | ccggtcgggt | gcgcatcgat | 240 |
| ggtgacctgc | agaccttcct | ggagacgggg | tatcgcgcca | tggacgggca | gccgaccccc | 300 |
| tggccgttgc | gcttcctcca | ccgctggcag | aatcggccgc | gacggaactc | cctgaacggc | 360 |
| tcccgggaga | acatccacca | tcactatgac | ctgggcaatg | acttctaccg | gctctggctg | 420 |
| gatcaggagg | tcatgcagta | cacctgcgcc | tactatccca | gcgaatcggc | cagcctggag | 480 |
| gaggcacaga | tagccaagct | ccaccatgtc | tgccgcaagc | tgcggctcaa | gccgggagat | 540 |
| acggtagtcg | aggcgggttg | cggctggggt | ggcctggctc | gcttcatggc | caagcattat | 600 |
| ggcgtgaagg | tacgcgcctt | taatgtctcg | caggagcagt | tgcgcttcgc | ccgggaggag | 660 |
| gccgaacggc | aggggctctc | ggatcgggtg | gagtacgtcg | aggacgacta | ccggaacatt | 720 |
| gaggggacct | acgacgtctt | cgtctcggtg | ggtatgctcg | agcatgtcgg | cacggagcaa | 780 |
| tatccggaac | tgggggcagt | gatcgatcgg | gtgcttgccc | ccacggccg | gggcctcatc | 840 |
| cacaccatcg | gcggaatcg | gccccagctc | atgaatccgt | ggatcgaaaa | gcgtatcttt | 900 |
| cccggggcct | accccccac | cctgcgggag | atggcggcca | tcttcgagcc | gtatgccttc | 960 |
| tcgatccagg | acgtggaaaa | catccggctc | cactacgcgc | ggaccctcca | gcactggctg | 1020 |
| gagcggttcg | aggccaacgt | ggagacggtc | cggcagatgt | cgacgagca | cttcgtgcgg | 1080 |
| acctggcggc | tctacctcgc | cggctccatt | gccagcttca | ccacggggga | gctgcagctc | 1140 |
| ttccagaccg | tctttacacg | gccggactac | aatgagctcc | cctggagccg | cgcctatctc | 1200 |
| tacaccgccg | gggaggaagg | ggcatga | | | | 1227 |

<210> SEQ ID NO 6
<211> LENGTH: 408
<212> TYPE: PRT
<213> ORGANISM: Unknown
<220> FEATURE:
<223> OTHER INFORMATION: Thiohalospira halophila

<400> SEQUENCE: 6

```
Met Gln Gly Asn Thr Pro His Gly Arg Ala Lys Gly Ala Asp Leu Ala
1               5                   10                  15

Leu Ala Glu Arg Ile Leu Ala Gly Met Gly Asn Pro Ala Leu Ala Val
            20                  25                  30

Ile Leu Trp Asp Gly Ser Arg Val Gly Pro Ser Asp Thr Val Ala Asp
        35                  40                  45

Val Ala Val Ala Asp Arg Arg Ala Leu Trp Ala Ile Ala Leu Asn Ala
    50                  55                  60
```

Asp Leu His Phe Gly Asp Leu Tyr Ala Ala Gly Arg Val Arg Ile Asp
65                  70                  75                  80

Gly Asp Leu Gln Thr Phe Leu Glu Thr Gly Tyr Arg Ala Met Asp Gly
                85                  90                  95

Gln Pro Thr Pro Trp Pro Leu Arg Phe Leu His Arg Trp Gln Asn Arg
            100                 105                 110

Pro Arg Arg Asn Ser Leu Asn Gly Ser Arg Glu Asn Ile His His His
        115                 120                 125

Tyr Asp Leu Gly Asn Asp Phe Tyr Arg Leu Trp Leu Asp Gln Glu Val
130                 135                 140

Met Gln Tyr Thr Cys Ala Tyr Tyr Pro Ser Glu Ser Ala Ser Leu Glu
145                 150                 155                 160

Glu Ala Gln Ile Ala Lys Leu His His Val Cys Arg Lys Leu Arg Leu
                165                 170                 175

Lys Pro Gly Asp Thr Val Val Glu Ala Gly Cys Gly Trp Gly Gly Leu
            180                 185                 190

Ala Arg Phe Met Ala Lys His Tyr Gly Val Lys Val Arg Ala Phe Asn
        195                 200                 205

Val Ser Gln Glu Gln Leu Arg Phe Ala Arg Glu Glu Ala Glu Arg Gln
210                 215                 220

Gly Leu Ser Asp Arg Val Glu Tyr Val Glu Asp Asp Tyr Arg Asn Ile
225                 230                 235                 240

Glu Gly Thr Tyr Asp Val Phe Val Ser Val Gly Met Leu Glu His Val
                245                 250                 255

Gly Thr Glu Gln Tyr Pro Glu Leu Gly Ala Val Ile Asp Arg Val Leu
            260                 265                 270

Ala Pro His Gly Arg Gly Leu Ile His Thr Ile Gly Arg Asn Arg Pro
        275                 280                 285

Gln Leu Met Asn Pro Trp Ile Glu Lys Arg Ile Phe Pro Gly Ala Tyr
290                 295                 300

Pro Pro Thr Leu Arg Glu Met Ala Ala Ile Phe Glu Pro Tyr Ala Phe
305                 310                 315                 320

Ser Ile Gln Asp Val Glu Asn Ile Arg Leu His Tyr Ala Arg Thr Leu
                325                 330                 335

Gln His Trp Leu Glu Arg Phe Glu Ala Asn Val Glu Thr Val Arg Gln
            340                 345                 350

Met Phe Asp Glu His Phe Val Arg Thr Trp Arg Leu Tyr Leu Ala Gly
        355                 360                 365

Ser Ile Ala Ser Phe Thr Thr Gly Glu Leu Gln Leu Phe Gln Thr Val
370                 375                 380

Phe Thr Arg Pro Asp Tyr Asn Glu Leu Pro Trp Ser Arg Ala Tyr Leu
385                 390                 395                 400

Tyr Thr Ala Gly Glu Glu Gly Ala
                405

<210> SEQ ID NO 7
<211> LENGTH: 1122
<212> TYPE: DNA
<213> ORGANISM: Desulfobacter curvatus

<400> SEQUENCE: 7
atgagaaatc agaatatcaa aaatccatc aacaaattat tgaaatttgc cggtatcacc      60
gttaacggaa acaatcccta cgacattcag attaagaatg accggcttta ccagcgggta    120

```
atccatgaac ctgctctggg tcttggtgaa gcctatatgg atcagtggtg ggagtgccgc    180
gccctggatc agttcatggc aaaagtgttg cgcgcaaatc ttggggaagt attaaaaaaa    240
gagtggcaga tcacatggaa tattctaaag gcaaagcttt ttaaccaaca gtcttccagg    300
cgtgcgttca tggtgggcca aagccattat gatgtcggca atgaacttta tcagggcatg    360
ctggacaaac aaatgcagta tacctgcgga tactggaaag atgccaccac ccttgatcag    420
gcccaggagg cgaaactggc gctggtctgc cggaagttaa aactggcgcc cggcatgaaa    480
gtacttgagt tgggatgtgg ttttggcggg tttgcccact atgcggcaac aaagtacggc    540
gttgaagtaa ccggatacac cgtttccaaa gagcaggccc gatttggaaa agagctgtgc    600
cgggggcttc ccgttgacat ccggctggca gattacagaa ccgccaccgg agagtatgat    660
cgggtggtct ccattggttt aatggagcat gtggggtata aaattatggg cacttacatg    720
aaactgacca accggttgct aagggatgac ggcattgcat tgattcatac catcggtagt    780
aatgccagtt gttctgcttg taacccatgg actgcaaaat atattttccc caatggcatg    840
cttccctcca ttgcccagtt gggaaaagcc atggaaaacc aatttgtcat ggaggactgg    900
cataactttg gagaggacta cgataaaaca ttaatggcat ggtacgaaaa tttcaaacag    960
gtgtggccca atcttgaaga tagatacagt gatcggtttt atcgcatgtg ggagtattat    1020
ttgttaagct gtgccggagg attccggtca cgatccatgc agctatggca gattgtgatg    1080
actaaacagg ggacttcagc accctgctgc cgccttgtat ag                       1122

<210> SEQ ID NO 8
<211> LENGTH: 373
<212> TYPE: PRT
<213> ORGANISM: Desulfobacter curvatus

<400> SEQUENCE: 8

Met Arg Asn Gln Asn Ile Lys Lys Ser Ile Asn Lys Leu Leu Lys Phe
1               5                   10                  15

Ala Gly Ile Thr Val Asn Gly Asn Asn Pro Tyr Asp Ile Gln Ile Lys
            20                  25                  30

Asn Asp Arg Leu Tyr Gln Arg Val Ile His Glu Pro Ala Leu Gly Leu
        35                  40                  45

Gly Glu Ala Tyr Met Asp Gln Trp Trp Glu Cys Arg Ala Leu Asp Gln
    50                  55                  60

Phe Met Ala Lys Val Leu Arg Ala Asn Leu Gly Glu Val Leu Lys Lys
65                  70                  75                  80

Glu Trp Gln Ile Thr Trp Asn Ile Leu Lys Ala Lys Leu Phe Asn Gln
                85                  90                  95

Gln Ser Ser Arg Arg Ala Phe Met Val Gly Gln Ser His Tyr Asp Val
            100                 105                 110

Gly Asn Glu Leu Tyr Gln Gly Met Leu Asp Lys Gln Met Gln Tyr Thr
        115                 120                 125

Cys Gly Tyr Trp Lys Asp Ala Thr Thr Leu Asp Gln Ala Gln Glu Ala
    130                 135                 140

Lys Leu Ala Leu Val Cys Arg Lys Leu Lys Leu Ala Pro Gly Met Lys
145                 150                 155                 160

Val Leu Glu Leu Gly Cys Gly Phe Gly Gly Phe Ala His Tyr Ala Ala
                165                 170                 175

Thr Lys Tyr Gly Val Glu Val Thr Gly Tyr Thr Val Ser Lys Glu Gln
            180                 185                 190
```

```
Ala Arg Phe Gly Lys Glu Leu Cys Arg Gly Leu Pro Val Asp Ile Arg
        195                 200                 205

Leu Ala Asp Tyr Arg Thr Ala Thr Gly Glu Tyr Asp Arg Val Val Ser
    210                 215                 220

Ile Gly Leu Met Glu His Val Gly Tyr Lys Asn Tyr Gly Thr Tyr Met
225                 230                 235                 240

Lys Leu Thr Asn Arg Leu Leu Arg Asp Asp Gly Ile Ala Leu Ile His
                245                 250                 255

Thr Ile Gly Ser Asn Ala Ser Cys Ser Ala Cys Asn Pro Trp Thr Ala
            260                 265                 270

Lys Tyr Ile Phe Pro Asn Gly Met Leu Pro Ser Ile Ala Gln Leu Gly
        275                 280                 285

Lys Ala Met Glu Asn Gln Phe Val Met Glu Asp Trp His Asn Phe Gly
    290                 295                 300

Glu Asp Tyr Asp Lys Thr Leu Met Ala Trp Tyr Glu Asn Phe Lys Gln
305                 310                 315                 320

Val Trp Pro Asn Leu Glu Asp Arg Tyr Ser Asp Arg Phe Tyr Arg Met
                325                 330                 335

Trp Glu Tyr Tyr Leu Leu Ser Cys Ala Gly Gly Phe Arg Ser Arg Ser
            340                 345                 350

Met Gln Leu Trp Gln Ile Val Met Thr Lys Gln Gly Thr Ser Ala Pro
        355                 360                 365

Cys Cys Arg Leu Val
        370

<210> SEQ ID NO 9
<211> LENGTH: 1122
<212> TYPE: DNA
<213> ORGANISM: Unknown
<220> FEATURE:
<223> OTHER INFORMATION: Desulfobacter phenolica

<400> SEQUENCE: 9
atgaataatg ataaggtaaa atatactttt catggtctga tggatatggc gggaattaag      60
gttaacgggc cacgtcccta tgatatccag gttaaaaatg ataatttgta ccaaagggta     120
ttgagcaaag ccgcactggg gcttggcgag tcctacatgg atcaatggtg ggaatgcaaa     180
gcccttgaca ggtttattga taaaattctt cgtgcagatc ttgtaaacaa gattcgtcag     240
gactggaaca ccacatggga aattttaaaa gccagaatta ttaacctgca gaaacctgat     300
cgtgcattca tggtaggtca aaaacattat gatgtcggca atgacctttta ccaagccatg     360
ctcgacaaaa gaatgcagta tacctgcggc tattgggagg cggcagacac ccttgaatcg     420
gcccagaaag ccaaactgga actggtatgc aggaaaatcg gcctgaagcc gggaatgaag     480
gtgttggaac ttggatgcgg gtttggcggt tttgcacggt atgccgctca aaaatatgat     540
gcccatgtca ctggatttac agtgtccagg gaacaggctg cgttttcaaa aaacagtgc      600
aggggcctgc ccgttgatat ccggctcgat gactacagga acgcatcagg ttgtatgac      660
agggttgttt ccatagggat gatggaacat gtcgggtaca agaactacag ggcctatatg     720
gaactgacaa atcgtctgct caaggatgaa ggaattgctt tgttcatac cattggcagc      780
aatgtcagcc gtaaaatttg caatccctgg acggtcaagt atatttttcc caattcctcc     840
ctgccatcca tagcttttct ggggaaagca atgaagggc tttttgtggt ggaagattgg      900
cataattttg gtgaggatta cgataaaacc ctgatggcct ggcatgagaa ttttaaaaaa     960
```

```
gcctggccag gtctgaaaga aaaatacgat gaacggtttt acaggatgtg gacatattat  1020
cttttaagct gtgccggcgg attccgttca cgaagcatgc aattatggca gattgtaatg  1080
accaaacccg gcaggacccg tccggactgc cggataaatt ga                     1122
```

<210> SEQ ID NO 10
<211> LENGTH: 373
<212> TYPE: PRT
<213> ORGANISM: Unknown
<220> FEATURE:
<223> OTHER INFORMATION: Desulfobacter phenolica

<400> SEQUENCE: 10

```
Met Asn Asn Asp Lys Val Lys Tyr Thr Phe His Gly Leu Met Asp Met
1               5                   10                  15

Ala Gly Ile Lys Val Asn Gly Pro Arg Pro Tyr Asp Ile Gln Val Lys
            20                  25                  30

Asn Asp Asn Leu Tyr Gln Arg Val Leu Ser Lys Ala Ala Leu Gly Leu
        35                  40                  45

Gly Glu Ser Tyr Met Asp Gln Trp Trp Glu Cys Lys Ala Leu Asp Arg
    50                  55                  60

Phe Ile Asp Lys Ile Leu Arg Ala Asp Leu Val Asn Lys Ile Arg Gln
65                  70                  75                  80

Asp Trp Asn Thr Thr Trp Glu Ile Leu Lys Ala Arg Ile Ile Asn Leu
                85                  90                  95

Gln Lys Pro Asp Arg Ala Phe Met Val Gly Gln Lys His Tyr Asp Val
            100                 105                 110

Gly Asn Asp Leu Tyr Gln Ala Met Leu Asp Lys Arg Met Gln Tyr Thr
        115                 120                 125

Cys Gly Tyr Trp Glu Ala Ala Asp Thr Leu Glu Ser Ala Gln Lys Ala
    130                 135                 140

Lys Leu Glu Leu Val Cys Arg Lys Ile Gly Leu Lys Pro Gly Met Lys
145                 150                 155                 160

Val Leu Glu Leu Gly Cys Gly Phe Gly Gly Phe Ala Arg Tyr Ala Ala
                165                 170                 175

Gln Lys Tyr Asp Ala His Val Thr Gly Phe Thr Val Ser Arg Glu Gln
            180                 185                 190

Ala Ala Phe Ser Lys Lys Gln Cys Arg Gly Leu Pro Val Asp Ile Arg
        195                 200                 205

Leu Asp Asp Tyr Arg Asn Ala Ser Gly Leu Tyr Asp Arg Val Val Ser
    210                 215                 220

Ile Gly Met Met Glu His Val Gly Tyr Lys Asn Tyr Arg Ala Tyr Met
225                 230                 235                 240

Glu Leu Thr Asn Arg Leu Leu Lys Asp Glu Gly Ile Ala Phe Val His
                245                 250                 255

Thr Ile Gly Ser Asn Val Ser Arg Lys Ile Cys Asn Pro Trp Thr Val
            260                 265                 270

Lys Tyr Ile Phe Pro Asn Ser Ser Leu Pro Ser Ile Ala Phe Leu Gly
        275                 280                 285

Lys Ala Met Glu Gly Leu Phe Val Val Glu Asp Trp His Asn Phe Gly
    290                 295                 300

Glu Asp Tyr Asp Lys Thr Leu Met Ala Trp His Glu Asn Phe Lys Lys
305                 310                 315                 320

Ala Trp Pro Gly Leu Lys Glu Lys Tyr Asp Glu Arg Phe Tyr Arg Met
                325                 330                 335
```

Trp Thr Tyr Tyr Leu Leu Ser Cys Ala Gly Gly Phe Arg Ser Arg Ser
            340                 345                 350

Met Gln Leu Trp Gln Ile Val Met Thr Lys Pro Gly Arg Thr Arg Pro
        355                 360                 365

Asp Cys Arg Ile Asn
    370

<210> SEQ ID NO 11
<211> LENGTH: 1122
<212> TYPE: DNA
<213> ORGANISM: Desulfobacula toluolica

<400> SEQUENCE: 11

```
atgaataatg ataaggtaaa acatactttt catggtctga tggatatggc gggaattaag      60
gttaacgggc cacgtcccta tgatatccag gttaaaaatg ataatttgta ccaaagggta     120
ttgagcaaag ccgcactggg acttggcgag tcctacatgg atcaatggtg gaatgcaaa      180
gcccttgaca ggtttattga taaaattctt cgtgcagatc ttgtaaacaa gattcgtcag     240
gactggaaca ccacatggga aatttttaaaa gccagaatta ttaacctgca gaaacctgat   300
cgtgcattca tggtaggtca aaaacattat gatgtcggca atgaccttta ccaggccatg    360
ctcgacaaaa gaatgcagta tacctgcggc tattgggaga cggcagacac ccttgaatcg    420
gcccagaaag ccaaactgga actggtatgc aggaaaatcg gcctgaagcc gggaatgaag    480
gtgttggaac ttggatgcgg gtttggcggg tttgcacggt atgccgctca aaatatgat     540
gcccatgtca ctggatttac agtgtccagg gaacaggctg cgtttgcaaa aaaacagtgc    600
aggggcctgc ccgttgatat ccggctcgat gattacagga acgcatcagg ttgtatgac    660
agggttgttt ccatagggat gatggagcat gtcgggtaca agaactacag ggcctatatg    720
gaactgacaa atcgtctgct caaggatgaa ggcattgctt ttgttcatac cattggcagc    780
aatgtcagcc gtaaaatttg caatccctgg acggtcaagt atattttttcc caattcctcc    840
ctgccatcca tagcttttct ggggaaagcc atggaagggc ttttgtggt ggaagattgg     900
cataattttg gtgaggatta cgataaaacc ctgatggcct ggcatgagaa ttttaaaaaa    960
gcctggccag gtctgaaaga aaaatacgat gaacggtttt acaggatgtg gacatattat   1020
cttttaagct gtgccggcgg attccgttca cgaagcatgc aattatggca gattgtaatg   1080
accaaacccg gcaggacccg tccggaccgc cggataaatt ga                       1122
```

<210> SEQ ID NO 12
<211> LENGTH: 373
<212> TYPE: PRT
<213> ORGANISM: Desulfobacula toluolica

<400> SEQUENCE: 12

Met Asn Asn Asp Lys Val Lys His Thr Phe His Gly Leu Met Asp Met
1               5                   10                  15

Ala Gly Ile Lys Val Asn Gly Pro Arg Pro Tyr Asp Ile Gln Val Lys
            20                  25                  30

Asn Asp Asn Leu Tyr Gln Arg Val Leu Ser Lys Ala Ala Leu Gly Leu
        35                  40                  45

Gly Glu Ser Tyr Met Asp Gln Trp Trp Glu Cys Lys Ala Leu Asp Arg
    50                  55                  60

Phe Ile Asp Lys Ile Leu Arg Ala Asp Leu Val Asn Lys Ile Arg Gln
65                  70                  75                  80

Asp Trp Asn Thr Thr Trp Glu Ile Leu Lys Ala Arg Ile Ile Asn Leu
             85                  90                  95

Gln Lys Pro Asp Arg Ala Phe Met Val Gly Gln Lys His Tyr Asp Val
        100                 105                 110

Gly Asn Asp Leu Tyr Gln Ala Met Leu Asp Lys Arg Met Gln Tyr Thr
    115                 120                 125

Cys Gly Tyr Trp Glu Thr Ala Asp Thr Leu Glu Ser Ala Gln Lys Ala
130                 135                 140

Lys Leu Glu Leu Val Cys Arg Lys Ile Gly Leu Lys Pro Gly Met Lys
145                 150                 155                 160

Val Leu Glu Leu Gly Cys Gly Phe Gly Gly Phe Ala Arg Tyr Ala Ala
                165                 170                 175

Gln Lys Tyr Asp Ala His Val Thr Gly Phe Thr Val Ser Arg Glu Gln
            180                 185                 190

Ala Ala Phe Ala Lys Lys Gln Cys Arg Gly Leu Pro Val Asp Ile Arg
        195                 200                 205

Leu Asp Asp Tyr Arg Asn Ala Ser Gly Leu Tyr Asp Arg Val Val Ser
    210                 215                 220

Ile Gly Met Met Glu His Val Gly Tyr Lys Asn Tyr Arg Ala Tyr Met
225                 230                 235                 240

Glu Leu Thr Asn Arg Leu Leu Lys Asp Glu Gly Ile Ala Phe Val His
                245                 250                 255

Thr Ile Gly Ser Asn Val Ser Arg Lys Ile Cys Asn Pro Trp Thr Val
            260                 265                 270

Lys Tyr Ile Phe Pro Asn Ser Ser Leu Pro Ser Ile Ala Phe Leu Gly
        275                 280                 285

Lys Ala Met Glu Gly Leu Phe Val Val Glu Asp Trp His Asn Phe Gly
    290                 295                 300

Glu Asp Tyr Asp Lys Thr Leu Met Ala Trp His Glu Asn Phe Lys Lys
305                 310                 315                 320

Ala Trp Pro Gly Leu Lys Glu Lys Tyr Asp Glu Arg Phe Tyr Arg Met
                325                 330                 335

Trp Thr Tyr Tyr Leu Leu Ser Cys Ala Gly Gly Phe Arg Ser Arg Ser
            340                 345                 350

Met Gln Leu Trp Gln Ile Val Met Thr Lys Pro Gly Arg Thr Arg Pro
        355                 360                 365

Asp Arg Arg Ile Asn
        370

<210> SEQ ID NO 13
<211> LENGTH: 1122
<212> TYPE: DNA
<213> ORGANISM: Desulfobacter postgatei

<400> SEQUENCE: 13
atgaaaaatc aggatatcaa gaaatccata cacaaattat tgaattttgc cggcatcacc      60
gttaacggaa gcaatcccta cgatattcag gtgaaaaatg accggtttta ccaacgaata     120
atccatgaac tgctctctgg gcttggtgaa gcatatatgg ataactggtg ggagtgccgt     180
gccctggatc agttcatcgc aaaagtgttg tgcgcaaacc ttggacaagt attaaaaaag     240
gagtggcgga tcacatggaa cctgttaacg gcaaagcttt ttaatcaaca gtcttccaag     300
cgtgccttta tggtgggcca acgccactat gacatcggca atgatcttta tcagggcatg     360
ctggacaaac aaatgcagta tacctgcgga tactggaaag atgccaccac ccttgatcag     420

```
gcccaggagg cgaaactggc actggtctgc cggaaattaa aactggaacc cggtatgaaa      480
gttcttgagc tgggatgcgg gtttggcggg tttgcccact atgcggcaac aaggtacggc      540
gttgaagtga ctggatacac cgtctccaaa gagcaggtca aatttgcaga aaaactatgc      600
aaagggcttc ctgttgatat ccggctggca gattacagaa ccgccaccgg agaatatgac      660
cgggtactct ccattggttt aatggagcat gtggggtata aaattatgg cacttacatg       720 aaactgacca atcggttgct aagggatgac ggcattgctt tggttcatac catcggtcgt      780
aatgatagtc gttgtgcctg caactcatgg actgcaaaat atattttccc caatggcatg      840
cttccctcca ttgcccagtt gggaaaagcc atggaaaacc aatttgtcat ggaggactgg      900
cataactttg gagaggacta cgataaaaca ttaatggcat ggtacgaaaa tttcagacag      960
gtgtggccca aacttaaaga tagatacaac gatcggtttt atcgcatgtg ggagtattat      1020
ctgttaagct gtgccggagg atttcggtct cgatccatgc agttatggca gattgtgatg      1080
actaaacagg gaacttcagc gccctgttgt cgccttgtgt aa                          1122
```

<210> SEQ ID NO 14
<211> LENGTH: 373
<212> TYPE: PRT
<213> ORGANISM: Desulfobacter postgatei

<400> SEQUENCE: 14

```
Met Lys Asn Gln Asp Ile Lys Lys Ser Ile His Lys Leu Leu Asn Phe
1               5                   10                  15

Ala Gly Ile Thr Val Asn Gly Ser Asn Pro Tyr Asp Ile Gln Val Lys
            20                  25                  30

Asn Asp Arg Phe Tyr Gln Arg Ile Ile His Glu Pro Ala Leu Gly Leu
        35                  40                  45

Gly Glu Ala Tyr Met Asp Asn Trp Trp Glu Cys Arg Ala Leu Asp Gln
    50                  55                  60

Phe Ile Ala Lys Val Leu Cys Ala Asn Leu Gly Gln Val Leu Lys Lys
65                  70                  75                  80

Glu Trp Arg Ile Thr Trp Asn Leu Leu Thr Ala Lys Leu Phe Asn Gln
                85                  90                  95

Gln Ser Ser Lys Arg Ala Phe Met Val Gly Gln Arg His Tyr Asp Ile
            100                 105                 110

Gly Asn Asp Leu Tyr Gln Gly Met Leu Asp Lys Gln Met Gln Tyr Thr
        115                 120                 125

Cys Gly Tyr Trp Lys Asp Ala Thr Thr Leu Asp Gln Ala Gln Glu Ala
    130                 135                 140

Lys Leu Ala Leu Val Cys Arg Lys Leu Lys Leu Glu Pro Gly Met Lys
145                 150                 155                 160

Val Leu Glu Leu Gly Cys Gly Phe Gly Gly Phe Ala His Tyr Ala Ala
                165                 170                 175

Thr Arg Tyr Gly Val Glu Val Thr Gly Tyr Thr Val Ser Lys Glu Gln
            180                 185                 190

Val Lys Phe Ala Glu Lys Leu Cys Lys Gly Leu Pro Val Asp Ile Arg
        195                 200                 205

Leu Ala Asp Tyr Arg Thr Ala Thr Gly Glu Tyr Asp Arg Val Leu Ser
    210                 215                 220

Ile Gly Leu Met Glu His Val Gly Tyr Lys Asn Tyr Gly Thr Tyr Met
225                 230                 235                 240
```

```
Lys Leu Thr Asn Arg Leu Leu Arg Asp Asp Gly Ile Ala Leu Val His
            245                 250                 255

Thr Ile Gly Arg Asn Asp Ser Arg Cys Ala Cys Asn Ser Trp Thr Ala
        260                 265                 270

Lys Tyr Ile Phe Pro Asn Gly Met Leu Pro Ser Ile Ala Gln Leu Gly
        275                 280                 285

Lys Ala Met Glu Asn Gln Phe Val Met Glu Asp Trp His Asn Phe Gly
        290                 295                 300

Glu Asp Tyr Asp Lys Thr Leu Met Ala Trp Tyr Glu Asn Phe Arg Gln
305                 310                 315                 320

Val Trp Pro Lys Leu Lys Asp Arg Tyr Asn Asp Arg Phe Tyr Arg Met
                325                 330                 335

Trp Glu Tyr Tyr Leu Leu Ser Cys Ala Gly Gly Phe Arg Ser Arg Ser
            340                 345                 350

Met Gln Leu Trp Gln Ile Val Met Thr Lys Gln Gly Thr Ser Ala Pro
        355                 360                 365

Cys Cys Arg Leu Val
        370

<210> SEQ ID NO 15
<211> LENGTH: 1329
<212> TYPE: DNA
<213> ORGANISM: Unknown
<220> FEATURE:
<223> OTHER INFORMATION: Halofilum ochraceum

<400> SEQUENCE: 15
atggatgaca acacgtctat ccagcaggag tcggcctcgg agccggcgca gcgggcgaat        60 ccccttccc tgcccacggg gcaccgccgt tccatgagcg gccccgcgc gcccgagcgc        120 tgggtggccg tgcagttgct gaacctcgcc ggcagtccgc cggtggcgat cgaactctgg        180
aacggcgaac gggttcatcc ggcggccggt ggcacgccgc ggttcacgct gcgtatcggt        240
gaccgcaagg ccctgtacgg catgctcagc aatccgaatc tcgcgttcgg cgacctctac        300
agcgccgggc gcatcgatgt cgacggtgac ctcgcggaat tcctgaccga ggtcacggcc        360
cacgtcgagc gacagcaggc gcgcatgccg gcatccgcgc gctggctggg gcgcggccgc        420
gcgaccccga aggcggccag cgagcgagcg gccaagggca acatccagca ccactatgac        480
ctcggcaacg acttctatcg tctgtggctc gaccgggcgg cgatgcagta cacctgtgcc        540
tattacgaag aacccgagct gacgctcgaa caggcgcaac aggcgaaact cgagcacgtg        600
tgccgcaagc tggcactcca gcctggccaa cgggtcgtgg agcttggctg tggctggggc        660
gggctggcgc ggtacatggc ccgcgaatac ggggtcagcg tgcgcgcgtt caacatctcc        720
cgggaacagg tggagtatgc ccgtgagcag gcggcccgtg agggcctcga tgatcgcatc        780
gagtacgtgc tggacgatta ccgcaacatc tccggcgagt atgacgcctt cgtctcggta        840
ggcatgctcg agcatgtcgg cacggacaat tacgccacgg tggcgcggct gatccgcaac        900
cacctccgcc cggacgggct cgcgctgatt cacacgatcg ggcgcaaccg gccggcgggg        960
atcaacgcgt ggatcgagaa gcgcatcttc ccgggcgcgt atccgcccag catcacgcaa       1020
ctgaccggac tcgccgaggc cgggccgctg tccgtgctcg acatcgagaa cctgcgcctg       1080
cattacgcga gacactgac ggactggctg gcccgctacg aggacaacat cgaccaggtc       1140
cgcgcgatgt acgacgaaca cttcgcgcgc gcctggcggc tgtatctctc gggctcgatc       1200
```

```
gcggccttcc gggccggcac gctgcagttg ttccagatgg tgctcgcgca cccggataac    1260
aacggcatcc cgcgcaaccg caagcgcctt catacagcgc cggcataccc ggaggagccc    1320
gcggcatga                                                            1329
```

```
<210> SEQ ID NO 16
<211> LENGTH: 442
<212> TYPE: PRT
<213> ORGANISM: Unknown
<220> FEATURE:
<223> OTHER INFORMATION: Halofilum ochraceum

<400> SEQUENCE: 16
```

```
Met Asp Asp Asn Thr Ser Ile Gln Gln Glu Ser Ala Ser Glu Pro Ala
1               5                   10                  15

Gln Arg Ala Asn Pro Leu Ser Leu Pro Thr Gly His Arg Arg Ser Met
            20                  25                  30

Ser Gly Pro Arg Ala Pro Glu Arg Trp Val Ala Val Gln Leu Leu Asn
        35                  40                  45

Leu Ala Gly Ser Pro Val Ala Ile Glu Leu Trp Asn Gly Glu Arg
    50                  55                  60

Val His Pro Ala Ala Gly Gly Thr Pro Arg Phe Thr Leu Arg Ile Gly
65                  70                  75                  80

Asp Arg Lys Ala Leu Tyr Gly Met Leu Ser Asn Pro Asn Leu Ala Phe
                85                  90                  95

Gly Asp Leu Tyr Ser Ala Gly Arg Ile Asp Val Asp Gly Asp Leu Ala
            100                 105                 110

Glu Phe Leu Thr Glu Val Thr Ala His Val Glu Arg Gln Gln Ala Arg
        115                 120                 125

Met Pro Ala Ser Ala Arg Trp Leu Gly Arg Gly Arg Ala Thr Pro Lys
    130                 135                 140

Ala Ala Ser Glu Arg Ala Ala Lys Gly Asn Ile Gln His His Tyr Asp
145                 150                 155                 160

Leu Gly Asn Asp Phe Tyr Arg Leu Trp Leu Asp Arg Ala Ala Met Gln
                165                 170                 175

Tyr Thr Cys Ala Tyr Tyr Glu Glu Pro Glu Leu Thr Leu Glu Gln Ala
            180                 185                 190

Gln Gln Ala Lys Leu Glu His Val Cys Arg Lys Leu Ala Leu Gln Pro
        195                 200                 205

Gly Gln Arg Val Val Glu Leu Gly Cys Gly Trp Gly Gly Leu Ala Arg
    210                 215                 220

Tyr Met Ala Arg Glu Tyr Gly Val Ser Val Arg Ala Phe Asn Ile Ser
225                 230                 235                 240

Arg Glu Gln Val Glu Tyr Ala Arg Glu Gln Ala Arg Glu Gly Leu
                245                 250                 255

Asp Asp Arg Ile Glu Tyr Val Leu Asp Asp Tyr Arg Asn Ile Ser Gly
            260                 265                 270

Glu Tyr Asp Ala Phe Val Ser Val Gly Met Leu Glu His Val Gly Thr
        275                 280                 285

Asp Asn Tyr Ala Thr Val Ala Arg Leu Ile Arg Asn His Leu Arg Pro
    290                 295                 300

Asp Gly Leu Ala Leu Ile His Thr Ile Gly Arg Asn Arg Pro Ala Gly
305                 310                 315                 320

Ile Asn Ala Trp Ile Glu Lys Arg Ile Phe Pro Gly Ala Tyr Pro Pro
                325                 330                 335
```

```
Ser Ile Thr Gln Leu Thr Gly Leu Ala Glu Ala Gly Pro Leu Ser Val
            340                 345                 350

Leu Asp Ile Glu Asn Leu Arg Leu His Tyr Ala Glu Thr Leu Thr Asp
        355                 360                 365

Trp Leu Ala Arg Tyr Glu Asp Asn Ile Asp Gln Val Arg Ala Met Tyr
370                 375                 380

Asp Glu His Phe Ala Arg Ala Trp Arg Leu Tyr Leu Ser Gly Ser Ile
385                 390                 395                 400

Ala Ala Phe Arg Ala Gly Thr Leu Gln Leu Phe Gln Met Val Leu Ala
                405                 410                 415

His Pro Asp Asn Asn Gly Ile Pro Arg Asn Arg Lys Arg Leu His Thr
            420                 425                 430

Ala Pro Ala Tyr Pro Glu Glu Pro Ala Ala
            435                 440

<210> SEQ ID NO 17
<211> LENGTH: 1317
<212> TYPE: DNA
<213> ORGANISM: Unknown
<220> FEATURE:
<223> OTHER INFORMATION: Marinobacter aquaeolei

<400> SEQUENCE: 17
atggcacaga gtaccgctca taaaccggag ttaccggaca aggaggaaca ccgggcccac      60
gtcctcagcc tgcccctgga gcgcggtcaa tccgatcgcg aaccccacag ttatgaacgc     120
tggctgatcc ataaactgat gcgtatggcc ggctctcccc ccattcgttt ccggctctgg     180
aacggcgatg tcatagaacc ggaagttcag gacgcccgct tcaccctgca cctgaccgac     240
cacaaggctc tctactccct ggtggccaac cccaatctgg cctttggtga cctgtatgcc     300
gccggtcgac tggaaatcga cggcgatctt ccagatctga tggagagcct gtaccgggcc     360
gtccatgccg cccgccagaa atggccacgc tggctggacg ccctgtggcg caaccacaac     420
ccgcgtgcca ccggcatctc cgaggccaag gagaacattc accaccacta cgacctgggc     480
aacgcgtttt accaactgtg gctggatgag gccgaaatgc agtacacctg cgcctattac     540
gagcaggccg acaacaccct ggaacaggcg caactggcca aactggaaca cgtttgccgc     600
aagcttcggc tgaaaccggg catgaccgtg gtcgaagccg ctgcgggtg gggcgggctg     660 gcccgatata tggcccgtca ttacggagtg aaggtgcatt cctacaatat ctcactggaa     720
cagctggcct acgcccgggc tgaagcagag cgacaaggcc tggacaacct ggttacctat     780
gtcgaagacg actaccgcaa tattgagggc cagtatgacg cgttcgtttc tattggcatg     840
ctcgaacacg tgggcaagga caattacccc gctctgtcgg aactgatcaa cgctccctg     900 aagccgaatg gtattgcctt gctccacagc atcggccgca accggcccat gctgatgaac     960
gcctggatcg agaagcggat tttccccggc gcctatccgc ccagcattgg cgagttcatg    1020
gaaatctgcg agcacagcga tttctcggta ctggatgtgg aaaacctgcg gctgcattac    1080
gctcagaccc tgacccactg gatggacaat tcaccgcca accaggacca ggtcaccgag    1140
atgtacgaca acatttcac ccgggcctgg cgactgtatc tggccggttc catcgccgcg    1200
ttccgggccg gttctttgca gttgttccag gtggtgttca cccacggcga caataaccag    1260
ctgccccaga gccggcagga actctacacg tttacagcca cgccagaggg ggtctga      1317

<210> SEQ ID NO 18
<211> LENGTH: 438
```

<212> TYPE: PRT
<213> ORGANISM: Unknown
<220> FEATURE:
<223> OTHER INFORMATION: Marinobacter aquaeolei

<400> SEQUENCE: 18

Met Ala Gln Ser Thr Ala His Lys Pro Glu Leu Pro Asp Lys Glu Glu
1               5                   10                  15

His Arg Ala His Val Leu Ser Leu Pro Leu Glu Arg Gly Gln Ser Asp
            20                  25                  30

Arg Glu Pro His Ser Tyr Glu Arg Trp Leu Ile His Lys Leu Met Arg
        35                  40                  45

Met Ala Gly Ser Pro Pro Ile Arg Phe Arg Leu Trp Asn Gly Asp Val
50                  55                  60

Ile Glu Pro Glu Val Gln Asp Ala Arg Phe Thr Leu His Leu Thr Asp
65                  70                  75                  80

His Lys Ala Leu Tyr Ser Leu Val Ala Asn Pro Asn Leu Ala Phe Gly
                85                  90                  95

Asp Leu Tyr Ala Ala Gly Arg Leu Glu Ile Asp Gly Asp Leu Pro Asp
            100                 105                 110

Leu Met Glu Ser Leu Tyr Arg Ala Val His Ala Ala Arg Gln Lys Trp
        115                 120                 125

Pro Arg Trp Leu Asp Ala Leu Trp Arg Asn His Asn Pro Arg Ala Thr
130                 135                 140

Gly Ile Ser Glu Ala Lys Glu Asn Ile His His Tyr Asp Leu Gly
145                 150                 155                 160

Asn Ala Phe Tyr Gln Leu Trp Leu Asp Glu Ala Glu Met Gln Tyr Thr
                165                 170                 175

Cys Ala Tyr Tyr Glu Gln Ala Asp Asn Thr Leu Glu Gln Ala Gln Leu
            180                 185                 190

Ala Lys Leu Glu His Val Cys Arg Lys Leu Arg Leu Lys Pro Gly Met
        195                 200                 205

Thr Val Val Glu Ala Gly Cys Gly Trp Gly Gly Leu Ala Arg Tyr Met
210                 215                 220

Ala Arg His Tyr Gly Val Lys Val His Ser Tyr Asn Ile Ser Leu Glu
225                 230                 235                 240

Gln Leu Ala Tyr Ala Arg Ala Glu Ala Glu Arg Gln Gly Leu Asp Asn
                245                 250                 255

Leu Val Thr Tyr Val Glu Asp Asp Tyr Arg Asn Ile Glu Gly Gln Tyr
            260                 265                 270

Asp Ala Phe Val Ser Ile Gly Met Leu Glu His Val Gly Lys Asp Asn
        275                 280                 285

Tyr Pro Ala Leu Ser Glu Leu Ile Lys Arg Ser Leu Lys Pro Asn Gly
290                 295                 300

Ile Ala Leu Leu His Ser Ile Gly Arg Asn Arg Pro Met Leu Met Asn
305                 310                 315                 320

Ala Trp Ile Glu Lys Arg Ile Phe Pro Gly Ala Tyr Pro Pro Ser Ile
                325                 330                 335

Gly Glu Phe Met Glu Ile Cys Glu His Ser Asp Phe Ser Val Leu Asp
            340                 345                 350

Val Glu Asn Leu Arg Leu His Tyr Ala Gln Thr Leu Thr His Trp Met
        355                 360                 365

Asp Asn Phe Thr Ala Asn Gln Asp Gln Val Thr Glu Met Tyr Asp Glu
370                 375                 380

His Phe Thr Arg Ala Trp Arg Leu Tyr Leu Ala Gly Ser Ile Ala Ala
385                 390                 395                 400

Phe Arg Ala Gly Ser Leu Gln Leu Phe Gln Val Val Phe Thr His Gly
            405                 410                 415

Asp Asn Asn Gln Leu Pro Gln Ser Arg Gln Glu Leu Tyr Thr Phe Thr
        420                 425                 430

Ala Thr Pro Glu Gly Val
        435

<210> SEQ ID NO 19
<211> LENGTH: 978
<212> TYPE: DNA
<213> ORGANISM: Unknown
<220> FEATURE:
<223> OTHER INFORMATION: Desulfobacula balticum

<400> SEQUENCE: 19

```
atgattcaga cggatgtgat cattgtgggc gggggcccgg ccggatccgc ctgtgcggcc      60
cgtctcaaaa aaaccggaat ggatgtcagg atactggaca acaaaggtt tcccaggaaa     120
aaactgtgtg ccggatggat ctcacccggg gtgtttgatg acctgggata cgaccctgat    180
acctatcccc acgccttgac ccggatccac gggattcact tcacctgtt tcaggttcct    240
ttgcccgtgc gaacgcacca gtatgcaatc ggcgcatcg agttcgacca ctggctgctc    300
cagaaggccg ggtgcccgt gcacacccat gccgtaaaaa aaattcaaag aatccggtcc    360
gggtatgtca tcgatgacca gtttgaatgc cggtacctgg tcggggccgg cggcacccat    420
tgcccggtgc ggcgcacttt tatggaacct gtgccgtccc gtccggaaac cgcccgcatc    480
gccgccgtgg aaaaagagtt tcaaggcttt caacgggtcc ggaagtgtca tatctggtat    540
ctggaaaaag gcctgcccgg atatgcgtgg tacctgccca aaaaggcgg gtggatcaac    600
atcggcatcg gcggcaaaca gcacggcctg accgcccgga aaaccaccat catggatcac    660
tggcgcacat ttgtggcccg cctgatggat aaaggctttc tggaccaatc cccgggcaat    720
ccctccgggc atacctatta tctgcggcat acaccttatc accggcaaac tttggaaaac    780
agcatgccgg acaatctgtt tgtcatcggc gatgctgccg gcctgtccac cctggacatg    840
ggggaaggca tccatgcggc cgtccagagc ggcattgccg cggctgacgc cattattgcc    900
ggccgtccca tgcaggtgag ccacatctcc cggttcagcc tgccgggcct ggtgaagtcc    960
ggattccgtt ccgcttaa                                                   978
```

<210> SEQ ID NO 20
<211> LENGTH: 325
<212> TYPE: PRT
<213> ORGANISM: Unknown
<220> FEATURE:
<223> OTHER INFORMATION: Desulfobacula balticum

<400> SEQUENCE: 20

Met Ile Gln Thr Asp Val Ile Val Gly Gly Gly Pro Gly Ser
1               5                   10                  15

Ala Cys Ala Ala Arg Leu Lys Lys Thr Gly Met Asp Val Arg Ile Leu
            20                  25                  30

Asp Lys Gln Arg Phe Pro Arg Lys Lys Leu Cys Ala Gly Trp Ile Ser
        35                  40                  45

Pro Gly Val Phe Asp Asp Leu Gly Tyr Asp Pro Asp Thr Tyr Pro His
    50                  55                  60

```
Ala Leu Thr Arg Ile His Gly Ile His Phe His Leu Phe Gln Val Pro
 65                  70                  75                  80

Leu Pro Val Arg Thr His Gln Tyr Ala Ile Arg Arg Ile Glu Phe Asp
                 85                  90                  95

His Trp Leu Leu Gln Lys Ala Gly Val Pro Val His Thr His Ala Val
            100                 105                 110

Lys Lys Ile Gln Arg Ile Arg Ser Gly Tyr Val Ile Asp Asp Gln Phe
        115                 120                 125

Glu Cys Arg Tyr Leu Val Gly Ala Gly Thr His Cys Pro Val Arg
130                 135                 140

Arg Thr Phe Met Glu Pro Val Pro Ser Arg Pro Glu Thr Ala Arg Ile
145                 150                 155                 160

Ala Ala Val Glu Lys Glu Phe Gln Gly Phe Gln Arg Val Arg Lys Cys
                165                 170                 175

His Ile Trp Tyr Leu Glu Lys Gly Leu Pro Gly Tyr Ala Trp Tyr Leu
            180                 185                 190

Pro Lys Lys Gly Gly Trp Ile Asn Ile Gly Ile Gly Lys Gln His
        195                 200                 205

Gly Leu Thr Ala Arg Lys Thr Thr Ile Met Asp His Trp Arg Thr Phe
        210                 215                 220

Val Ala Arg Leu Met Asp Lys Gly Phe Leu Asp Gln Ser Pro Gly Asn
225                 230                 235                 240

Pro Ser Gly His Thr Tyr Tyr Leu Arg His Thr Pro Tyr His Arg Gln
                245                 250                 255

Thr Leu Glu Asn Ser Met Pro Asp Asn Leu Phe Val Ile Gly Asp Ala
            260                 265                 270

Ala Gly Leu Ser Thr Leu Asp Met Gly Glu Gly Ile His Ala Ala Val
        275                 280                 285

Gln Ser Gly Ile Ala Ala Ala Asp Ala Ile Ile Ala Gly Arg Pro Met
        290                 295                 300

Gln Val Ser His Ile Ser Arg Phe Ser Leu Pro Gly Leu Val Lys Ser
305                 310                 315                 320

Gly Phe Arg Ser Ala
                325

<210> SEQ ID NO 21
<211> LENGTH: 1125
<212> TYPE: DNA
<213> ORGANISM: Marinobacter hydrocarbonoclasticus

<400> SEQUENCE: 21
atggatcact acgatgtgat cattgttggt gccggcccgg ccggttccac cctggcacgc     60
agcttggagg atgccgggaa gaatgtactg gtcatcgaca agccagcttt cccccgggac    120
aaaacctgcg cgggctgggt aacacctgcc gttatggaga gcctggacat caacccggcg    180
aattacgcca atggccgaac ccttcagcct attcgtcgtt ccgcattggc atgatgggg     240 cagcctgcgg tggagaacga ccaccatggc attgtcagtt acggcatacg cgctgcgaa     300 ttcgacgctt cctgctcga gcgggtacgc tctccaaagc aacttgccac acccgtcaaa    360
tccatcgtcc ggaacaacgg ccactgggtg gtcaacaacc agtggcaggc cccgcttctg    420
attggcgccg gggggcactt ctgcccggtt gccagacagc tgggcactgg ccccggtaaa    480
cacgaaacag tggtcgccgc caaggaagtg gagtttgaga tgacaccgga acaggccgat    540
gcctgtgaag cccggggga  tacacctgag ctctggttct gccgggatct caagggttat    600
```

```
gcctgggtat tccgcaaagg taatttcctg aacattggcc tggggcggga agacaaccac    660
cggctaacgg atcacctgga ggcattcgta gacgatatga agcacgacgg gcgaatcccc    720
gcagacctgc cggggcgatt caaaggccat gcctacctgt tgtacgccca tgcagatcgg    780
ccactggtag acgacggcgt attgctgatc ggagatgcag cgggcctggc ttacacccag    840
agcggtgagg gtatccgccc tgccattgaa tccgccttga tggcggccga ggtgattctt    900
aacgccacag attttctgc cgccgcgcta cagcgctacg gtgagcgcat tgcggaacgc    960
tttggcaacc gtgccagtga gcaggcagct ggctgggaac tgccggaatg gctgaagcag    1020
cccgtcgcca gcacattgat gcgctcacac tggtttaccc gaaaggtagt gacggagaaa    1080
tggttcctgc atcaggatgt gcctaccctg aaagccgtcg gctga                    1125
```

<210> SEQ ID NO 22
<211> LENGTH: 374
<212> TYPE: PRT
<213> ORGANISM: Marinobacter hydrocarbonoclasticus

<400> SEQUENCE: 22

```
Met Asp His Tyr Asp Val Ile Ile Val Gly Ala Gly Pro Ala Gly Ser
1               5                   10                  15

Thr Leu Ala Arg Ser Leu Glu Asp Ala Gly Lys Asn Val Leu Val Ile
            20                  25                  30

Asp Lys Ala Ser Phe Pro Arg Asp Lys Thr Cys Ala Gly Trp Val Thr
        35                  40                  45

Pro Ala Val Met Glu Ser Leu Asp Ile Asn Pro Ala Asn Tyr Ala Asn
    50                  55                  60

Gly Arg Thr Leu Gln Pro Ile Arg Arg Phe Arg Ile Gly Met Met Gly
65                  70                  75                  80

Gln Pro Ala Val Glu Asn Asp His His Gly Ile Val Ser Tyr Gly Ile
                85                  90                  95

Arg Arg Cys Glu Phe Asp Ala Phe Leu Leu Glu Arg Val Arg Ser Pro
            100                 105                 110

Lys Gln Leu Ala Thr Pro Val Lys Ser Ile Val Arg Asn Asn Gly His
        115                 120                 125

Trp Val Val Asn Asn Gln Trp Gln Ala Pro Leu Leu Ile Gly Ala Gly
    130                 135                 140

Gly His Phe Cys Pro Val Ala Arg Gln Leu Gly Thr Gly Pro Gly Lys
145                 150                 155                 160

His Glu Thr Val Val Ala Ala Lys Glu Val Glu Phe Glu Met Thr Pro
                165                 170                 175

Glu Gln Ala Asp Ala Cys Glu Ala Arg Gly Asp Thr Pro Glu Leu Trp
            180                 185                 190

Phe Cys Arg Asp Leu Lys Gly Tyr Ala Trp Val Phe Arg Lys Gly Asn
        195                 200                 205

Phe Leu Asn Ile Gly Leu Gly Arg Glu Asp Asn His Arg Leu Thr Asp
    210                 215                 220

His Leu Glu Ala Phe Val Asp Asp Met Lys His Asp Gly Arg Ile Pro
225                 230                 235                 240

Ala Asp Leu Pro Gly Arg Phe Lys Gly His Ala Tyr Leu Leu Tyr Ala
                245                 250                 255

His Ala Asp Arg Pro Leu Val Asp Asp Gly Val Leu Leu Ile Gly Asp
            260                 265                 270
```

Ala Ala Gly Leu Ala Tyr Thr Gln Ser Gly Glu Gly Ile Arg Pro Ala
        275                 280                 285

Ile Glu Ser Ala Leu Met Ala Ala Glu Val Ile Leu Asn Ala Thr Asp
        290                 295                 300

Phe Ser Ala Ala Ala Leu Gln Arg Tyr Gly Arg Ile Ala Glu Arg
305                 310                 315                 320

Phe Gly Asn Arg Ala Ser Glu Gln Ala Ala Gly Trp Glu Leu Pro Glu
                325                 330                 335

Trp Leu Lys Gln Pro Val Ala Ser Thr Leu Met Arg Ser His Trp Phe
                340                 345                 350

Thr Arg Lys Val Val Thr Glu Lys Trp Phe Leu His Gln Asp Val Pro
        355                 360                 365

Thr Leu Lys Ala Val Gly
        370

<210> SEQ ID NO 23
<211> LENGTH: 1128
<212> TYPE: DNA
<213> ORGANISM: Unknown
<220> FEATURE:
<223> OTHER INFORMATION: Thiohalospira halophila

<400> SEQUENCE: 23

```
atgagcgaac gcagcgacgt cctcatcgtc ggcggcggtc ccggcggttc caccctgggt      60
cgggcgctcg ctcggcaggg cctggatgtg accatcgtcg acaagcagac cttcccccgg     120
gacaaggtct cgccggctg gtgaccccc gcggtcatgg agtccctgga cctggacccg     180
aacgaatacg cccgggatgc cgtcctgcag cccatccacg cctttcgcac cggcatgctc     240
ggtcagcgca ccgtggtctc tcgctacccg gaaccggcga gttacgggat ccggcgctac     300
gagttcgatg cctggctgct ggaacgggcc atcaacgacg tgtccgtac cgcgcagggc     360
cagcctctga aagagctgcg ccgggaagac ggtgagtggg tgctcaatga ccatctgcgc     420
acaccgctgc tcatcggtgc cggcggccac ttctgtcccg tggcgcgcca cctcggggcg     480
gcgaagcccg ctcctcgga gaccgcggtc acgcccagg agatcgagtt cgagatgacg     540
ccggagcagg cggctgcctg tccggtggag gccgacgtgc ggagctcta cttcctccgc     600
gacctctccg gctacggctg gatcgtgcgc aaggggact ggctgaatat cggcctcggt     660
cgcgaggggg gccagaagct cggtgagcag gtaagcgcct tcgccgagga gctcaaggcc     720
atggggcggc tccacatcga cccaccgagc aagttcaagg ccacgccta cctgctccac     780
ggccacagcc gcggccgcc ggttcacgac ggggccctgc tcatcggtga gcagccggc     840
ctggcctatc gcagagcgg cgaggggatc cggccggcag tggagtccgc gctcatggcg     900
gcggaggtca ttggtgccgc gggtggcgat tacagtgccg accgcctggc cgccttcggc     960
gaccggctac agcgccgctt cggcaagggg tcggcggcgg gtgaacccgg gccggtgaaa    1020
caggccctgg cgcggccgct catggcctcg agctggttcg cccgccacgt catcctcgac    1080
cgttggttcc tccaccgcca ccaggccccc ttggccccgg cggcctga                 1128
```

<210> SEQ ID NO 24
<211> LENGTH: 375
<212> TYPE: PRT
<213> ORGANISM: Unknown
<220> FEATURE:
<223> OTHER INFORMATION: Thiohalospira halophila

<400> SEQUENCE: 24

```
Met Ser Glu Arg Ser Asp Val Leu Ile Val Gly Gly Pro Gly Gly
1               5                   10                  15

Ser Thr Leu Gly Arg Ala Leu Ala Arg Gln Gly Leu Asp Val Thr Ile
            20                  25                  30

Val Asp Lys Gln Thr Phe Pro Arg Asp Lys Val Cys Ala Gly Trp Val
        35                  40                  45

Thr Pro Ala Val Met Glu Ser Leu Asp Leu Asp Pro Asn Glu Tyr Ala
    50                  55                  60

Arg Asp Ala Val Leu Gln Pro Ile His Ala Phe Arg Thr Gly Met Leu
65                  70                  75                  80

Gly Gln Arg Thr Val Val Ser Arg Tyr Pro Glu Pro Ala Ser Tyr Gly
                85                  90                  95

Ile Arg Arg Tyr Glu Phe Asp Ala Trp Leu Leu Glu Arg Ala Ile Asn
            100                 105                 110

Asp Gly Val Arg Thr Ala Gln Gly Gln Pro Leu Lys Glu Leu Arg Arg
        115                 120                 125

Glu Asp Gly Glu Trp Val Leu Asn Asp His Leu Arg Thr Pro Leu Leu
130                 135                 140

Ile Gly Ala Gly Gly His Phe Cys Pro Val Ala Arg His Leu Gly Ala
145                 150                 155                 160

Ala Lys Pro Gly Ser Ser Glu Thr Ala Val His Ala Gln Glu Ile Glu
                165                 170                 175

Phe Glu Met Thr Pro Glu Gln Ala Ala Ala Cys Pro Val Glu Ala Asp
            180                 185                 190

Val Pro Glu Leu Tyr Phe Leu Arg Asp Leu Ser Gly Tyr Gly Trp Ile
        195                 200                 205

Val Arg Lys Gly Asp Trp Leu Asn Ile Gly Leu Gly Arg Glu Gly Gly
    210                 215                 220

Gln Lys Leu Gly Glu Gln Val Ser Ala Phe Ala Glu Glu Leu Lys Ala
225                 230                 235                 240

Met Gly Arg Leu His Ile Asp Pro Pro Ser Lys Phe Lys Gly His Ala
                245                 250                 255

Tyr Leu Leu His Gly His Ser Pro Arg Pro Val His Asp Gly Ala
            260                 265                 270

Leu Leu Ile Gly Asp Ala Ala Gly Leu Ala Tyr Pro Gln Ser Gly Glu
        275                 280                 285

Gly Ile Arg Pro Ala Val Glu Ser Ala Leu Met Ala Ala Glu Val Ile
    290                 295                 300

Gly Ala Ala Gly Gly Asp Tyr Ser Ala Asp Arg Leu Ala Ala Phe Gly
305                 310                 315                 320

Asp Arg Leu Gln Arg Arg Phe Gly Lys Gly Ser Ala Ala Gly Glu Pro
                325                 330                 335

Gly Pro Val Lys Gln Ala Leu Ala Arg Pro Leu Met Ala Ser Ser Trp
            340                 345                 350

Phe Ala Arg His Val Ile Leu Asp Arg Trp Phe Leu His Arg His Gln
        355                 360                 365

Ala Pro Leu Ala Pro Ala Ala
    370                 375
```

<210> SEQ ID NO 25
<211> LENGTH: 948
<212> TYPE: DNA

<213> ORGANISM: Desulfobacter curvatus

<400> SEQUENCE: 25

```
atgattgaaa aggagatcat tatcgtcgga ggcggtcctg ccggtgccgc ctgtgcctgg      60
aaattgaagc aaaggggcat tacgcccctg gtgctggata atattctttt tccccgtccc     120
aaggtgtgtg cgggatgggt gacccctgcc gtattcaggc tccttgaatt ccagggtgat     180
gattatcctt acaccttcag tcaatttgac cgaattcatt ttcatatgtt tggtataaaa     240
attcctgtac ccacccgtca atatgctgtc agaagatatg aatttgatgc ctggatgatc     300
tcccgcgccc atgttccggt taagacccat tgtgtaaaaa atattatccg gaagaacggt     360
ttttatatca ttgatgacca gtatcgatgc aggtatctca tcggtgccgg cggtacccat     420
tgcccggttt acaagacttt tttcactcaa aagcgttccc gtccttccaa gtccctcatt     480
gttgccgttg aaaaggaata tccatatgat attgttcata agcaatgcca tctatggttt     540
tttgatcatg gactgcctgg gtatgcctgg tatcttccca aggggaataa ctggttaaac     600
atcggcattg gcggaaaatt ccataggttg aagcagcggg gacagaacat tatggaccaa     660
tggcgtcatt ttacaatgga tcttcaaaaa aagggggttca tcggggaaaa tccatctagt     720
cccaaagggc acaattacta ttttcagcat ggtccgaaaa ataccaaca ggacaatgcc      780
ttcatcatcg gagatgcggc aggactctct accctggata tgggagaggg tatccatggc     840
gctgttttaa gcggtatccg tgcggcagat gccatcgtag aaaacaaacc gtttactttg     900
ccacacctgg caaggtttag cctgccgaaa atactgttgc ctgactga                  948
```

<210> SEQ ID NO 26
<211> LENGTH: 315
<212> TYPE: PRT
<213> ORGANISM: Desulfobacter curvatus

<400> SEQUENCE: 26

```
Met Ile Glu Lys Glu Ile Ile Val Gly Gly Gly Pro Gly Ala Gly
1               5                   10                  15

Ala Cys Ala Trp Lys Leu Lys Gln Arg Gly Ile Thr Pro Leu Val Leu
                20                  25                  30

Asp Lys Tyr Ser Phe Pro Arg Pro Lys Val Cys Ala Gly Trp Val Thr
            35                  40                  45

Pro Ala Val Phe Arg Leu Leu Glu Phe Gln Gly Asp Asp Tyr Pro Tyr
        50                  55                  60

Thr Phe Ser Gln Phe Asp Arg Ile His Phe His Met Phe Gly Ile Lys
65                  70                  75                  80

Ile Pro Val Pro Thr Arg Gln Tyr Ala Val Arg Arg Tyr Glu Phe Asp
                85                  90                  95

Ala Trp Met Ile Ser Arg Ala His Val Pro Val Lys Thr His Cys Val
            100                 105                 110

Lys Asn Ile Ile Arg Lys Asn Gly Phe Tyr Ile Ile Asp Asp Gln Tyr
        115                 120                 125

Arg Cys Arg Tyr Leu Ile Gly Ala Gly Gly Thr His Cys Pro Val Tyr
    130                 135                 140

Lys Thr Phe Phe Thr Gln Lys Arg Ser Arg Pro Ser Lys Ser Leu Ile
145                 150                 155                 160

Val Ala Val Glu Lys Glu Tyr Pro Tyr Asp Ile Val His Lys Gln Cys
                165                 170                 175

His Leu Trp Phe Phe Asp His Gly Leu Pro Gly Tyr Ala Trp Tyr Leu
            180                 185                 190
```

Pro Lys Gly Asn Asn Trp Leu Asn Ile Gly Ile Gly Gly Lys Phe His
        195                 200                 205

Arg Leu Lys Gln Arg Gly Gln Asn Ile Met Asp Gln Trp Arg His Phe
    210                 215                 220

Thr Met Asp Leu Gln Lys Lys Gly Phe Ile Gly Glu Asn Pro Ser Ser
225                 230                 235                 240

Pro Lys Gly His Asn Tyr Tyr Phe Gln His Gly Pro Lys Lys Tyr Gln
            245                 250                 255

Gln Asp Asn Ala Phe Ile Ile Gly Asp Ala Ala Gly Leu Ser Thr Leu
            260                 265                 270

Asp Met Gly Glu Gly Ile His Gly Ala Val Leu Ser Gly Ile Arg Ala
        275                 280                 285

Ala Asp Ala Ile Val Glu Asn Lys Pro Phe Thr Leu Pro His Leu Ala
        290                 295                 300

Arg Phe Ser Leu Pro Lys Ile Leu Leu Pro Asp
305                 310                 315

<210> SEQ ID NO 27
<211> LENGTH: 972
<212> TYPE: DNA
<213> ORGANISM: Unknown
<220> FEATURE:
<223> OTHER INFORMATION: Desulfobacter phenolica

<400> SEQUENCE: 27

```
atgatagatt ctaaaataat tattgtcggc ggaggccctg caggttctgc atgtgcatgg      60
aaactcaagc aggcagaaga acaaatcctt atcctggacc ggaagccttt tccgcgttcc     120
aaattgtgcg ccggatggat aaacccaaag gcattgaatg ccattgattt taaaaaacag     180
gaatatcctt ttttgcttca tccggttgac aggattcatt tttacctgtt cggggttcat     240
attccggttc aaacacgtca gtatgccata cgcagagttg aatttgatga ctggatggtg     300
aagcgggcca atgttcctgt gcatacgcat acagttaaaa aaatcattaa aaagaacggt     360
ttttatatta ttgataacca atacaggtgc caatatcttg ttggggccgg aggcacccat     420
tgtccagtgt tcagagtttt tttcagcaaa gatgaaaaaa gacccatgaa gtctatgatt     480
gcagcagttg aacaagagta tgtttgcgat taccaggaca gccgatgcca catttggttt     540
tttgacaaaa aacttccggg atattcctgg tatcttccca agggcaatgg ttggttaaat     600
atcggtatcg gcggaaaatt tttgaaaatg aaaaaacagg gcacaaccat tatggaccat     660
tggcgatatt ttacccaaaa acttttaagg ctctcattga tcaacaaaat tccggaaacg     720
cccaaaggtc atacctacta tctgcgccac cgtatgaacc aatgtcaaaa ggacaatgtg     780
tttgtgatcg gggatgcagc cggtttgtcc acacttgata tgggagaggg tatccatgcg     840
gcaattgccg gtggaattct ggctgcaaaa gccattgtcg agaaaaaaga gttccgggtt     900
gaatctttgg gaaaattcag tctgcctggt atgattttc aaaacaagag gtctctcaac     960
gattttttt ga                                                         972
```

<210> SEQ ID NO 28
<211> LENGTH: 323
<212> TYPE: PRT
<213> ORGANISM: Unknown
<220> FEATURE:
<223> OTHER INFORMATION: Desulfobacter phenolica

<400> SEQUENCE: 28

```
Met Ile Asp Ser Lys Ile Ile Ile Val Gly Gly Pro Ala Gly Ser
1               5                   10                  15

Ala Cys Ala Trp Lys Leu Lys Gln Ala Glu Glu Gln Ile Leu Ile Leu
            20                  25                  30

Asp Arg Lys Pro Phe Pro Arg Ser Lys Leu Cys Ala Gly Trp Ile Asn
            35                  40                  45

Pro Lys Ala Leu Asn Ala Ile Asp Phe Lys Lys Gln Glu Tyr Pro Phe
50                      55                  60

Leu Leu His Pro Val Asp Arg Ile His Phe Tyr Leu Phe Gly Val His
65                  70                  75                  80

Ile Pro Val Gln Thr Arg Gln Tyr Ala Ile Arg Arg Val Glu Phe Asp
                85                  90                  95

Asp Trp Met Val Lys Arg Ala Asn Val Pro Val His Thr His Thr Val
                100                 105                 110

Lys Lys Ile Ile Lys Lys Asn Gly Phe Tyr Ile Ile Asp Asn Gln Tyr
            115                 120                 125

Arg Cys Gln Tyr Leu Val Gly Ala Gly Gly Thr His Cys Pro Val Phe
130                 135                 140

Arg Val Phe Phe Ser Lys Asp Glu Lys Arg Pro Met Lys Ser Met Ile
145                 150                 155                 160

Ala Ala Val Glu Gln Glu Tyr Val Cys Asp Tyr Gln Asp Ser Arg Cys
                165                 170                 175

His Ile Trp Phe Phe Asp Lys Lys Leu Pro Gly Tyr Ser Trp Tyr Leu
            180                 185                 190

Pro Lys Gly Asn Gly Trp Leu Asn Ile Gly Ile Gly Gly Lys Phe Leu
        195                 200                 205

Lys Met Lys Lys Gln Gly Thr Thr Ile Met Asp His Trp Arg Tyr Phe
210                 215                 220

Thr Gln Lys Leu Leu Arg Leu Ser Leu Ile Asn Lys Ile Pro Glu Thr
225                 230                 235                 240

Pro Lys Gly His Thr Tyr Tyr Leu Arg His Arg Met Asn Gln Cys Gln
                245                 250                 255

Lys Asp Asn Val Phe Val Ile Gly Asp Ala Ala Gly Leu Ser Thr Leu
            260                 265                 270

Asp Met Gly Glu Gly Ile His Ala Ala Ile Ala Gly Gly Ile Leu Ala
        275                 280                 285

Ala Lys Ala Ile Val Glu Lys Lys Glu Phe Arg Val Glu Ser Leu Gly
290                 295                 300

Lys Phe Ser Leu Pro Gly Met Ile Phe Gln Asn Lys Arg Ser Leu Asn
305                 310                 315                 320

Asp Phe Phe
```

<210> SEQ ID NO 29
<211> LENGTH: 972
<212> TYPE: DNA
<213> ORGANISM: Desulfobacula toluolica

<400> SEQUENCE: 29

```
atgatagatt ctaaaataat tattgtcggc ggaggccctg cgggttctgc atgtgcatgg      60
aaactaaagc aggcagaaga acaaatcctt atcctggacc gaaagccttt tccgcgttcc     120
aaattgtgcg ccggatggat aaacccaaag gcattgaatg ccattgattt taaaaaacag     180
```

```
gaatatcctt ttttgcttca tccggttgac aggattcatt tttacctgtt cggggttcat      240
attccggttc aaacacgtca gtatgccata cgcagagttg aatttgatga ctggatggtg      300
aagcgggcca atgttcctgt gcatacgcat acagttaaaa aaatcattaa aaagaacggt      360
ttttatatta ttgataacca atacaggtgc caatatcttg ttggggccgg aggcacccat      420
tgtccagtgt tcagagtttt tttcagcaaa gatgaaaaaa gacccatgaa gtctatgatt      480
gcagcagttg aacaagagta tgtttgcgat taccaggaca gccgatgcca catttggttt      540
tttgacaaaa aacttcctgg atattcctgg tatcttccca agggcaatgg ttggttaaat      600
atcgggatcg gcggaaaatt tttgaaaatg aaaaaacagg gcacaaccat tatagatcat      660
tggagatatt ttacccaaaa acttttaagg ctctcattga tcaacaaaat tccggaaatg      720
cccaaaggtc atacctacta tctgcgccac cgtatgaacc aatgtcaaaa ggacaatgtg      780
tttgtgatcg gggatgcagc cggtttgtcc acacttgata tgggagaggg tatccatgcg      840
gcaattgccg gtggaattct ggctgcaaaa gccattgtcg agaaaaaga gttccgggtt      900 gaatctttgg gaaaattcag tctgcctggt atgattttc aaaacaagag gtctcacaaa      960 gaatttttt aa                                                          972
```

```
<210> SEQ ID NO 30
<211> LENGTH: 323
<212> TYPE: PRT
<213> ORGANISM: Desulfobacula toluolica

<400> SEQUENCE: 30

Met Ile Asp Ser Lys Ile Ile Ile Val Gly Gly Pro Ala Gly Ser
1               5                   10                  15

Ala Cys Ala Trp Lys Leu Lys Gln Ala Glu Glu Gln Ile Leu Ile Leu
            20                  25                  30

Asp Arg Lys Pro Phe Pro Arg Ser Lys Leu Cys Ala Gly Trp Ile Asn
        35                  40                  45

Pro Lys Ala Leu Asn Ala Ile Asp Phe Lys Lys Gln Glu Tyr Pro Phe
    50                  55                  60

Leu Leu His Pro Val Asp Arg Ile His Phe Tyr Leu Phe Gly Val His
65                  70                  75                  80

Ile Pro Val Gln Thr Arg Gln Tyr Ala Ile Arg Arg Val Glu Phe Asp
                85                  90                  95

Asp Trp Met Val Lys Arg Ala Asn Val Pro Val His Thr His Thr Val
            100                 105                 110

Lys Lys Ile Ile Lys Lys Asn Gly Phe Tyr Ile Ile Asp Asn Gln Tyr
        115                 120                 125

Arg Cys Gln Tyr Leu Val Gly Ala Gly Gly Thr His Cys Pro Val Phe
    130                 135                 140

Arg Val Phe Phe Ser Lys Asp Glu Lys Arg Pro Met Lys Ser Met Ile
145                 150                 155                 160

Ala Ala Val Glu Gln Glu Tyr Val Cys Asp Tyr Gln Asp Ser Arg Cys
                165                 170                 175

His Ile Trp Phe Phe Asp Lys Lys Leu Pro Gly Tyr Ser Trp Tyr Leu
            180                 185                 190

Pro Lys Gly Asn Gly Trp Leu Asn Ile Gly Ile Gly Gly Lys Phe Leu
        195                 200                 205

Lys Met Lys Lys Gln Gly Thr Thr Ile Ile Asp His Trp Arg Tyr Phe
    210                 215                 220
```

Thr Gln Lys Leu Leu Arg Leu Ser Leu Ile Asn Lys Ile Pro Glu Met
225                 230                 235                 240

Pro Lys Gly His Thr Tyr Tyr Leu Arg His Arg Met Asn Gln Cys Gln
            245                 250                 255

Lys Asp Asn Val Phe Val Ile Gly Asp Ala Ala Gly Leu Ser Thr Leu
        260                 265                 270

Asp Met Gly Glu Gly Ile His Ala Ala Ile Ala Gly Ile Leu Ala
    275                 280                 285

Ala Lys Ala Ile Val Glu Lys Glu Phe Arg Val Glu Ser Leu Gly
290                 295                 300

Lys Phe Ser Leu Pro Gly Met Ile Phe Gln Asn Lys Arg Ser His Lys
305                 310                 315                 320

Glu Phe Phe

<210> SEQ ID NO 31
<211> LENGTH: 948
<212> TYPE: DNA
<213> ORGANISM: Desulfobacter postgatei

<400> SEQUENCE: 31
atgattaaca aggagatcat tatcgtcgga ggcggtcctg ccggtgccgc ctgcgcctgg      60
acgctcaagc aaaaggggat cacgcccctg gtgctggata atattctttt tccccggccc     120
aaggtttgtg cgggatggat taccccctgcc gtatttaagc ttcttgaact ccgaggagat     180
gattatcctt acaccgtaag tcaatttgat agaattaatt ttcatctgtt tggtctaaaa     240
attcctgtac ccactcgtca atatgctgtc agacgtatg aatttgatgc ctggttgatc      300
tgccgcgccg gtgtcccggt taacacctat tgcgtaagaa atatcatccg gaagaacggt     360
ttttatatca ttgacgacca gtatcaatgc aagtacctca ttggtgccgg cggtaccccat    420 tgcccggttt acaagacgtt tttcactcaa acgcgtcccc gtcctcccaa atccctcatt     480
gttgccgttg agaaggaata cccatatgat atttcgcatc atcaatgcca tttgtggttt     540
tttgatcatg gtctgcctgg gtatgcctgg tatcttccca agggaaataa ctggttaaac     600
atcggcattg gcgcaaaatt ccatacgttg aaacagcggg gacagaacat tatggatcag     660
tggcgtcatt ttacaatgga tcttcaaaaa aagggggttta tcagggaaaa tccacctatt     720
cccaaaggtc acaattacta ttttcagcat ggtccggaaa ataccgaca ggacaatgcc     780 ttcatcatcg gagatgcggc agggctctct actctggata tgggagaggg tatccatggc     840
gctgttttaa gcggtatccg tgtggcagat gccatcgtag acaacaaacc gtttgtttg     900 cctcacccgc caaggttcag cctgccgaaa atactcttgc ctcattaa                  948

<210> SEQ ID NO 32
<211> LENGTH: 315
<212> TYPE: PRT
<213> ORGANISM: Desulfobacter postgatei

<400> SEQUENCE: 32

Met Ile Asn Lys Glu Ile Ile Val Gly Gly Gly Pro Ala Gly Ala
1               5                   10                  15

Ala Cys Ala Trp Thr Leu Lys Gln Lys Gly Ile Thr Pro Leu Val Leu
            20                  25                  30

Asp Lys Tyr Ser Phe Pro Arg Pro Lys Val Cys Ala Gly Trp Ile Thr
        35                  40                  45

Pro Ala Val Phe Lys Leu Leu Glu Leu Arg Gly Asp Asp Tyr Pro Tyr
              50                  55                  60

Thr Val Ser Gln Phe Asp Arg Ile Asn Phe His Leu Phe Gly Leu Lys
 65                  70                  75                  80

Ile Pro Val Pro Thr Arg Gln Tyr Ala Val Arg Arg Tyr Glu Phe Asp
                     85                  90                  95

Ala Trp Leu Ile Cys Arg Ala Gly Val Pro Val Asn Thr Tyr Cys Val
                100                 105                 110

Arg Asn Ile Ile Arg Lys Asn Gly Phe Tyr Ile Ile Asp Asp Gln Tyr
            115                 120                 125

Gln Cys Lys Tyr Leu Ile Gly Ala Gly Gly Thr His Cys Pro Val Tyr
        130                 135                 140

Lys Thr Phe Phe Thr Gln Thr Arg Pro Arg Pro Lys Ser Leu Ile
145                 150                 155                 160

Val Ala Val Glu Lys Glu Tyr Pro Tyr Asp Ile Ser His His Gln Cys
                165                 170                 175

His Leu Trp Phe Phe Asp His Gly Leu Pro Gly Tyr Ala Trp Tyr Leu
            180                 185                 190

Pro Lys Gly Asn Asn Trp Leu Asn Ile Gly Ile Gly Ala Lys Phe His
        195                 200                 205

Thr Leu Lys Gln Arg Gly Gln Asn Ile Met Asp Gln Trp Arg His Phe
    210                 215                 220

Thr Met Asp Leu Gln Lys Lys Gly Phe Ile Arg Glu Asn Pro Pro Ile
225                 230                 235                 240

Pro Lys Gly His Asn Tyr Tyr Phe Gln His Gly Pro Glu Lys Tyr Arg
                245                 250                 255

Gln Asp Asn Ala Phe Ile Ile Gly Asp Ala Ala Gly Leu Ser Thr Leu
            260                 265                 270

Asp Met Gly Glu Gly Ile His Gly Ala Val Leu Ser Gly Ile Arg Val
        275                 280                 285

Ala Asp Ala Ile Val Asp Asn Lys Pro Phe Val Leu Pro His Pro Pro
    290                 295                 300

Arg Phe Ser Leu Pro Lys Ile Leu Leu Pro His
305                 310                 315

<210> SEQ ID NO 33
<211> LENGTH: 1134
<212> TYPE: DNA
<213> ORGANISM: Unknown
<220> FEATURE:
<223> OTHER INFORMATION: Halofilum ochraceum

<400> SEQUENCE: 33
atgagccgga cccacgacgt catcatcgtt ggcggcggac cgtccgggtc gacactggcc      60
tgggcgctgg agcgccgggg gcttcggccg ctggtgatgg acaaggccga gttccccgc     120 gacaagacct gcgccggctg ggtgacgccg gcggtcatgt ccgaactcga ggtggatctc     180
gaggatttcg cgaagcactg cgtactccag ccgatccaca acttccgcat gggatgatg     240 gggcagcgcg cggtccacaa tcatcacggc gacagccccg tcagttacgg catcctccgc     300
cgacagttcg acaactacct gctgcagcgc acgggcgcgg acaaggcgct gggcgtgaag     360
ttcgagtctc tggagcgtga tgcggacggc ctgtggtgcg tcaacggcga atatcgcgcg     420
ccgctggtcg tcggcgccgg cgggcacttc tgcccgatcg ccgcacgcct gggtgagggc     480
cccggcaaga cgagacggc gatcaccgcc aaggaagtcg agttcgagat gaacgccgag     540

```
caggcggcgc actgcaaggt gcgggaagat accccggagc tgtggttctg ccgcgacctc    600
aagggctacg cctgggtctt ccgcaagggc gactatctca atatcggcct cggccgcgaa    660
ggtaatcatc gcctgaaaga gcatctgcag gcattcgttg acgagatgca ggccgagggc    720
cgcctgccgt cggatatgcc cggccgcttc aagggccacg cctatcttct ctacggtcgg    780
gccgagcgcc cgttgatcga cgatgggctg atgctgatcg gcgatgcggc cggtctggca    840
tatgaccaga gcgcgaagg catccggccc ggggtcgaat cggcgctgat cgcggccgag    900
gtcatcgccg atgtcgcgga ttacgggaaa gacgatctca gcccgtacgt gcagcggatc    960
aatgaacgct tggtgtgcg ggcgtccgag gcgaaggact cgggtatcgt cctgcccgac   1020
tgggccaaac tcaaggcggc tccacccctg atgcgctcgc actggttcac ccgtcgggtc   1080
gtcaccgaac gctggttcct gcaccagcag gtgccgccgc tgcgcgcgag ctga         1134
```

<210> SEQ ID NO 34
<211> LENGTH: 377
<212> TYPE: PRT
<213> ORGANISM: Unknown
<220> FEATURE:
<223> OTHER INFORMATION: Halofilum ochraceum

<400> SEQUENCE: 34

```
Met Ser Arg Thr His Asp Val Ile Ile Val Gly Gly Pro Ser Gly
1               5                   10                  15

Ser Thr Leu Ala Trp Ala Leu Glu Arg Arg Gly Leu Arg Pro Leu Val
            20                  25                  30

Met Asp Lys Ala Glu Phe Pro Arg Asp Lys Thr Cys Ala Gly Trp Val
        35                  40                  45

Thr Pro Ala Val Met Ser Glu Leu Glu Val Asp Leu Glu Asp Phe Ala
    50                  55                  60

Lys His Cys Val Leu Gln Pro Ile His Asn Phe Arg Ile Gly Met Met
65                  70                  75                  80

Gly Gln Arg Ala Val His Asn His His Gly Asp Ser Pro Val Ser Tyr
                85                  90                  95

Gly Ile Leu Arg Arg Gln Phe Asp Asn Tyr Leu Leu Gln Arg Thr Gly
            100                 105                 110

Ala Asp Lys Ala Leu Gly Val Lys Phe Glu Ser Leu Glu Arg Asp Ala
        115                 120                 125

Asp Gly Leu Trp Cys Val Asn Gly Glu Tyr Arg Ala Pro Leu Val Val
    130                 135                 140

Gly Ala Gly Gly His Phe Cys Pro Ile Ala Ala Arg Leu Gly Glu Gly
145                 150                 155                 160

Pro Gly Lys Asn Glu Thr Ala Ile Thr Ala Lys Glu Val Glu Phe Glu
                165                 170                 175

Met Asn Ala Glu Gln Ala Ala His Cys Lys Val Arg Glu Asp Thr Pro
            180                 185                 190

Glu Leu Trp Phe Cys Arg Asp Leu Lys Gly Tyr Ala Trp Val Phe Arg
        195                 200                 205

Lys Gly Asp Tyr Leu Asn Ile Gly Leu Gly Arg Glu Gly Asn His Arg
    210                 215                 220

Leu Lys Glu His Leu Gln Ala Phe Val Asp Glu Met Gln Ala Glu Gly
225                 230                 235                 240

Arg Leu Pro Ser Asp Met Pro Gly Arg Phe Lys Gly His Ala Tyr Leu
                245                 250                 255
```

```
Leu Tyr Gly Arg Ala Glu Arg Pro Leu Ile Asp Asp Gly Leu Met Leu
            260                 265                 270

Ile Gly Asp Ala Ala Gly Leu Ala Tyr Asp Gln Ser Gly Glu Gly Ile
        275                 280                 285

Arg Pro Gly Val Glu Ser Ala Leu Ile Ala Ala Glu Val Ile Ala Asp
    290                 295                 300

Val Ala Asp Tyr Gly Lys Asp Asp Leu Ser Pro Tyr Val Gln Arg Ile
305                 310                 315                 320

Asn Glu Arg Phe Gly Val Arg Ala Ser Glu Ala Lys Asp Ser Gly Ile
                325                 330                 335

Val Leu Pro Asp Trp Ala Lys Leu Lys Ala Ala Pro Pro Leu Met Arg
            340                 345                 350

Ser His Trp Phe Thr Arg Arg Val Val Thr Glu Arg Trp Phe Leu His
        355                 360                 365

Gln Gln Val Pro Pro Leu Arg Ala Ser
    370                 375

<210> SEQ ID NO 35
<211> LENGTH: 1125
<212> TYPE: DNA
<213> ORGANISM: Unknown
<220> FEATURE:
<223> OTHER INFORMATION: Marinobacter aquaeolei

<400> SEQUENCE: 35
atggaatact acgacatcat tatcgtgggg gccggccctg ccggctcaac cctggcccgg      60
gctctggagg actccggcaa acgggtactg atcatcgaca agcaagcctt cccccgggac     120
aagacctgcg ccggctgggt tacgccggca gtgatggcca gcctggacat tgatccgggg     180
aagtattccg tcggccggac actgcaaccc attcgccggt tccggatcgg catgatgggg     240
caaagtgcgg tggagaacga ccacggggat attgtcagct acggtattcg tcgctgcgaa     300
ttcgacgact acctgctgga ccgtgccgag tgtgaaaagc aactggcaac cgcggtaaag     360
tccatcaacc ggaacaacgg caactgggtg atcaacgatc aatggcaggc cgcgctgctg     420
gtgggtgccg ggggccattt ctgcccggtg gcacggctgt gggcgacgg ccgcgggcaag     480 catgaaaccg tggtggccgc caaggaagtt gagttcgaga tgacgccaga gcaggcccgc     540
gcctgcgaag cccgcggcga cacgccagag ctctggttct gccgggatct caagggctac     600
gcctgggttt ccggaaaagg cagctatctg aacatcggcc tgggccgtga ggacaaccac     660
cggttatctg atcatctgga gcttttgtc gaggaaatga acagtcggg ccgcattcct     720 tcagacctgc caggccgctt caaaggtcac gcctatctgc tgtacgccca tgccaaccga     780
ccactggtgg atgacggcgt gttgctgatt ggcgatgcgg ccgtctggc ctataccag     840 agtggcgagg gcattcggcc cgccatagaa tcggcactga tggcggccaa tgtgatcaag     900
gccgccccgg attattccgc actgtcgctg caaagctatg gtgaacgcat gccgaacgc      960 ttcggaaccc gggccacaga ccagcaaccc ggatttgaag tgccggagtg gctgaaacag    1020
cccatcgcca gcaccctgat gcgctcgcac tggtttaccc gcaaggtggt gacggagaag    1080
tggttcctgc atcaggaggt gccgccgctg gaggtggcgg tgtga                    1125

<210> SEQ ID NO 36
<211> LENGTH: 374
<212> TYPE: PRT
<213> ORGANISM: Unknown
<220> FEATURE:
<223> OTHER INFORMATION: Marinobacter aquaeolei
```

<400> SEQUENCE: 36

```
Met Glu Tyr Tyr Asp Ile Ile Val Gly Ala Gly Pro Ala Gly Ser
1               5                   10                  15

Thr Leu Ala Arg Ala Leu Glu Asp Ser Gly Lys Arg Val Leu Ile Ile
            20                  25                  30

Asp Lys Gln Ala Phe Pro Arg Asp Lys Thr Cys Ala Gly Trp Val Thr
        35                  40                  45

Pro Ala Val Met Ala Ser Leu Asp Ile Asp Pro Gly Lys Tyr Ser Val
    50                  55                  60

Gly Arg Thr Leu Gln Pro Ile Arg Arg Phe Arg Ile Gly Met Met Gly
65                  70                  75                  80

Gln Ser Ala Val Glu Asn Asp His Gly Asp Ile Val Ser Tyr Gly Ile
                85                  90                  95

Arg Arg Cys Glu Phe Asp Asp Tyr Leu Leu Asp Arg Ala Glu Cys Glu
            100                 105                 110

Lys Gln Leu Ala Thr Ala Val Lys Ser Ile Asn Arg Asn Asn Gly Asn
        115                 120                 125

Trp Val Ile Asn Asp Gln Trp Gln Ala Pro Leu Leu Val Gly Ala Gly
    130                 135                 140

Gly His Phe Cys Pro Val Ala Arg Leu Leu Gly Asp Gly Pro Gly Lys
145                 150                 155                 160

His Glu Thr Val Val Ala Ala Lys Glu Val Glu Phe Glu Met Thr Pro
                165                 170                 175

Glu Gln Ala Arg Ala Cys Glu Ala Arg Gly Asp Thr Pro Glu Leu Trp
            180                 185                 190

Phe Cys Arg Asp Leu Lys Gly Tyr Ala Trp Val Phe Arg Lys Gly Ser
        195                 200                 205

Tyr Leu Asn Ile Gly Leu Gly Arg Glu Asp Asn His Arg Leu Ser Asp
    210                 215                 220

His Leu Glu Ala Phe Val Glu Glu Met Lys Gln Ser Gly Arg Ile Pro
225                 230                 235                 240

Ser Asp Leu Pro Gly Arg Phe Lys Gly His Ala Tyr Leu Leu Tyr Ala
                245                 250                 255

His Ala Asn Arg Pro Leu Val Asp Asp Gly Val Leu Leu Ile Gly Asp
            260                 265                 270

Ala Ala Gly Leu Ala Tyr Thr Gln Ser Gly Glu Gly Ile Arg Pro Ala
        275                 280                 285

Ile Glu Ser Ala Leu Met Ala Ala Asn Val Ile Lys Ala Ala Pro Asp
    290                 295                 300

Tyr Ser Ala Leu Ser Leu Gln Ser Tyr Gly Glu Arg Ile Ala Glu Arg
305                 310                 315                 320

Phe Gly Thr Arg Ala Thr Asp Gln Gln Pro Gly Phe Glu Val Pro Glu
                325                 330                 335

Trp Leu Lys Gln Pro Ile Ala Ser Thr Leu Met Arg Ser His Trp Phe
            340                 345                 350

Thr Arg Lys Val Val Thr Glu Lys Trp Phe Leu His Gln Glu Val Pro
        355                 360                 365

Pro Leu Glu Val Ala Val
    370
```

<210> SEQ ID NO 37
<211> LENGTH: 1263
<212> TYPE: DNA

<213> ORGANISM: Thermomonospora curvata

<400> SEQUENCE: 37

```
atgacgctgg ccaaggtctt cgaggagctg gtcggggcgg acgcccctgt ggagctcacc      60
gcctacgacg gatcgagagc cggacgcctg ggcagtgatc tgcgggtcca cgtgaagtcg     120
ccgtacgcgg tgtcctacct ggtgcactcg ccgagcgcgc tcgggctggc ccgcgcgtac     180
gtggccgggc acctggacgc ctacggcgac atgtacacgc tgctgcggga gatgacgcag     240
ctgaccgagg cgctgacgcc caaggcccgg ctgcggctgc tggccggtgt cctgcaggat     300
ccgctgctgc gcgcggcggc cagccgccgt ctgccgcccc cgccgcagga ggtgcggacc     360
ggccgcacct cctggttccg gcacaccaag cggcgggacg ccaaggccat ctcccaccac     420
tacgacgtgt ccaacacctt ctatgagtgg gtgctgggcc cgtcgatgac ctacacctgc     480
gcctgtttcc ccaccgagga cgccaccttg gaggaggcgc agttccacaa gcacgacctg     540
gtcgccaaga gctcgggct gcggccgggc atgcggctgc tggacgtggg ctgcggctgg     600
ggcggcatgg tgatgcacgc cgccaagcac tacggggtgc gggcgctggg cgtcacgctg     660
tccaagcagc aggccgagtg ggcgcagaag gccatcgccg aggcgggcct gagcgacctg     720
gccgaggtcc gccaccagga ctaccgggac gtcaccgagg gcgacttcga cgccatcagc     780
tcgatcggcc tcaccgagca catcggcaag gccaacctgc cgtcctactt cggcttcctg     840
tacggcaagc tcaagcccgg cgggcggctg ctcaaccact gcatcacccg gcccgacaac     900
acccagccgg ccatgaagaa ggacgggttc atcaaccggt acgtcttccc cgacggggag     960
ctggaggggc ccggctacct gcagacccag atgaacgacg ccggttttga gatccgccac    1020
caggagaacc tgcgcgagca ctacgcccgc accctggccg gatggtgccg caacctcgat    1080
gagcactggg acgaggcggt ggccgaggtc ggcgagggca ccgcgcgggt gtggcggctg    1140
tacatggccg gcagccggct cggtttcgag ctcaactgga tccagctgca ccagatcctg    1200
ggcgtcaagc tcggcgagcg cggcgagtcc cgcatgccgt gcggcccgga ctggggcgtg    1260
tga                                                                  1263
```

<210> SEQ ID NO 38
<211> LENGTH: 420
<212> TYPE: PRT
<213> ORGANISM: Thermomonospora curvata

<400> SEQUENCE: 38

```
Met Thr Leu Ala Lys Val Phe Glu Glu Leu Val Gly Ala Asp Ala Pro
1               5                   10                  15

Val Glu Leu Thr Ala Tyr Asp Gly Ser Arg Ala Gly Arg Leu Gly Ser
                20                  25                  30

Asp Leu Arg Val His Val Lys Ser Pro Tyr Ala Val Ser Tyr Leu Val
            35                  40                  45

His Ser Pro Ser Ala Leu Gly Leu Ala Arg Ala Tyr Val Ala Gly His
        50                  55                  60

Leu Asp Ala Tyr Gly Asp Met Tyr Thr Leu Leu Arg Glu Met Thr Gln
65                  70                  75                  80

Leu Thr Glu Ala Leu Thr Pro Lys Ala Arg Leu Arg Leu Leu Ala Gly
                85                  90                  95

Val Leu Gln Asp Pro Leu Leu Arg Ala Ala Ser Arg Arg Leu Pro
                100                 105                 110

Pro Pro Pro Gln Glu Val Arg Thr Gly Arg Thr Ser Trp Phe Arg His
            115                 120                 125
```

Thr Lys Arg Arg Asp Ala Lys Ala Ile Ser His His Tyr Asp Val Ser
        130                 135                 140

Asn Thr Phe Tyr Glu Trp Val Leu Gly Pro Ser Met Thr Tyr Thr Cys
145                 150                 155                 160

Ala Cys Phe Pro Thr Glu Asp Ala Thr Leu Glu Glu Ala Gln Phe His
                165                 170                 175

Lys His Asp Leu Val Ala Lys Lys Leu Gly Leu Arg Pro Gly Met Arg
            180                 185                 190

Leu Leu Asp Val Gly Cys Gly Trp Gly Met Val Met His Ala Ala
        195                 200                 205

Lys His Tyr Gly Val Arg Ala Leu Gly Val Thr Leu Ser Lys Gln Gln
        210                 215                 220

Ala Glu Trp Ala Gln Lys Ala Ile Ala Glu Ala Gly Leu Ser Asp Leu
225                 230                 235                 240

Ala Glu Val Arg His Gln Asp Tyr Arg Asp Val Thr Glu Gly Asp Phe
                245                 250                 255

Asp Ala Ile Ser Ser Ile Gly Leu Thr Glu His Ile Gly Lys Ala Asn
            260                 265                 270

Leu Pro Ser Tyr Phe Gly Phe Leu Tyr Gly Lys Leu Lys Pro Gly Gly
        275                 280                 285

Arg Leu Leu Asn His Cys Ile Thr Arg Pro Asp Asn Thr Gln Pro Ala
        290                 295                 300

Met Lys Lys Asp Gly Phe Ile Asn Arg Tyr Val Phe Pro Asp Gly Glu
305                 310                 315                 320

Leu Glu Gly Pro Gly Tyr Leu Gln Thr Gln Met Asn Asp Ala Gly Phe
                325                 330                 335

Glu Ile Arg His Gln Glu Asn Leu Arg Glu His Tyr Ala Arg Thr Leu
            340                 345                 350

Ala Gly Trp Cys Arg Asn Leu Asp Glu His Trp Asp Glu Ala Val Ala
        355                 360                 365

Glu Val Gly Glu Gly Thr Ala Arg Val Trp Arg Leu Tyr Met Ala Gly
        370                 375                 380

Ser Arg Leu Gly Phe Glu Leu Asn Trp Ile Gln Leu His Gln Ile Leu
385                 390                 395                 400

Gly Val Lys Leu Gly Glu Arg Gly Glu Ser Arg Met Pro Leu Arg Pro
                405                 410                 415

Asp Trp Gly Val
            420

<210> SEQ ID NO 39
<211> LENGTH: 4582
<212> TYPE: DNA
<213> ORGANISM: Desulfobacter postgatei

<400> SEQUENCE: 39
ctaaattgta agcgttaata ttttgttaaa attcgcgtta aatttttgtt aaatcagctc      60 atttttaac caataggccg aaatcggcaa atcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa agggggatgt     240
gctgcaaggc gattaagttg ggtaacgcca gggttttccc agtcacgacg ttgtaaaacg     300
acggccagtg agcgcgacgt aatacgactc actataggc gaattggcgg aaggccgtca     360
aggcctaggc gcgccatgag ctcagctggt gacaattaat catcggctcg tataatgtgt     420

```
ggaattgaat cgatataagg aggttaatca tatgaaaaat caggatatca agaaatccat    480
acacaaatta ttgaattttg ccggcatcac cgttaacgga agcaatccct acgatattca    540
ggtgaaaaat gaccggtttt accaacgaat aatccatgaa cctgctctgg ggcttggtga    600
agcatatatg gataactggt gggagtgccg tgccctggat cagttcatcg caaaagtgtt    660
gtgcgcaaac cttggacaag tattaaaaaa ggagtggcgg atcacatgga acctgttaac    720
ggcaaagctt tttaatcaac agtcttccaa gcgtgccttt atggtgggcc aacgccacta    780
tgacatcggc aatgatcttt atcagggcat gctggacaaa caaatgcagt atacctgcgg    840
atactggaaa gatgccacca cccttgatca ggcccaggag gcgaaactgg cactggtctg    900
ccggaaatta aaactggaac ccggtatgaa agttcttgag ctgggatgcg ggtttggcgg    960
gtttgcccac tatgcggcaa caaggtacgg cgttgaagtg actggataca ccgtctccaa   1020
agagcaggtc aaatttgcag aaaaactatg caaagggctt cctgttgata tccggctggc   1080
agattacaga accgccaccg gagaaatatga ccgggtactc tccattggtt taatggagca   1140
tgtggggtat aaaaattatg gcacttacat gaaactgacc aatcggttgc taagggatga   1200
cggcattgct ttggttcata ccatcggtcg taatgatagt cgttgtgcct gcaactcatg   1260
gactgcaaaa tatattttcc ccaatggcat gcttccctcc attgcccagt gggaaaagc    1320 catgaaaaac caatttgtca tggaggactg cataactttt ggagaggact acgataaaac   1380
attaatggca tggtacgaaa atttcagaca ggtgtggccc aaacttaaag atagatacaa   1440
cgatcggttt tatcgcatgt gggagtatta tctgttaagc tgtgccggag gatttcggtc   1500
tcgatccatg cagttatggc agattgtgat gactaaacag ggaacttcag cgccctgttg   1560
tcgccttgtg taaggaaatc cattatgatt aacaaggaga tcattatcgt cggaggcgt    1620 cctgccggtg ccgcctgcgc ctggacgctc aagcaaaagg ggatcacgcc cctggtgctg   1680
gataaatatt cttttccccg gcccaaggtt tgtgcgggat ggattacccc tgccgtattt   1740
aagcttcttg aactccgagg agatgattat ccttacaccg taagtcaatt tgatagaatt   1800 aatttttcatc tgtttggtct aaaaattcct gtacccactc gtcaatatgc tgtcagacga   1860
tatgaatttg atgcctggtt gatctgccgc gccggtgtcc cggttaacac ctattgcgta   1920
agaaatatca tccggaagaa cggttttttat atcattgacg accagtatca atgcaagtac   1980
ctcattggtg ccggcggtac ccattgcccg gtttacaaga cgttttttcac tcaaacgcgt   2040 ccccgtcctc ccaaatccct cattgttgcc gttgagaagg aatacccata tgatatttcg   2100
catcatcaat gccatttgtg gttttttgat catggtctgc ctgggtatgc ctggtatctt   2160
cccaagggaa ataactggtt aaacatcggc attggcgcaa aattccatac gttgaaacag   2220
cggggacaga acattatgga tcagtggcgt cattttacaa tggatcttca aaaaaagggg   2280
tttatcaggg aaaatccacc tattcccaaa ggtcacaatt actattttca gcatggtccg   2340
gaaaaatacc gacaggacaa tgccttcatc atcggagatg cggcagggct ctctactctg   2400
gatatgggag agggtatcca tggcgctgtt ttaagcggta tccgtgtggc agatgccatc   2460
gtagacaaca aaccgtttgt tttgcctcac ccgccaaggt tcagcctgcc gaaaatactc   2520
ttgcctcatt aacctcaaaa tatattttcc ctctatcttc tcgttgcgct taatttgact   2580
aattctcatt agcgaggtac ctcttaatta actggcctca tgggccttcc gctcactgcc   2640
cgcttttcag tcgggaaacc tgtcgtgcca gctgcattaa catggtcata gctgtttcct   2700
tgcgtattgg gcgctctccg cttcctcgct cactgactcg ctgcgctcgg tcgttcgggt   2760
```

```
aaagcctggg gtgcctaatg agcaaaaggc cagcaaaagg ccaggaaccg taaaaaggcc    2820
gcgttgctgg cgttttttcca taggctccgc cccccctgacg agcatcacaa aaatcgacgc   2880
tcaagtcaga ggtggcgaaa cccgacagga ctataaagat accaggcgtt tccccctgga    2940
agctccctcg tgcgctctcc tgttccgacc ctgccgctta ccggatacct gtccgccttt    3000
ctcccttcgg gaagcgtggc gctttctcat agctcacgct gtaggtatct cagttcggtg    3060
taggtcgttc gctccaagct gggctgtgtg cacgaacccc ccgttcagcc cgaccgctgc    3120
gccttatccg gtaactatcg tcttgagtcc aacccggtaa gacacgactt atcgccactg    3180
gcagcagcca ctggtaacag gattagcaga gcgaggtatg taggcggtgc tacagagttc    3240
ttgaagtggt ggcctaacta cggctacact agaagaacag tatttggtat ctgcgctctg    3300
ctgaagccag ttaccttcgg aaaaagagtt ggtagctctt gatccggcaa acaaaccacc    3360
gctggtagcg gtggtttttt tgtttgcaag cagcagatta cgcgcagaaa aaaggatct    3420
caagaagatc ctttgatctt ttctacgggg tctgacgctc agtggaacga aaactcacgt    3480
taagggattt tggtcatgag attatcaaaa aggatcttca cctagatcct tttaaattaa    3540
aaatgaagtt ttaaatcaat ctaaagtata tatgagtaaa cttggtctga cagttaccaa    3600
tgcttaatca gtgaggcacc tatctcagcg atctgtctat ttcgttcatc catagttgcc    3660
tgactcccg tcgtgtagat aactacgata cgggagggct taccatctgg ccccagtgct    3720
gcaatgatac cgcgagaacc acgctcaccg gctccagatt tatcagcaat aaaccagcca    3780
gccggaaggg ccgagcgcag aagtggtcct gcaactttat ccgcctccat ccagtctatt    3840
aattgttgcc gggaagctag agtaagtagt tcgccagtta atagtttgcg caacgttgtt    3900
gccattgcta caggcatcgt ggtgtcacgc tcgtcgtttg gtatggcttc attcagctcc    3960
ggttcccaac gatcaaggcg agttacatga tcccccatgt tgtgcaaaaa agcggttagc    4020
tccttcggtc ctccgatcgt tgtcagaagt aagttggccg cagtgttatc actcatggtt    4080
atggcagcac tgcataattc tcttactgtc atgccatccg taagatgctt ttctgtgact    4140
ggtgagtact caaccaagtc attctgagaa tagtgtatgc ggcgaccgag ttgctcttgc    4200
ccggcgtcaa tacgggataa taccgcgcca catagcagaa ctttaaaagt gctcatcatt    4260
ggaaaacgtt cttcggggcg aaaactctca aggatcttac cgctgttgag atccagttcg    4320
atgtaaccca ctcgtgcacc caactgatct tcagcatctt ttactttcac cagcgtttct    4380
gggtgagcaa aaacaggaag gcaaaatgcc gcaaaaaagg gaataagggc gacacggaaa    4440
tgttgaatac tcatactctt ccttttcaa tattattgaa gcatttatca gggttattgt    4500
ctcatgagcg gatacatatt tgaatgtatt tagaaaaata aacaaatagg ggttccgcgc    4560
acatttcccc gaaaagtgcc ac                                             4582
```

```
<210> SEQ ID NO 40
<211> LENGTH: 4612
<212> TYPE: DNA
<213> ORGANISM: Unknown
<220> FEATURE:
<223> OTHER INFORMATION: Desulfobacula balticum

<400> SEQUENCE: 40
ctaaattgta agcgttaata ttttgttaaa attcgcgtta aattttttgtt aaatcagctc     60
atttttttaac caataggccg aaatcggcaa aatcccttat aaatcaaaag aatagaccga   120
gatagggttg agtggccgct acagggcgct cccattcgcc attcaggctg cgcaactgtt   180
gggaagggcg tttcggtgcg ggcctcttcg ctattacgcc agctggcgaa aggggggatgt   240
```

```
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgccatgag ctcagctggt gacaattaat catcggctcg tataatgtgt    420
ggaattgaat cgatataagg aggttaatca tatgaagttg gacaggcca gagaattatt    480 ttcagagatg atgaatcatg ccggcatccg agtgaatggg gaccggccgt ttgatatccg    540
gatcaaaaac gatcaatttt tccagcgggt gacgtcatcc ccggctttgg gtctgggtga    600
gtcttatatg gatggctggt gggattgtcc ggcaccggat cagttcattg aaaaagtgct    660
tcgggccaat cttctcaaac agatcaaaca ggaccggatc acggcctgga acgccctgat    720
ggcaaagatt ttcaatctcc agaccattaa acgggcattt accgtgggca acagcatta    780 tgatatcggc aatgatctgt atcaaatgat gctgggcaaa cggatgcagt atacctgcgg    840
gtactggaaa gacgcccgga acctggacga ggcccaggag gccaaactgg aaatgatctg    900
ccggaaactg gcactggcac cgggaatgaa tgttctggaa ctcgggtgcg ggttcggcgg    960
atttgcccgg tatgcggctg aaaaatatca ggtgtccgtg accgggttca ccgtgtcgaa   1020
aaaacaggcg gaattcggcc gggaatactg caaagacctg cccgtggata tccggctgga   1080
tgattaccgc aatgccagag gcacttatga ccgcatcctg tccatcggcc tgatggagca   1140
tgtgggattt aaaaactacc ggacctatat ggaactgacc cgcaacctgc ttaaaaaaga   1200
cggcatcgcg ttcgtgcata ccatcggcgg aaatatcacc cccggatct gcaatccctg   1260 gacggccaaa tacatttttc ccaattccgt gctgccgtcc atttccgaac tgggaagagc   1320
catgaagggg ctgtttgtcc tggaagactg ccacaatttc ggggaagatt atgacaaaac   1380
cctgatggcc tggtatgaca acttcaaggc ggcctggccc aagctcaaaa accggtatga   1440
cgaccggttt tttcggatgt gggaatatta cctgctcagt tccgccggcg ggttccgggc   1500
acggtccatg cagctgtggc agatggtgct gacccggccc ggccggccga accagactg    1560 ccggatctcg tgaggaaatc cattatgatt cagacggatg tgatcattgt gggcgggggc   1620
ccggccggat ccgcctgtgc ggcccgtctc aaaaaaaccg gaatgatgt caggatactg    1680 gacaaacaaa ggtttcccag gaaaaaactg tgtgccggat ggatctcacc cggggtgttt   1740
gatgacctgg gatacgaccc tgataccatat ccccacgcct tgacccggat ccacgggatt   1800
cactttcacc tgtttcaggt tcctttgccc gtgcgaacgc accagtatgc aatccggcgc   1860
atcgagttcg accactggct gctccagaag gccggggtgc ccgtgcacac ccatgccgta   1920
aaaaaaattc aaagaatccg gtccgggtat gtcatcgatg accagtttga atgccggtac   1980
ctggtcgggg ccggcggcac ccattgcccg gtgcggcgca cttttatgga acctgtgccg   2040
tcccgtccgg aaaccgcccg catcgccgcc gtggaaaaag agtttcaagg ctttcaacgg   2100
gtccggaagt gtcatatctg gtatctggaa aaaggcctgc ccggatatgc gtggtacctg   2160
cccaaaaaag gcgggtggat caacatcggc atcggcggca acagcacgg cctgaccgcc   2220 cggaaaacca ccatcatgga tcactggcgc acatttgtgg cccgcctgat ggataaaggc   2280
tttctggacc aatccccggg caatccctcc gggcatacct attatctgcg gcatacacct   2340
tatcaccggc aaactttgga aaacagcatg ccggacaatc tgtttgtcat cggcgatgct   2400
gccggcctgt ccaccctgga catggggaa ggcatccatg cggccgtcca gagcggcatt   2460
gccgcggctg acgccattat tgccggccgt cccatgcagg tgagccacat ctcccggttc   2520
agcctgccgg gcctggtgaa gtccggattc cgttccgctt aacctcaaaa tatattttcc   2580
```

```
ctctatcttc tcgttgcgct taatttgact aattctcatt agcgaggtac ctcttaatta    2640
actggcctca tgggccttcc gctcactgcc cgctttccag tcgggaaacc tgtcgtgcca    2700
gctgcattaa catggtcata gctgtttcct tgcgtattgg gcgctctccg cttcctcgct    2760
cactgactcg ctgcgctcgg tcgttcgggt aaagcctggg gtgcctaatg agcaaaaggc    2820
cagcaaaagg ccaggaaccg taaaaaggcc gcgttgctgg cgttttttcca taggctccgc    2880 cccctgacg agcatcacaa aaatcgacgc tcaagtcaga ggtggcgaaa cccgacagga    2940
ctataaagat accaggcgtt ccccctgga agctccctcg tgcgctctcc tgttccgacc    3000
ctgccgctta ccggatacct gtccgccttt ctcccttcgg gaagcgtggc gctttctcat    3060
agctcacgct gtaggtatct cagttcggtg taggtcgttc gctccaagct gggctgtgtg    3120
cacgaacccc ccgttcagcc cgaccgctgc gccttatccg gtaactatcg tcttgagtcc    3180
aacccggtaa gacacgactt atcgccactg gcagcagcca ctggtaacag gattagcaga    3240
gcgaggtatg taggcggtgc tacagagttc ttgaagtggt ggcctaacta cggctacact    3300
agaagaacag tatttggtat ctgcgctctg ctgaagccag ttaccttcgg aaaaagagtt    3360
ggtagctctt gatccggcaa acaaaccacc gctggtagcg gtggtttttt tgtttgcaag    3420
cagcagatta cgcgcagaaa aaaggatctc aagaagatc ctttgatctt ttctacgggg    3480
tctgacgctc agtggaacga aaactcacgt taagggattt tggtcatgag attatcaaaa    3540
aggatcttca cctagatcct tttaaattaa aaatgaagtt ttaaatcaat ctaaagtata    3600
tatgagtaaa cttggtctga cagttaccaa tgcttaatca gtgaggcacc tatctcagcg    3660
atctgtctat ttcgttcatc catagttgcc tgactccccg tcgtgtagat aactacgata    3720
cgggagggct taccatctgg ccccagtgct gcaatgatac cgcgagaacc acgctcaccg    3780
gctccagatt tatcagcaat aaaccagcca gccggaaggg ccgagcgcag aagtggtcct    3840
gcaactttat ccgcctccat ccagtctatt aattgttgcc gggaagctag agtaagtagt    3900
tcgccagtta atagtttgcg caacgttgtt gccattgcta caggcatcgt ggtgtcacgc    3960
tcgtcgtttg gtatggcttc attcagctcc ggttcccaac gatcaaggcg agttacatga    4020
tcccccatgt tgtgcaaaaa agcggttagc tccttcggtc ctccgatcgt tgtcagaagt    4080
aagttggccg cagtgttatc actcatggtt atggcagcac tgcataattc tcttactgtc    4140
atgccatccg taagatgctt ttctgtgact ggtgagtact caaccaagtc attctgagaa    4200
tagtgtatgc ggcgaccgag ttgctcttgc ccggcgtcaa tacgggataa taccgcgcca    4260
catagcagaa ctttaaaagt gctcatcatt ggaaaacgtt cttcggggcg aaaactctca    4320
aggatcttac cgctgttgag atccagttcg atgtaaccca ctcgtgcacc caactgatct    4380
tcagcatctt ttactttcac cagcgtttct gggtgagcaa aaacaggaag gcaaaatgcc    4440
gcaaaaaagg gaataagggc gacacggaaa tgttgaatac tcatactctt cctttttcaa    4500
tattattgaa gcatttatca gggttattgt ctcatgagcg gatacatatt tgaatgtatt    4560
tagaaaaata acaaataggg gttccgcgc acatttcccc gaaaagtgcc ac             4612
```

<210> SEQ ID NO 41
<211> LENGTH: 4606
<212> TYPE: DNA
<213> ORGANISM: Desulfobacula toluolica

<400> SEQUENCE: 41

```
ctaaattgta agcgttaata ttttgttaaa attcgcgtta aatttttgtt aaatcagctc      60
attttttaac caataggccg aaatcggcaa aatcccttat aaatcaaaag aatagaccga     120
```

-continued

```
gataggggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgccatgag ctcagctggt gacaattaat catcggctcg tataatgtgt    420
ggaattgaat cgatataagg aggttaatca tatgaataat gataaggtaa aacatacttt    480
tcatggtctg atggatatgg cgggaattaa ggttaacggg ccacgtccct atgatatcca    540
ggttaaaaat gataatttgt accaaagggt attgagcaaa gccgcactgg gacttggcga    600
gtcctacatg gatcaatggt gggaatgcaa agcccttgac aggtttattg ataaaattct    660
tcgtgcagat cttgtaaaca agattcgtca ggactggaac accacatggg aaatttttaaa    720 agccagaatt attaacctgc agaaacctga tcgtgcattc atggtaggtc aaaaacatta    780
tgatgtcggc aatgaccttt accaggccat gctcgacaaa agaatgcagt atacctgcgg    840
ctattgggag acggcagaca cccttgaatc ggcccagaaa gccaaactgg aactggtatg    900
caggaaaatc ggcctgaagc cgggaatgaa ggtgttggaa cttggatgcg ggtttggcgg    960
gtttgcacgg tatgccgctc aaaaatatga tgcccatgtc actggattta cagtgtccag   1020
ggaacaggct gcgtttgcaa aaaacagtg caggggcctg cccgttgata tccggctcga   1080
tgattacagg aacgcatcag ggttgtatga cagggttgtt tccataggga tgatggagca   1140
tgtcgggtac aagaactaca gggcctatat ggaactgaca aatcgtctgc tcaaggatga   1200
aggcattgct tttgttcata ccattggcag caatgtcagc cgtaaaattt gcaatccctg   1260
gacggtcaag tatattttc ccaattcctc cctgccatcc atagcttttc tggggaaagc   1320
catggaaggg ctttttgtgg tggaagattg gcataatttt ggtgaggatt acgataaaac   1380
cctgatggcc tggcatgaga attttaaaaa agcctggcca ggtctgaaag aaaaatacga   1440
tgaacggttt tacaggatgt ggacatatta tcttttaagc tgtgccggcg gattccgttc   1500
acgaagcatg caattatggc agattgtaat gaccaaaccc ggcaggaccc gtccggaccg   1560
ccggataaat tgaggaaatc cattatgata gattctaaaa taattattgt cggcggaggc   1620
cctgcgggtt ctgcatgtgc atggaaacta aagcaggcag aagaacaaat ccttatcctg   1680
gaccgaaagc cttttccgcg ttccaaattg tgcgccggat ggataaaccc aaaggcattg   1740
aatgccattg attttaaaaa acaggaatat ccttttttgc ttcatccggt tgacaggatt   1800 cattttttacc tgttcggggt tcatattccg gttcaaacac gtcagtatgc catacgcaga   1860
gttgaatttg atgactggat ggtgaagcgg gccaatgttc ctgtgcatac gcatacagtt   1920
aaaaaaatca ttaaaaagaa cggttttat attattgata accaatacag gtgccaatat   1980
cttgttgggg ccggaggcac ccattgtcca gtgttcagag tttttttcag caaagatgaa   2040
aaaagaccca tgaagtctat gattgcagca gttgaacaag agtatgtttg cgattaccag   2100
gacagccgat gccacatttg gttttttgac aaaaaacttc ctggatattc ctggtatctt   2160
cccaagggca atggttggtt aaatatcggg atcggcggaa aattttttgaa atgaaaaaa   2220 cagggcacaa ccattataga tcattggaga tatttttaccc aaaaacttt aaggctctca   2280 ttgatcaaca aaattccgga aatgcccaaa ggtcatacct actatctgcg ccaccgtatg   2340
aaccaatgtc aaaaggacaa tgtgtttgtg atcggggatg cagccggttt gtccacactt   2400
gatatgggag agggtatcca tgcggcaatt gccggtggaa ttctggctgc aaaagccatt   2460
```

-continued

```
gtcgagaaaa aagagttccg ggttgaatct ttgggaaaat tcagtctgcc tggtatgatt      2520
tttcaaaaca agaggtctca caaagaattt ttttaacctc aaaatatatt ttccctctat      2580
cttctcgttg cgcttaattt gactaattct cattagcgag gtacctctta attaactggc      2640
ctcatgggcc ttccgctcac tgcccgcttt ccagtcggga aacctgtcgt gccagctgca      2700
ttaacatggt catagctgtt tccttgcgta ttgggcgctc tccgcttcct cgctcactga      2760
ctcgctgcgc tcggtcgttc gggtaaagcc tggggtgcct aatgagcaaa aggccagcaa      2820
aaggccagga accgtaaaaa ggccgcgttg ctggcgtttt tccataggct ccgcccccct      2880
gacgagcatc acaaaaatcg acgctcaagt caggaggtggc gaaacccgac aggactataa      2940
agataccagg cgtttccccc tggaagctcc ctcgtgcgct ctcctgttcc gaccctgccg      3000
cttaccggat acctgtccgc ctttctccct tcgggaagcg tggcgctttc tcatagctca      3060
cgctgtaggt atctcagttc ggtgtaggtc gttcgctcca agctgggctg tgtgcacgaa      3120
ccccccgttc agcccgaccg ctgcgcctta tccggtaact atcgtcttga gtccaacccg      3180
gtaagacacg acttatcgcc actggcagca gccactggta acaggattag cagagcgagg      3240
tatgtaggcg gtgctacaga gttcttgaag tggtggccta actacggcta cactagaaga      3300
acagtatttg gtatctgcgc tctgctgaag ccagttacct tcggaaaaag agttggtagc      3360
tcttgatccg gcaaacaaac caccgctggt agcggtggtt ttttgtttg caagcagcag      3420 attacgcgca gaaaaaaagg atcctttga tcttttctac ggggtctgac      3480
gctcagtgga acgaaaactc acgttaaggg attttggtca tgagattatc aaaaaggatc      3540
ttcacctaga tcctttttaaa ttaaaaatga agttttaaat caatctaaag tatatatgag      3600
taaacttggt ctgacagtta ccaatgctta atcagtgagg cacctatctc agcgatctgt      3660
ctatttcgtt catccatagt tgcctgactc cccgtcgtgt agataactac gatacgggag      3720
ggcttaccat ctggccccag tgctgcaatg ataccgcgag aaccacgctc accggctcca      3780
gatttatcag caataaacca gccagccgga agggccgagc gcagaagtgg tcctgcaact      3840
ttatccgcct ccatccagtc tattaattgt tgccgggaag ctagagtaag tagttcgcca      3900
gttaatagtt tgcgcaacgt tgttgccatt gctacaggca tcgtggtgtc acgctcgtcg      3960
tttggtatgg cttcattcag ctccggttcc caacgatcaa ggcgagttac atgatccccc      4020
atgttgtgca aaaagcggt tagctccttc ggtcctccga tcgttgtcag aagtaagttg      4080
gccgcagtgt tatcactcat ggttatggca gcactgcata attctcttac tgtcatgcca      4140
tccgtaagat gcttttctgt gactggtgag tactcaacca agtcattctg agaatagtgt      4200
atgcggcgac cgagttgctc ttgcccggcg tcaatacggg ataataccgc gccacatagc      4260
agaactttaa aagtgctcat cattggaaaa cgttcttcgg ggcgaaaact ctcaaggatc      4320
ttaccgctgt tgagatccag ttcgatgtaa cccactcgtg cacccaactg atcttcagca      4380
tcttttactt tcaccagcgt ttctgggtga gcaaaaacag gaaggcaaaa tgccgcaaaa      4440
aagggaataa gggcgacacg gaaatgttga atactcatac tcttcctttt tcaatattat      4500
tgaagcattt atcagggtta ttgtctcatg agcggataca tatttgaatg tatttagaaa      4560
aataaacaaa tagggggttcc gcgcacattt ccccgaaaag tgccac                    4606
```

<210> SEQ ID NO 42
<211> LENGTH: 4951
<212> TYPE: DNA
<213> ORGANISM: Marinobacter hydrocarbonoclasticus

<400> SEQUENCE: 42

```
ctaaattgta agcgttaata ttttgttaaa attcgcgtta aattttttgtt aaatcagctc    60
atttttttaac caataggccg aaatcggcaa aatcccttat aaatcaaaag aatagaccga   120
gatagggttg agtggccgct acagggcgct cccattcgcc attcaggctg cgcaactgtt   180
gggaagggcg tttcggtgcg ggcctcttcg ctattacgcc agctggcgaa aggggatgt    240
gctgcaaggc gattaagttg ggtaacgcca gggttttccc agtcacgacg ttgtaaaacg   300
acggccagtg agcgcgacgt aatacgactc actatagggc gaattggcgg aaggccgtca   360
aggcctaggc gcgccatgag ctcagctggt gacaattaat catcggctcg tataatgtgt   420
ggaattgaat cgatataagg aggttaatca tatggcacag gcacagctc caaagacgga    480
ctattctgac agcaacacca aagcacatgt tcttagcctg ccactggaaa acagtcaggc   540
tgatcgcgaa ccacacagct atgaacgctg gctgatcgcc aagttgatgc gaatggccgg   600
ttcacccgcc atacgcttcc agctgtggaa tggcgaggtc atcgagccag agcaagggct   660
agcccgcttc accctgcacc tgaaggatca caaggcactc tactccctcg ttgccaaccc   720
caacctcgcc ttcggcgatc tgtacagcgc tggccgcctg gagatcgatg gcgacctgcc   780
tgatctgatg gaaagccttt accgatcagt ccacgccgcc cggcagaaat ggccaaaatg   840
gctggatgcg ctttggaaga atcacaaccc cagagcaacc ggcatttccg aggccaagga   900
aaacattcac caccactacg acctgggcaa cgagttttac caactctggc tggacaacgc   960
agaaatgcag tacacctgtg cctattacga gcaccccggt aacacactgg agcaggcaca  1020
actggccaaa ctggagcatg tgtgccggaa gctgcgcctg aggccaggca tgacggtggt  1080
ggaagccggc tgtggctggg gcggcctggc ccgttatatg gcccgcaact acggcgtgaa  1140
agttcactcc tacaacatat cccgtgaaca actggcatac gcccaggccg agtctgaacg  1200
ccaagggctc gatggtctta ttacctatgt cgaggacgac taccgcaata tcaccggcca  1260
gtacgacgca ttcgtctctg ttggcatgct ggagcatgtt ggcaaggaaa actaccgagc  1320
cctgtcggag ctgatcaagc gcagcctgaa acccaacggc atagctctgc tccacagtat  1380
cgggcgcaac cgcccatgc taatgaatgc ctggatagag aagcggatct ttcccggcgc   1440
ctaccctccc agtatcggcg agtttatgga aatctgtgag cacggcgact tctcggtact  1500
ggatgtggag aacctgcggc tgcactatgc ccagaccctg agccactgga cggagcgctt  1560
cgaagccaat gccgagcgcg ttaccgagat gtacgacgaa cacttcaccc gcgcctggcg  1620
gctttatctg gcgggctcaa ttgcagcatt ccggcccggt tctctgcagc tgttccaggt  1680
ggtgtttacc catggcgata caaccagct gccccagagc cggcaggact tgtatgcgtt   1740
tccggcaaca ccgagggca actgaggaaa tccattatgg atcactacga tgtgatcatt  1800
gttggtgccg gccggccgg ttccaccctg gcacgcagct tggaggatgc cgggaagaat   1860
gtactggtca tcgacaaagc cagcttcccc cgggacaaaa cctgcgcggg ctgggtaaca  1920
cctgccgtta tggagagcct ggacatcaac ccggcgaatt acgccaatgg ccgaacccctt  1980
cagcctattc gtcgtttccg cattggcatg atggggcagc ctgcggtgga aacgaccac   2040
catggcattg tcagttacgg catacggcgc tgcgaattcg acgctttcct gctcgagcgg  2100
gtacgctctc caaagcaact tgccacaccc gtcaaatcca tcgtccggaa caacggccac  2160
tgggtggtca acaaccagtg gcaggcccg cttctgattg gcgccggggg gcacttctgc   2220
ccggttgcca gacagctggg cactggcccc ggtaaacacg aaacagtggt cgccgccaag  2280
```

```
gaagtggagt ttgagatgac accggaacag gccgatgcct gtgaagcccg ggggdataca    2340
cctgagctct ggttctgccg ggatctcaag ggttatgcct gggtattccg caaaggtaat    2400
ttcctgaaca ttggcctggg gcgggaagac aaccaccggc taacggatca cctggaggca    2460
ttcgtagacg atatgaagca cgacgggcga atccccgcag acctgccggg gcgattcaaa    2520
ggccatgcct acctgttgta cgcccatgca gatcggccac tggtagacga cggcgtattg    2580
ctgatcggag atgcagcggg cctggcttac acccagagcg tgagggtat ccgccctgcc    2640
attgaatccg ccttgatggc ggccgaggtg attcttaacg ccacagattt ttctgccgcc    2700
gcgctacagc gctacggtga gcgcattgcg gaacgctttg gcaaccgtgc cagtgagcag    2760
gcagctggct gggaactgcc ggaatggctg aagcagcccg tcgccagcac attgatgcgc    2820
tcacactggt ttacccgaaa ggtagtgacg gagaaatggt tcctgcatca ggatgtgcct    2880
accctgaaag ccgtcggctg acctcaaaat atattttccc tctatcttct cgttgcgctt    2940
aatttgacta attctcatta gcgaggtacc tcttaattaa ctggcctcat gggccttccg    3000
ctcactgccc gctttccagt cgggaaacct gtcgtgccag ctgcattaac atggtcatag    3060
ctgtttcctt gcgtattggg cgctctccgc ttcctcgctc actgactcgc tgcgctcggt    3120
cgttcgggta agcctggggg tgcctaatga gcaaaaggcc agcaaaggcc caggaaccgt    3180
aaaaaggccg cgttgctggc gtttttccat aggctccgcc cccctgacga gcatcacaaa    3240
aatcgacgct caagtcagag gtggcgaaac ccgacaggac tataaagata ccaggcgttt    3300
ccccctggaa gctccctcgt gcgctctcct gttccgaccc tgccgcttac cggatacctg    3360
tccgcctttc tcccttcggg aagcgtggcg ctttctcata gctcacgctg taggtatctc    3420
agttcggtgt aggtcgttcg ctccaagctg ggctgtgtgc acgaaccccc cgttcagccc    3480
gaccgctgcg ccttatccgg taactatcgt cttgagtcca acccggtaag acacgactta    3540
tcgccactgg cagcagccac tggtaacagg attagcagag cgaggtatgt aggcggtgct    3600
acagagttct tgaagtggtg gcctaactac ggctacacta agaacagt atttggtatc    3660
tgcgctctgc tgaagccagt taccttcgga aaaagagttg gtagctcttg atccggcaaa    3720
caaaccaccg ctggtagcgg tggttttttt gtttgcaagc agcagattac gcgcagaaaa    3780
aaaggatctc aagaagatcc tttgatcttt tctacggggt ctgacgctca gtggaacgaa    3840
aactcacgtt aagggatttt ggtcatgaga ttatcaaaaa ggatcttcac ctagatcctt    3900
ttaaattaaa aatgaagttt taaatcaatc taaagtatat atgagtaaac ttggtctgac    3960
agttaccaat gcttaatcag tgaggcacct atctcagcga tctgtctatt tcgttcatcc    4020
atagttgcct gactccccgt cgtgtagata actacgatac gggagggctt accatctggc    4080
cccagtgctg caatgatacc gcgagaacca cgctcaccgg ctccagattt atcagcaata    4140
aaccagccag ccggaagggc cgagcgcaga agtggtcctg caactttatc cgcctccatc    4200
cagtctatta attgttgccg ggaagctaga gtaagtagtt cgccagttaa tagtttgcgc    4260
aacgttgttg ccattgctac aggcatcgtg gtgtcacgct cgtcgtttgg tatggcttca    4320
ttcagctccg gttcccaacg atcaaggcga gttacatgat cccccatgtt gtgcaaaaaa    4380
gcggttagct ccttcggtcc tccgatcgtt gtcagaagta agttggccgc agtgttatca    4440
ctcatggtta tggcagcact gcataattct cttactgtca tgccatccgt aagatgcttt    4500
tctgtgactg gtgagtactc aaccaagtca ttctgagaat agtgtatgcg gcgaccgagt    4560
tgctcttgcc cggcgtcaat acgggataat accgcgccac atagcagaac tttaaaagtg    4620
ctcatcattg gaaaacgttc ttcggggcga aaactctcaa ggatcttacc gctgttgaga    4680
```

| | |
|---|---|
| tccagttcga tgtaacccac tcgtgcaccc aactgatctt cagcatcttt tactttcacc | 4740 |
| agcgtttctg ggtgagcaaa acaggaagg caaaatgccg caaaaaggg aataagggcg | 4800 |
| acacggaaat gttgaatact catactcttc cttttcaat attattgaag catttatcag | 4860 |
| ggttattgtc tcatgagcgg atacatattt gaatgtattt agaaaaataa acaaataggg | 4920 |
| gttccgcgca catttccccg aaaagtgcca c | 4951 |

<210> SEQ ID NO 43
<211> LENGTH: 4867
<212> TYPE: DNA
<213> ORGANISM: Unknown
<220> FEATURE:
<223> OTHER INFORMATION: Thiohalospira halophila

<400> SEQUENCE: 43

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gataggggttg agtggccgct acagggcgct cccattcgcc attcaggctg cgcaactgtt | 180 |
| gggaagggcg tttcggtgcg ggcctcttcg ctattacgcc agctggcgaa aggggatgt | 240 |
| gctgcaaggc gattaagttg ggtaacgcca gggttttccc agtcacgacg ttgtaaaacg | 300 |
| acggccagtg agcgcgacgt aatacgactc actataggc gaattggcgg aaggccgtca | 360 |
| aggcctaggc gcgccatgag ctcagctggt gacaattaat catcggctcg tataatgtgt | 420 |
| ggaattgaat cgatataagg aggttaatca tatgcaaggg aacacgcccc acggtcgcgc | 480 |
| caagggcgca gacctggccc tggctgagcg gatcctcgcc ggcatgggga atcctgcgct | 540 |
| ggccgtgatc ctctgggacg gtagccgtgt cgggccgtcg gatacggtgg ccgatgtcgc | 600 |
| ggtcgccgat cggcgggcgt tgtgggccat tgccctgaat gcggatcttc acttcggcga | 660 |
| cctctatgcg gccggtcggg tgcgcatcga tggtgacctg cagaccttcc tggagacggg | 720 |
| gtatcgcgcc atggacgggc agccgacccc ctggccgttg cgcttcctcc accgctggca | 780 |
| gaatcggccg cgacggaact ccctgaacgg ctcccgggag aacatccacc atcactatga | 840 |
| cctgggcaat gacttctacc ggctctggct ggatcaggag gtcatgcagt acacctgcgc | 900 |
| ctactatccc agcgaatcgg ccagcctgga ggaggcacag atagccaagc tccaccatgt | 960 |
| ctgccgcaag ctgcggctca gccgggaga tacggtagtc gaggcgggtt gcggctgggg | 1020 |
| tggcctggct cgcttcatgg ccaagcatta tggcgtgaag gtacgcgcct ttaatgtctc | 1080 |
| gcaggagcag ttgcgcttcg cccgggagga ggccgaacgg caggggctct cggatcgggt | 1140 |
| ggagtacgtc gaggacgact accggaacat tgagggggacc tacgacgtct tcgtctcggt | 1200 |
| gggtatgctc gagcatgtcg gcacggagca atatccggaa ctgggggcag tgatcgatcg | 1260 |
| ggtgcttgcc ccccacggcc ggggcctcat ccacaccatc gggcggaatc ggccccagct | 1320 |
| catgaatccg tggatcgaaa agcgtatctt tcccgggggcc taccccccca ccctgcggga | 1380 |
| gatggcggcc atcttcgagc cgtatgcctt ctcgatccag gacgtggaaa acatccggct | 1440 |
| ccactacgcg cggacccctcc agcactggct ggagcggttc gaggccaacg tggagacggt | 1500 |
| ccggcagatg ttcgacgagc acttcgtgcg gacctggcgg ctctacctcg ccggctccat | 1560 |
| tgccagcttc accacggggg agctgcagct cttccagacc gtctttacac ggccggacta | 1620 |
| caatgagctc ccctggagcc gcgcctatct ctacaccgcc ggggaggaag gggcatgagg | 1680 |
| aaatccatta tgagcgaacg cagcgacgtc ctcatcgtcg gcggcggtcc cggcggttcc | 1740 |

```
accctgggtc gggcgctcgc tcggcagggc ctggatgtga ccatcgtcga caagcagacc    1800
ttcccccggg acaaggtctg cgccggctgg gtgaccccg cggtcatgga gtccctggac     1860
ctggacccga acgaatacgc ccgggatgcc gtcctgcagc ccatccacgc ctttcgcacc    1920
ggcatgctcg gtcagcgcac cgtggtctct cgctacccgg aaccggcgag ttacgggatc    1980
cggcgctacg agttcgatgc ctggctgctg aacgggcca tcaacgacgg tgtccgtacc     2040
gcgcagggcc agcctctgaa agagctgcgc cgggaagacg gtgagtgggt gctcaatgac    2100
catctgcgca caccgctgct catcggtgcc ggcggccact tctgtcccgt ggcgcgccac    2160
ctcggggcgg cgaagcccgg ctcctcggag accgcggtcc acgcccagga gatcgagttc    2220
gagatgacgc cggagcaggc ggctgcctgt ccggtggagg ccgacgtgcc ggagctctac    2280
ttcctccgcg acctctccgg ctacggctgg atcgtgcgca aggggactg gctgaatatc     2340 ggcctcggtc gcgaggggg ccagaagctc ggtgagcagg taagcgcctt cgccgaggag     2400
ctcaaggcca tggggcggct ccacatcgac ccaccgagca agttcaaggg ccacgcctac    2460
ctgctccacg gccacagccc gcggccgccg gttcacgacg gggccctgct catcggtgac    2520
gcagccggcc tggcctatcc gcagagcggc gaggggatcc ggccggcagt ggagtccgcg    2580 ctcatgcgg cggaggtcat tggtgccgcg ggtggcgatt acagtgccga ccgcctggcc     2640
gccttcggcg accggctaca gcgccgcttc ggcaaggggt cggcggcggg tgaacccggg    2700
ccggtgaaac aggccctggc gcggccgctc atggcctcga ctggttcgc ccgccacgtc     2760 atcctcgacc gttggttcct ccaccgccac caggcccct tggccccggc ggcctgacct     2820
caaaatatat tttccctcta tcttctcgtt gcgcttaatt tgactaattc tcattagcga    2880
ggtacctctt aattaactgg cctcatgggc cttccgctca ctgcccgctt ccagtcggg     2940 aaacctgtcg tgccagctgc attaacatgg tcatagctgt ttccttgcgt attgggcgct    3000
ctccgcttcc tcgctcactg actcgctgcg ctcggtcgtt cgggtaaagc ctggggtgcc    3060
taatgagcaa aaggccagca aaaggccagg aaccgtaaaa aggccgcgtt gctggcgttt    3120
ttccataggc tccgcccccc tgacgagcat cacaaaaatc gacgctcaag tcagaggtgg    3180
cgaaacccga caggactata agataccag gcgtttcccc ctggaagctc cctcgtgcgc     3240
tctcctgttc cgaccctgcc gcttaccgga tacctgtccg cctttctccc ttcgggaagc    3300
gtggcgcttt ctcatagctc acgctgtagg tatctcagtt cggtgtaggt cgttcgctcc    3360
aagctgggct gtgtgcacga accccccgtt cagcccgacc gctgcgcctt atccggtaac    3420
tatcgtcttg agtccaaccc ggtaagacac gacttatcgc cactggcagc agccactggt    3480
aacaggatta gcagagcgag gtatgtaggc ggtgctacag agttcttgaa gtggtggcct    3540
aactacggct acactagaag aacagtattt ggtatctgcg ctctgctgaa gccagttacc    3600
ttcggaaaaa gagttggtag ctcttgatcc ggcaaacaaa ccaccgctgg tagcggtggt    3660 tttttgttt gcaagcagca gattacgcgc agaaaaaaag gatctcaaga agatcctttg     3720
atcttttcta cggggtctga cgctcagtgg aacgaaaact cacgttaagg gattttggtc    3780
atgagattat caaaaaggat cttcacctag atccttttaa attaaaaatg aagttttaaa    3840
tcaatctaaa gtatatatga gtaaacttgg tctgacagtt accaatgctt aatcagtgag    3900
gcacctatct cagcgatctg tctatttcgt tcatccatag ttgcctgact ccccgtcgtg    3960
tagataacta cgatacggga gggcttacca tctggcccca gtgctgcaat gataccgcga    4020
gaaccacgct caccggctcc agatttatca gcaataaacc agccagccgg aagggccgag    4080
cgcagaagtg gtcctgcaac tttatccgcc tccatccagt ctattaattg ttgccgggaa    4140
```

```
gctagagtaa gtagttcgcc agttaatagt ttgcgcaacg ttgttgccat tgctacaggc   4200
atcgtggtgt cacgctcgtc gtttggtatg gcttcattca gctccggttc ccaacgatca   4260
aggcgagtta catgatcccc catgttgtgc aaaaaagcgg ttagctcctt cggtcctccg   4320
atcgttgtca gaagtaagtt ggccgcagtg ttatcactca tggttatggc agcactgcat   4380
aattctctta ctgtcatgcc atccgtaaga tgcttttctg tgactggtga gtactcaacc   4440
aagtcattct gagaatagtg tatgcggcga ccgagttgct cttgcccggc gtcaatacgg   4500
gataataccg cgccacatag cagaacttta aaagtgctca tcattggaaa acgttcttcg   4560
gggcgaaaac tctcaaggat cttaccgctg ttgagatcca gttcgatgta acccactcgt   4620
gcacccaact gatcttcagc atcttttact ttcaccagcg tttctgggtg agcaaaaaca   4680
ggaaggcaaa atgccgcaaa aaagggaata agggcgacac ggaaatgttg aatactcata   4740
ctcttccttt ttcaatatta ttgaagcatt tatcagggtt attgtctcat gagcggatac   4800
atatttgaat gtatttagaa aaataaacaa atagggggttc cgcgcacatt tccccgaaaa   4860
gtgccac                                                             4867
```

<210> SEQ ID NO 44
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 44

Ala Gly Gly Ala Glu Gly Gly Asn Gly Gly Gly Ala
1               5                   10

<210> SEQ ID NO 45
<211> LENGTH: 382
<212> TYPE: PRT
<213> ORGANISM: Escherichia coli

<400> SEQUENCE: 45

Met Ser Ser Cys Ile Glu Glu Val Ser Val Pro Asp Asp Asn Trp
1               5                   10                  15

Tyr Arg Ile Ala Asn Glu Leu Leu Ser Arg Ala Gly Ile Ala Ile Asn
                20                  25                  30

Gly Ser Ala Pro Ala Asp Ile Arg Val Lys Asn Pro Asp Phe Phe Lys
            35                  40                  45

Arg Val Leu Gln Glu Gly Ser Leu Gly Leu Gly Glu Ser Tyr Met Asp
        50                  55                  60

Gly Trp Trp Glu Cys Asp Arg Leu Asp Met Phe Phe Ser Lys Val Leu
65                  70                  75                  80

Arg Ala Gly Leu Glu Asn Gln Leu Pro His His Phe Lys Asp Thr Leu
                85                  90                  95

Arg Ile Ala Gly Ala Arg Leu Phe Asn Leu Gln Ser Lys Lys Arg Ala
            100                 105                 110

Trp Ile Val Gly Lys Glu His Tyr Asp Leu Gly Asn Asp Leu Phe Ser
        115                 120                 125

Arg Met Leu Asp Pro Phe Met Gln Tyr Ser Cys Ala Tyr Trp Lys Asp
    130                 135                 140

Ala Asp Asn Leu Glu Ser Ala Gln Gln Ala Lys Leu Lys Met Ile Cys
145                 150                 155                 160

```
Glu Lys Leu Gln Leu Lys Pro Gly Met Arg Val Leu Asp Ile Gly Cys
                165                 170                 175

Gly Trp Gly Gly Leu Ala His Tyr Met Ala Ser Asn Tyr Asp Val Ser
            180                 185                 190

Val Val Gly Val Thr Ile Ser Ala Glu Gln Lys Met Ala Gln Glu
        195                 200                 205

Arg Cys Glu Gly Leu Asp Val Thr Ile Leu Leu Gln Asp Tyr Arg Asp
    210                 215                 220

Leu Asn Asp Gln Phe Asp Arg Ile Val Ser Val Gly Met Phe Glu His
225                 230                 235                 240

Val Gly Pro Lys Asn Tyr Asp Thr Tyr Phe Ala Val Val Asp Arg Asn
                245                 250                 255

Leu Lys Pro Glu Gly Ile Phe Leu Leu His Thr Ile Gly Ser Lys Lys
            260                 265                 270

Thr Asp Leu Asn Val Asp Pro Trp Ile Asn Lys Tyr Ile Phe Pro Asn
        275                 280                 285

Gly Cys Leu Pro Ser Val Arg Gln Ile Ala Gln Ser Ser Glu Pro His
    290                 295                 300

Phe Val Met Glu Asp Trp His Asn Phe Gly Ala Asp Tyr Asp Thr Thr
305                 310                 315                 320

Leu Met Ala Trp Tyr Glu Arg Phe Leu Ala Ala Trp Pro Glu Ile Ala
                325                 330                 335

Asp Asn Tyr Ser Glu Arg Phe Lys Arg Met Phe Thr Tyr Tyr Leu Asn
            340                 345                 350

Ala Cys Ala Gly Ala Phe Arg Ala Arg Asp Ile Gln Leu Trp Gln Val
        355                 360                 365

Val Phe Ser Arg Gly Val Glu Asn Gly Leu Arg Val Ala Arg
    370                 375                 380

<210> SEQ ID NO 46
<211> LENGTH: 387
<212> TYPE: PRT
<213> ORGANISM: Archaeoglobus fulgidus

<400> SEQUENCE: 46

Met Tyr Asp Val Val Val Gly Ala Gly Pro Ala Gly Ser Met Ala
1               5                   10                  15

Ala Lys Thr Ala Ala Glu Gln Gly Leu Lys Val Leu Leu Val Glu Lys
                20                  25                  30

Arg Gln Glu Ile Gly Thr Pro Val Arg Cys Ala Glu Gly Ile Ser Arg
            35                  40                  45

Glu Ser Ile Glu Lys Phe Phe Glu Val Asp Lys Lys Trp Ile Ala Ala
        50                  55                  60

Glu Val Thr Gly Ala Lys Ile Tyr Ala Pro Asn Lys Thr Glu Ile Val
65                  70                  75                  80

Met Ser Glu Glu Met Ala Gly Asn Glu Val Gly Tyr Val Leu Glu Arg
                85                  90                  95

Lys Ile Phe Asp Arg His Val Ala Arg Leu Ala Ala Lys Ala Gly Ala
            100                 105                 110

Glu Val Tyr Val Lys Thr Ala Met Val Asp Phe Glu Arg Lys Asp Gly
        115                 120                 125

Lys Val Lys Val Lys Leu Arg Arg Leu Gly Glu Asp Trp Glu Val Glu
    130                 135                 140
```

-continued

```
Thr Lys Ile Leu Ile Gly Ala Asp Gly Val Glu Ser Lys Ile Gly Arg
145                 150                 155                 160

Lys Ala Gly Ile Ile Lys Thr Leu Lys Leu Asn Glu Val Glu Ser Cys
            165                 170                 175

Ala Gln Tyr Leu Met Thr Gly Leu Asp Ile Asp Glu Ser Tyr Thr Tyr
            180                 185                 190

Phe Tyr Leu Gly Arg Glu Leu Ala Pro Gly Gly Tyr Ala Trp Ile Phe
        195                 200                 205

Pro Lys Gly Asn Gly Ser Ala Asn Val Gly Ile Gly Val Leu Pro Lys
        210                 215                 220

Met Ala Glu Arg Thr Ala Lys Glu Tyr Leu Asp Ala Phe Ile Glu Lys
225                 230                 235                 240

Glu Gly Ile Glu Gly Lys Ile Val Glu Phe Val Ala Gly Ala Val Pro
                245                 250                 255

Val Tyr Gly Glu Ile Glu Thr Ala Val Ala Asp Asn Ile Met Leu Ala
                260                 265                 270

Gly Asp Ala Ala Tyr His Ala Asp Pro Ile Thr Gly Gly Gly Ile Ala
            275                 280                 285

Asn Ala Leu Ser Ala Gly Tyr Tyr Ala Gly Lys Val Ala Ala Glu Ala
            290                 295                 300

Val Gln Lys Asn Asp Phe Ser Ala Asp Phe Leu Arg Arg Tyr Asp Glu
305                 310                 315                 320

Leu Trp Lys Asn Asp Phe Gly Lys Lys Leu Arg Arg Asn Lys Lys Leu
                325                 330                 335

Gln Leu Lys Phe Ile Asp Met Asp Ala Leu Leu Asn Lys Leu Ala
                340                 345                 350

Gly Ala Ile Ala Gly Lys Asn Leu Arg Glu Met Ser Val Ala Ala Ile
            355                 360                 365

Val Lys Glu Leu Leu Lys Ala His Pro Lys Leu Leu Trp Asp Leu Lys
    370                 375                 380

Asp Leu Phe
385
```

UNITED STATES PATENT AND TRADEMARK OFFICE
CERTIFICATE OF CORRECTION

PATENT NO. : 11,236,373 B2
APPLICATION NO. : 16/648117
DATED : March 17, 2020
INVENTOR(S) : Arthur J. Shaw et al.

Page 1 of 1

It is certified that error appears in the above-identified patent and that said Letters Patent is hereby corrected as shown below:

In the Claims

In Claim 4, Column 128, Line 52, delete "*Halojilum*" and insert --*Halofilum*-- therefor.

In Claim 6, Column 128, Line 59, delete "reductase".

In Claim 12, Column 129, Line 22, delete "wherein to 15%" and insert --wherein 1% to 15%-- therefor.

In Claim 26, Column 130, Line 35, delete "reductase".

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*